(12) United States Patent
Gelman et al.

(10) Patent No.: US 9,822,362 B2
(45) Date of Patent: *Nov. 21, 2017

(54) COMPOSITIONS AND METHODS FOR TREATING LUNG DISEASE AND INJURY

(71) Applicants: Quark Pharmaceuticals Inc., Fremont, CA (US); Washington University, Saint Louis, MO (US)

(72) Inventors: Andrew E. Gelman, St. Louis, MO (US); Elena Feinstein, Rehovot (IL); Svetlana Adamsky, Gedera (IL); Igor Mett, Rehovot (IL); Hagar Kalinski, Rishon le Zion (IL); Sharon Avkin-Nachum, Nes Zionna (IL)

(73) Assignees: Quark Pharmaceuticals Inc., Ness Ziona (IL); Washington University, Saint Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/924,993

(22) Filed: Oct. 28, 2015

(65) Prior Publication Data

US 2016/0215284 A1 Jul. 28, 2016

Related U.S. Application Data

(63) Continuation of application No. 14/002,660, filed as application No. PCT/US2012/027169 on Mar. 1, 2012, now Pat. No. 9,205,100.

(60) Provisional application No. 61/448,723, filed on Mar. 3, 2011.

(51) Int. Cl.
*C12N 15/11* (2006.01)
*C12N 15/113* (2010.01)
*A61K 31/713* (2006.01)

(52) U.S. Cl.
CPC .......... *C12N 15/113* (2013.01); *A61K 31/713* (2013.01); *C12N 15/1138* (2013.01); *C12N 2310/11* (2013.01); *C12N 2310/14* (2013.01); *C12N 2310/321* (2013.01); *C12N 2310/344* (2013.01)

(58) Field of Classification Search
None
See application file for complete search history.

(56) References Cited

U.S. PATENT DOCUMENTS

| | | |
|---|---|---|
| 8,796,239 B2 | 8/2014 | Avkin-Nachum |
| 9,205,100 B2 | 12/2015 | Gelman et al. |
| 2010/0215588 A1 | 8/2010 | Skaliter |
| 2014/0005253 A1 | 1/2014 | Gelman et al. |
| 2014/0329878 A1 | 11/2014 | Feinstein et al. |

FOREIGN PATENT DOCUMENTS

| | | |
|---|---|---|
| CN | 101848724 A | 9/2010 |
| WO | 2005/085443 A2 | 9/2005 |
| WO | 2009/015107 A1 | 1/2009 |
| WO | 2009/019260 A2 | 2/2009 |
| WO | 2010/053971 A1 | 5/2010 |
| WO | 2010/053975 A1 | 5/2010 |
| WO | 2010/118334 A1 | 10/2010 |
| WO | 2010/131009 A2 | 11/2010 |

OTHER PUBLICATIONS

Allshire. Molecular biology. RNAi and Heterochromatin—a Hushed-Up Affair. Science. Sep. 13, 2002;297 (5588):1818-1819.
Arslan et al.. TLR2 and TLR4 in Ischemia Reperfusion Injury. Mediators Inflamm. 2010;2010:704202 (8 pages).
Bass, RNA interference. The short answer. Nature. May 24, 2001;411 (6836):428-429.
Bernstein et al., Role for a bidentate ribonuclease in the initiation step of RNA interference. Nature Jan. 18, 2001; 409(6818):363-366.
Bettinger et al., Size Reduction of Galactosylated PEI/DNA Complexes Improves Lectin-Mediated Gene Transfer Into Hepatocytes. Bioconjug Chem. Jul.-Aug. 1999;10(4):558-561.
Brody and Gold, Aptamers as therapeutic and diagnostic agents. J Biotechnol. Mar. 2000;74(1):5-13.
Clemens and Elia, The Double-Stranded RNA-Dependent Protein Kinase PKR: Structure and Function. J Interferon Cytokine Res. Sep. 1997;17(9):503-524.
Devaraj et al., Increased secretion of IP-10 from monocytes under hyperglycemia is via the TLR2 and TLR4 pathway. Cytokine. Jul. 2009;47(1 ):6-10.
Elm En et al., Locked nucleic acid (LNA) mediated improvements in siRNA stability and functionality. Nucleic Acids Res. Jan. 14, 2005;33(1):439-447.
Elson et al., Contribution of Toll-like receptors to the innate immune response to Gram-negative and Gram-positive bacteria. Blood. Feb. 15, 2007;109(4):1574-1583.
Ferentz and Verdine, Disulfide Cross-Linked Oligonucleotides. JAm Chem Soc. 1991;113:4000-4002.

(Continued)

*Primary Examiner* — Kate Poliakova-Georgantas
(74) *Attorney, Agent, or Firm* — Nutter McClennen & Fish LLP; Konstantin Linnik

(57) ABSTRACT

Disclosed herein are therapeutic methods for treating lung diseases, disorders and injury in a mammal, including treatment of acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema, bronchiolitis obliterans after lung transplantation and lung transplantation-induced acute graft dysfunction, including treatment, prevention or prevention of progression of primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD) after organ transplantation, in particular in lung transplantation, comprising down-regulating the TLR2 gene or both the TLR2 gene and TLR4 gene. Provided herein are compositions, methods and kits for treating lung diseases, disorders and injury.

19 Claims, 7 Drawing Sheets

(56) References Cited

OTHER PUBLICATIONS

Furgeson et al., Modified Linear Polyethylenimine-Cholesterol Conjugates for DNA Complexation. Bioconjug Chem.; Jul.-Aug. 2003;14(4):840-847.
Godbey et al., Poly(ethylenimine) and its role in gene delivery. J Control Release. Aug. 5, 1999;60(2-3):149-160.
Gold et al., Diversity of Oligonucleotide Functions. Annu Rev Biochem. 1995;64:763-797.
Gonzalez et al., New Class of Polymers for the Delivery of Macromolecular Therapeutics. Bioconjug Chem.; Nov.-Dec. 1999; 10 (6): 10 68-1074.
Hermann and Patel, Adaptive Recognition by Nucleic Acid Aptamers. Science. Feb. 4, 2000;287(5454):820-825.
International Preliminary Report on Patentability issued in PCT/US2012/027169 dated Sep. 12, 2013.
International Search Report issued in PCT/US2012/027169 dated Jun. 11, 2012.
International Written Opinion issued in PCT/US2012/027169 dated Jun. 11, 2012.
International Preliminary Report on Patentability for Application No. PCT/US2012/027174, dated Sep. 12, 2013 (10 pages).
Izant and Weintraub, Constitutive and Conditional Suppression of Exogenous and Endogenous Genes by Anti-Sense RNA. Science. Jul. 26, 1985;229(4711):345-352.
Jaschke et al., Automated Incorporation of Polyethylene Glycol into Synthetic Oligonucleotides. Tetrahedron Lett.; 1993;34(2):301-304.
Jenuwein, Molecular biology. An RNA-Guided Pathway for the Epigenome. Science. Sep. 27, 2002;297 (5590)2215-2218.
Jiang et al.. "The role of Toll-like receptors in non-infectious lung injury", Cell Research, 2006, 693-701.
Jin et al, N-acetylcysteine inhibits activation of toll-like receptor 2 and 4 gene expression in the liver and lung after partial hepatic ischemia-reperfusion injury in mice, 2007, Hepatobiliary & Pancreatic Diseases International, vol. 6, 3: 284-289.
Jin et al., "N-acetylcysteine inhibits activation of toll-like receptor 2 and 4 gene expression in the liver and lung after partial hepatic ischemia-reperfusion injury in mice". Hepatobiliary Pancreat Dis Int, vol. 6, No. 3, Jun. 15, 2007: pp. 284-289.
Krupnick et al., Orthotopic Mouse Lung Transplantation as Experimental Methodology to Study Transplant and Tumor Biology. Nat Protoc. 2009;4(1 ):86-93.
Kunath et al., The Structure of PEG-Modified Poly( Ethylene I mines) Influences Biodistribution and Pharmacokinetics of Their Complexes with NF-kappa B Decoy in Mice. Pharm Res. Jun. 2002;19(6):810-817.
Kusser, Chemically modified nucleic acid aptamers for in vitro selections: evolving evolution. J Biotechnol. Mar. 2000;74(1 ):27-38.
Li et al., "The dendritic cell mannose receptor mediates allergen internalization and maturation involving notch 1 signaling". Clinical and Experimental Immunology, vol. 162, 2010: pp. 251-261.
Lieber et al., Stable High-Level Gene Expression in Mammalian Cells by T7 Phage RNA Polymerase. Methods Enzymol. 1993;217:47-66.
Paul et al., Effective expression of small interfering RNA in human cells. Nat Biotechnol. May 2002;20(5):505-508.
Shimamoto et al, Toll-Like Receptor 4 Mediates Lung Ischemia-Reperfusion Injury, 2006, Ann Thorac Surg., 82, 6: 2017-2023.
Strauss, Molecular biology. Candidate 'Gene Silencers' Found. Science. Oct. 29, 1999;286(5441 ):886.
Tokairin et al, Enhanced immediate inflammatory response to *Streptococcus pneumoniae* in the lungs of mice with pulmonary emphysema, 2008, Respirology, 13: 324-332.
Wu et al, Effect of nitric oxide on toll-like receptor 2 and 4 gene expression in rats with acute lung injury complicated by acute hemorrhage necrotizing pancreatitis, 2005, Hepatobilliary Pancreat Dis Int, vol. 4, 4: 609-613.

COMPOSITIONS AND METHODS FOR TREATING LUNG DISEASE AND INJURY

RELATED APPLICATIONS

This application is a Continuation of U.S. application Ser. No. 14/022,660, filed Sep. 17, 2013, which is a National Phase of International Application No. PCT/US12/27169, filed Mar. 1, 2012, which claims the benefit of U.S. Provisional Application Ser. No. 61/448,723, filed Mar. 3, 2011. The above applications are incorporated herein by reference in their entirety and for all purposes.

SEQUENCE LISTING

The instant application contains a Sequence Listing, which is entitled 115340_22802_sequence listing 28OCT15.txt, submitted on Oct. 28, 2015 and 2,279.79 kb in size and is hereby incorporated by reference in its entirety.

Throughout this application various patents and publications are cited. The disclosures of these documents in their entireties are hereby incorporated by reference into this application to more fully describe the state of the art to which this invention pertains.

FIELD OF THE INVENTION

Compositions, methods and kits for treating lung disease and injury are provided herein.

SUMMARY OF THE INVENTION

Compositions, methods and kits for treating lung diseases are provided herein. In certain aspects and embodiments, provided are compositions and methods for therapy for treating lung disorders or injury in a mammal, including treatment of acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema, lung transplantation-induced acute graft dysfunction and bronchiolitis obliterans after lung transplantation. In certain aspects and embodiments, provided are compositions and methods for combination therapy for treating or preventing inflammation and/or graft rejection associated with organ transplantation, in particular lung transplantation, including treatment, prevention or attenuation of progression of primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD) after organ transplantation, in particular in lung transplantation. In certain aspects and embodiments, provided are compositions and methods for combination therapy for treating lung disorders or injury in a mammal. The compositions and methods involve inhibiting the gene Toll-like receptor 2 (TLR2) or the genes Toll-like receptor 2 (TLR2) and Toll-like receptor 4 (TLR4).

In various aspects and embodiments, compositions, methods and kits provided herein may target, decrease, down-regulate or inhibit the expression/activity/function of the gene Toll-like receptor 2 (TLR2). In various aspects and embodiments, compositions, methods and kits provided herein may target, decrease, down-regulate or inhibit the expression/activity/function of the genes: (i) Toll-like receptor 2 (TLR2) and (ii) Toll-like receptor 4 (TLR4).

In one aspect, provided is a method for treating a lung disorder, disease or injury in a mammal in need thereof. The method may include administering to the mammal at least one therapeutic agent selected from a TLR2 inhibitor or a pharmaceutically acceptable salt or prodrug thereof, in an amount effective to treat the mammal.

In another aspect, provided is a method for treating a lung disorder, disease or injury in a mammal in need thereof. The method may include administering to the mammal at least two therapeutic agents selected from: (i) a TLR2 inhibitor or a pharmaceutically acceptable salt or prodrug thereof, and (ii) a TLR4 inhibitor or a pharmaceutically acceptable salt or prodrug thereof; in an amount effective to treat the mammal.

The methods may include preventing, treating, ameliorating, and/or slowing the progression of lung disorders or injury, such as, without being limited to, ARDS, acute lung injury, pulmonary fibrosis (idiopathic), bleomycin induced pulmonary fibrosis, mechanical ventilator induced lung injury, COPD and disease, disorder or injury associated with lung transplantation in a subject. The method may involve treating, ameliorating, and/or slowing the progression of the aforementioned diseases or conditions or associated symptoms or complications thereof by administering to said subject a therapeutically effective amount of a therapeutic agent directed to the gene TLR2. The method may involve treating, ameliorating, and/or slowing the progression of the aforementioned diseases or conditions or associated symptoms or complications thereof by administering to said subject a therapeutically effective amount of at least one therapeutic agent that down regulates TLR2 and at least one therapeutic agent that down regulates TLR4. The method may involve treating, ameliorating, and/or slowing the progression of the aforementioned diseases or conditions or associated symptoms or complications thereof by administering to said subject a therapeutically effective amount of a single therapeutic agent, which is capable of down-regulating the genes TLR2 and TLR4 and/or the gene products of the genes TLR2 and TLR4.

In various embodiments the provided methods of treating a lung disease, disorder or injury comprise inhibiting the gene Toll-like receptor 2 (TLR2) in combination with one or more additional treatment methods selected from the group consisting of surgery, steroid therapy, non-steroid therapy, antibiotic therapy, antiviral therapy, antifungal therapy, immunosuppressant therapy, anti-infective therapy, anti-hypertensive therapy and nutritional supplements. In various embodiments the additional treatment is administered prior to, subsequent to or concomitantly with the provided method for treating a lung disorder, disease or injury. In various embodiments the provided methods of treating a lung disease, disorder or injury comprise inhibiting the gene Toll-like receptor 2 (TLR2) in combination with immunosuppressant therapy. In various embodiments the provided methods of treating a lung disease, disorder or injury comprise inhibiting the genes Toll-like receptor 2 (TLR2) and Toll-like receptor 4 (TLR4) in combination with one or more additional treatment methods selected from the group consisting of surgery, steroid therapy, non-steroid therapy, antibiotic therapy, antiviral therapy, antifungal therapy, antimicrobial therapy, immunosuppressant therapy, anti-infective therapy, anti-hypertensive therapy and nutritional supplements. In various embodiments the provided methods of treating a lung disease, disorder or injury comprise down-regulating the gene Toll-like receptor 2 (TLR2) and the gene Toll-like receptor 4 (TLR4) in combination with immunosuppressant therapy.

In certain embodiments the provided methods may include one or more of the following:

A. Administration of a pharmaceutical composition comprising a therapeutic agent selected from a TLR2 inhibitor or a pharmaceutically acceptable salt or prodrug thereof; and a pharmaceutically acceptable carrier; or B. Co-administration, e.g. concomitantly or in sequence, of a therapeutically effective amount of at least two therapeutic agents, wherein at least one therapeutic agent is for down-regulating the gene TLR2 and at least one therapeutic agent is for down-regulating the gene TLR4; and the therapeutic agents are selected from: (i) a TLR2 inhibitor or a pharmaceutically acceptable salt or prodrug thereof, and (ii) a TLR4 inhibitor or a pharmaceutically acceptable salt or prodrug thereof; or C. Administration of a pharmaceutical composition comprising a combination of at least two therapeutic agents, wherein at least one therapeutic agent is for down-regulating the gene TLR2 and at least one therapeutic agent is for down-regulating the gene TLR4; and the therapeutic agents are selected from: (i) a TLR2 inhibitor or a pharmaceutically acceptable salt or prodrug thereof, and (ii) a TLR4 inhibitor or a pharmaceutically acceptable salt or prodrug thereof; and a pharmaceutically acceptable carrier; or D. Administration of a pharmaceutical composition comprising a therapeutic agent which is capable of down-regulating the genes TLR2 and TLR4 and/or the gene products of the genes TLR2 and TLR4. Non-limiting examples of such single agents are tandem and multi-armed RNAi molecules disclosed in PCT Patent Publication No. WO 2007/091269.

In one aspect, provided is a medicament that includes a therapeutic agent which target, decrease, down-regulate or inhibit the expression/activity/function of the gene TLR2, or a pharmaceutically acceptable salt or prodrug thereof. Therapeutic agents useful in the combination as provided herein include, but are not limited to, small organic molecule chemical compounds; proteins, antibodies or fragments thereof, peptides, peptidomimetics and nucleic acid molecules.

In another aspect, provided is a medicament that includes at least two therapeutic agents which target, decrease, down-regulate or inhibit the expression/activity/function of the genes: (i) TLR2 and (ii) TLR4, wherein at least one therapeutic agent down-regulates the gene TLR2 and at least one therapeutic agent down-regulates the gene TLR4; and the therapeutic agents are selected from: (i) a TLR2 inhibitor or a pharmaceutically acceptable salt or prodrug thereof, and (ii) a TLR4 inhibitor or a pharmaceutically acceptable salt or prodrug thereof. Therapeutic agents useful in the combination as provided herein include, but are not limited to, small organic molecule; proteins, antibodies or fragments thereof, peptides, peptidomimetics and nucleic acid molecules.

In some embodiments the therapeutic agent comprises a nucleic acid molecule. In some embodiments each nucleic acid molecule is independently selected from the group consisting of an antisense molecule, a short interfering nucleic acid (siNA), short interfering RNA (siRNA), double-stranded RNA (dsRNA), micro-RNA (miRNA) or short hairpin RNA (shRNA) that bind a nucleotide sequence (such as an mRNA sequence) encoding a target gene selected from TLR2 and TLR4, for example:

the mRNA coding sequence for human TLR2 exemplified by SEQ ID NO:1 (gi|68160956|ref|NM_003264.3| *Homo sapiens* toll-like receptor 2 (TLR2), mRNA), or the mRNA coding sequence for human TLR4 exemplified by SEQ ID NO:2 (gi|207028550|ref|NR_024169.1| *Homo sapiens* toll-like receptor 4 (TLR4), transcript variant 4, non-coding RNA); or the mRNA coding sequence for human TLR4 exemplified by SEQ ID NO:3 (gi|207028620|ref|NM_138554.3| *Homo sapiens* toll-like receptor 4 (TLR4), transcript variant 1, mRNA); or the mRNA coding sequence for human TLR4 exemplified by SEQ ID NO:4 (gi|207028451|ref|NR_024168.1| *Homo sapiens* toll-like receptor 4 (TLR4), transcript variant 3, non-coding RNA).

In various embodiments each nucleic acid molecule is or includes a dsRNA molecule or a siRNA molecule. In various embodiments, the nucleic acid molecule (a) includes a sense strand and an antisense strand; (b) each strand of the nucleic acid molecule is independently 17 to 40 nucleotides in length; (c) a 17 to 40 nucleotide sequence of the antisense strand is complementary to a sequence of an mRNA encoding human TLR2 (e.g., SEQ ID NO: 1) or TLR4 (e.g., SEQ ID NOs: 2-4); and (d) a 17 to 40 nucleotide sequence of the sense strand is complementary to the a sequence of the antisense strand and includes a 17 to 40 nucleotide sequence of an mRNA encoding human TLR2 (e.g., SEQ ID NO: 1) or TLR4 (e.g., SEQ ID NOs: 2-4).

A pharmaceutical product as provided herein may, for example, be a pharmaceutical composition including the therapeutic agent in a pharmaceutically acceptable carrier. A pharmaceutical product as provided herein may, for example, be a pharmaceutical composition including the first and second therapeutic agent in admixture in a pharmaceutically acceptable carrier. Alternatively, the pharmaceutical product may, for example, be a kit comprising a preparation of the first therapeutic agent and a preparation of the second therapeutic agent and, optionally, instructions for the simultaneous, sequential or separate administration of the preparations to a patient in need thereof.

In a first aspect, provided is a method of preventing or reducing the symptoms of primary graft dysfunction (PGD) in a recipient of a lung transplant, comprising administering to the recipient a therapeutically-effective amount of at least one TLR2 inhibitor or a pharmaceutically acceptable salt or prodrug thereof, and a therapeutically-effective amount of at least one TLR4 inhibitor or a pharmaceutically acceptable salt or prodrug thereof, thereby preventing or reducing the symptoms of PGD in the recipient. In various embodiments the symptoms of PGD include inflammation, acute graft rejection, graft rejection, ischemia-reperfusion injury, reperfusion injury, impaired pulmonary function, bronchiolitis obliterans, impaired blood oxygenation, increased inflammatory cytokine production, intra-graft and intra-airway accumulation of granulocytes, pulmonary edema and hypoxemia.

In some embodiments, the recipient of the lung transplant is a human that is at risk of developing or is being treated for primary graft dysfunction (PGD). In some embodiments the method as provided herein may, for example, be use for preventing or reducing the symptoms of cold ischemia-associated PGD. Alternatively, the method may, for example, be for preventing or reducing the symptoms of warm ischemia-associated PGD.

In various embodiments, the administration of the at least oneTLR2 inhibitor or a pharmaceutically acceptable salt or prodrug thereof, and the at least one TLR4 inhibitor or a pharmaceutically acceptable salt or prodrug thereof results in one or more of the following: reduced pulmonary edema, increased blood oxygenation, preserved blood oxygenation, improved pulmonary function, preserved pulmonary function in the recipient of a lung transplant and improved pulmonary function of the transplanted lung.

In various embodiments, the at least one TLR2 inhibitor and the at least one TLR4 inhibitor are administered to the recipient of a lung transplant prior to, during or following the lung transplantation.

In some embodiments, the at least one TLR2 inhibitor and the at least one TLR4 inhibitor are co-administered to the recipient in the same formulation. Alternatively, the at least one TLR2 inhibitor and the at least one TLR4 inhibitor are co-administered to the recipient in different formulations.

In some embodiments, the at least one TLR2 inhibitor and the at least one TLR4 inhibitor are co-administered to the recipient by the same route. In other embodiments, the at least one TLR2 inhibitor and the at least one TLR4 inhibitor are co-administered to the recipient by different routes. In various embodiments, the methods comprise simultaneous administration of the at least one TLR2 inhibitor and the at least one TLR4 inhibitor. In some embodiments, the methods comprise separate administration of the at least one TLR2 inhibitor and the at least one TLR4 inhibitor. In some embodiments, the methods comprise combined administration of the at least one TLR2 inhibitor and the at least one TLR4 inhibitor. In other embodiments, the methods comprise sequential administration of the at least one TLR2 inhibitor and the at least one TLR4 inhibitor.

In various embodiments the provided method of preventing or reducing the symptoms of primary graft dysfunction (PGD) in a recipient of a lung transplant, further comprises at least one additional treatment selected from the group consisting of surgery, steroid therapy, non-steroid therapy, antiviral therapy, antifungal therapy, antimicrobial therapy, immunosuppressant therapy, anti-infective therapy, anti-hypertensive therapy, nutritional supplements and any combination thereof. In various embodiments, the additional treatment is administered prior to, subsequent to or concomitantly with administering of at least one TLR2 inhibitor and at least one TLR4 inhibitor. In some embodiments, the additional treatment comprises immunosuppressant therapy.

In various embodiments, the route of administration of at least one TLR2 inhibitor and at least one TLR4 inhibitor is selected from: systemic administration or local administration. In various embodiments, the method of administration of at least one TLR2 inhibitor and at least one TLR4 inhibitor to the recipient of a lung transplant is selected from the group comprising: intravenous, intraarterial, intraperitoneal, intramuscular, intraportal, subcutaneous, direct injection, intratracheal instillation, inhalation, intranasal, pulmonary and administration via pump into the lung. In some embodiments, at least one TLR2 inhibitor and at least one TLR4 inhibitor are administered to the recipient of a lung transplant by inhalation. In another embodiments, at least one TLR2 inhibitor and at least one TLR4 inhibitor are administered to the recipient of a lung transplant by intratracheal instillation.

In various embodiments of the provided method of preventing or reducing the symptoms of primary graft dysfunction (PGD) in a recipient of a lung transplant, the at least one TLR2 inhibitor and the at least one TLR4 inhibitor are each independently selected from the group consisting of a small organic molecule, a protein, an antibody or fragment thereof, a peptide, a peptidomimetic and a nucleic acid molecule. In some embodiments, at least one inhibitor comprises a nucleic acid molecule. In other embodiments, each inhibitor comprises a nucleic acid molecule. In some embodiments, each inhibitor comprises a nucleic acid molecule and the first nucleic acid molecule is a double-stranded oligonucleotide that binds a nucleotide sequence encoding a TLR2 gene and the second nucleic acid molecule is a double-stranded oligonucleotide that binds a nucleotide sequence encoding a TLR4 gene. In some embodiments the double-stranded oligonucleotides are linked one to the other in tandem or annealed in RNAistar formation.

In some embodiments the first double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR2; and
(d) a 17 to 40 nucleotide sequence of the sense strand is complementary to the antisense strand;

and the second double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR4; and
(d) a 17 to 40 nucleotide sequence of the sense strand is complementary to the antisense strand.

In various embodiments the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some embodiments, the first double-stranded oligonucleotide and the second double-stranded oligonucleotide are co-administered to the recipient in the same formulation. In other embodiments, the first double-stranded oligonucleotide and the second double-stranded oligonucleotide are co-administered to the recipient in different formulations. In some embodiments, the first double-stranded oligonucleotide and the second double-stranded oligonucleotide are co-administered to the recipient by the same route. In some embodiments, the first double-stranded oligonucleotide and the second double-stranded oligonucleotide are co-administered to the recipient by different routes. In various embodiments the mode of administration of the first double-stranded oligonucleotide and the second double-stranded oligonucleotide to the recipient of the lung transplant is selected from the group comprising: separate, combined, simultaneous and sequential administration.

In some embodiments, the first double-stranded oligonucleotide and the second double-stranded oligonucleotide are formulated for administering to the recipient once. In other embodiments, the first double-stranded oligonucleotide and the second double-stranded oligonucleotide are formulated for administering to the recipient at least once-a-day. In yet other embodiments, the first double-stranded oligonucleotide and the second double-stranded oligonucleotide are formulated for multiple administrations to the recipient.

In some embodiments of the provided method of preventing or reducing the symptoms of primary graft dysfunction (PGD) in a recipient of a lung transplant, at least one double-stranded oligonucleotide in dependently comprises a structure (A1):

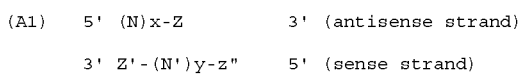

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present is independently 1-5 consecutive nucleotides or unconventional moieties or a combination thereof covalently attached at the 3' terminus of the strand in which it is present.
wherein z" may be present or absent, but if present is a capping moiety covalently attached at the 5' terminus of (N')y; wherein each of x and y is independently an integer between 17 and 40;
wherein the sequence of (N')y is complementary to the sequence of (N)x; and wherein (N)x comprises an antisense sequence to an mRNA selected from an mRNA encoding TLR2 and an mRNA encoding TLR4.

In various embodiments of structure (A1), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of structure (A1), x=y=19.

In some embodiments of structure (A1), (N)x comprises an antisense oligonucleotide selected from the group consisting of oligonucleotides having SEQ ID NOs: 723-1440, 2247-3052, 7076-8312 and 8459-8604 and (N')y comprises a complementary sense strand oligonucleotide selected from the group consisting of oligonucleotides having SEQ ID NOs: 5-722, 1441-2246, 5839-7075 and 8313-8458.

In various embodiments of the provided method of preventing or reducing the symptoms of primary graft dysfunction (PGD) in a recipient of a lung transplant, administration of the at least one double-stranded oligonucleotide that binds a nucleotide sequence encoding a TLR2 gene and the at least one double-stranded oligonucleotide that binds a nucleotide sequence encoding a TLR4 gene results in down-regulation of TLR2 expression and TLR4 expression, respectively.

In some embodiments of the provided method of preventing or reducing the symptoms of primary graft dysfunction (PGD) in a recipient of a lung transplant, at least one double-stranded compound independently comprises a structure (A2):

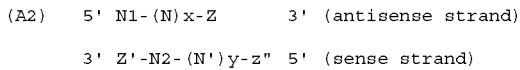

```
(A2)    5' N1-(N)x-Z        3'  (antisense strand)

3' Z'-N2-(N')y-z"   5'  (sense strand)
``` wherein each of N2, N and N' is independently an unmodified or modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein the sequence of (N')y is complementary to the sequence of (N)x and wherein (N)x is complementary to a consecutive sequence in an mRNA selected from an mRNA encoding TLR2 and an mRNA encoding TLR4;
wherein N1 is covalently bound to (N)x and is mismatched to the mRNA selected from an mRNA encoding TLR2 and an mRNA encoding TLR4;
wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine,
wherein z" may be present or absent, but if present is a capping moiety covalently attached at the 5' terminus of N2-(N')y; and
wherein each of Z and Z' is independently present or absent, but if present is independently 1-5 consecutive nucleotides or unconventional moieties or a combination thereof covalently attached at the 3' terminus of the strand in which it is present.

In various embodiments of structure (A2), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of structure (A2), x=y=18.

In some embodiments of structure (A2), the sequence of (N)x comprises an antisense strand oligonucleotide selected from the group consisting of oligonucleotides having SEQ ID NOs: 4153-5252, 5546-5838, 10319-12032, and 12085-12136 and the sequence of (N')y comprises a sense strand oligonucleotide selected from the group consisting of oligonucleotides having SEQ ID NOs: 3053-4152, 5253-5545, 8605-10318, and 12033-12084.

In a second aspect, provided is a method for treating a lung disorder, disease or injury in a patient in need thereof comprising administering to the patient a therapeutically-effective combination of at least one TLR2 inhibitor or a pharmaceutically acceptable salt or prodrug thereof, and at least one TLR4 inhibitor or a pharmaceutically acceptable salt or prodrug thereof, thereby treating the lung disorder, disease or injury in the patient. In various embodiments, the lung disorder, disease or injury is selected from acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, a disorder associated with lung transplantation and emphysema. In some embodiments, the lung disorder, disease or injury is a disorder associated with lung transplantation. In various embodiments, the lung disorder associated with lung transplantation is selected from the group consisting of inflammation, graft rejection, primary graft failure, ischemia-reperfusion injury, reperfusion injury, reperfusion edema, allograft dysfunction, acute graft dysfunction, pulmonary reimplantation response, bronchiolitis obliterans and primary graft dysfunction (PGD). In one embodiment, the lung disorder associated with lung transplantation is PGD.

In some embodiments of the provided method for treating a lung disorder, disease or injury in a patient in need thereof, the at least one TLR2 inhibitor and the at least one TLR4 inhibitor are co-administered to the recipient in the same formulation. In other embodiments, the at least one TLR2 inhibitor and the at least one TLR4 inhibitor are co-administered to the recipient in different formulations. In various embodiments, the at least one TLR2 inhibitor and the at least one TLR4 inhibitor are co-administered to the recipient by the same route. In other embodiments, the at least one TLR2 inhibitor and the at least one TLR4 inhibitor are co-administered to the recipient by different routes. In various embodiments the mode of administration of the at least one TLR2 inhibitor and the at least one TLR4 inhibitor is selected from the group comprising: separate, combined, simultaneous and sequential administration.

In some embodiments, the provided method for treating a lung disorder, disease or injury in a patient in need thereof, further comprises at least one additional treatment selected from the group consisting of surgery, steroid therapy, non-steroid therapy, antiviral therapy, antifungal therapy, antimicrobial therapy, immunosuppressant therapy, anti-infective therapy, anti-hypertensive therapy, nutritional supplements and any combination thereof. In some embodiments, the additional treatment comprises immunosuppressant therapy. In various embodiments, the additional treatment is administered prior to, subsequent to or concomitantly with administering of at least one TLR2 inhibitor and at least one TLR4 inhibitor.

In some embodiments of the provided method for treating a lung disorder, disease or injury in a patient in need thereof, the administering of at least one TLR2 inhibitor and at least one TLR4 inhibitor to the patient comprises systemic administration or local administration. In various embodiments the method of administration is selected from the group comprising intravenous, intraarterial, intraperitoneal, intramuscular, intraportal, subcutaneous, direct injection, intratracheal instillation, inhalation, intranasal, pulmonary and administration via pump into the lung. In some embodiments, the method of administration comprises inhalation. In some embodiments, the method of administration comprises intratracheal instillation.

In some embodiments of the provided method for treating a lung disorder, disease or injury in a patient in need thereof, the at least one TLR2 inhibitor and the at least one TLR4 inhibitor are each inhibitor is independently selected from the group consisting of a small organic molecule, a protein, an antibody or fragment thereof, a peptide, a peptidomimetic and a nucleic acid molecule. In some embodiments, at least one inhibitor comprises a nucleic acid molecule. In other embodiments, each inhibitor comprises a nucleic acid molecule. In various embodiments of the provided method for treating a lung disorder, disease or injury in a patient in need thereof, a first nucleic acid molecule is a double-stranded oligonucleotide that binds a nucleotide sequence encoding a TLR2 gene and a second nucleic acid molecule is a double-stranded oligonucleotide that binds a nucleotide sequence encoding a TLR4 gene. In some embodiments, the double-stranded oligonucleotides are linked one to the other in tandem or annealed in RNAistar formation.

In some embodiments of the provided method for treating a lung disorder, disease or injury in a patient in need thereof, the first double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR2; and
(d) a 17 to 40 nucleotide sequence of the sense strand is complementary to the antisense strand;
and the second double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR4; and
(d) a 17 to 40 nucleotide sequence of the sense strand is complementary to the antisense strand.

In various embodiments the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some embodiments, the first double-stranded oligonucleotide and the second double-stranded oligonucleotide are co-administered to the patient in the same formulation. In other embodiments, the first double-stranded oligonucleotide and the second double-stranded oligonucleotide are co-administered to the patient in different formulations. In some embodiments, the first double-stranded oligonucleotide and the second double-stranded oligonucleotide are co-administered to the patient by the same route. In some embodiments, the first double-stranded oligonucleotide and the second double-stranded oligonucleotide are co-administered to the patient by different routes. In various embodiments, the mode of administration of the first double-stranded oligonucleotide and the second double-stranded oligonucleotide to the recipient of the lung transplant is selected from the group comprising: separate, combined, simultaneous and sequential administration.

In some embodiments, the first double-stranded oligonucleotide and the second double-stranded oligonucleotide are formulated for administering to the patient once. In other embodiments, the first double-stranded oligonucleotide and the second double-stranded oligonucleotide are formulated for administering to the patient at least once-a-day. In other embodiments, the first double-stranded oligonucleotide and the second double-stranded oligonucleotide are formulated for multiple administrations to the patient.

In some embodiments of the provided method for treating a lung disorder, disease or injury in a patient in need thereof, at least one double-stranded oligonucleotide comprises a structure (A1):

```
(A1)    5'  (N)x-Z          3' (antisense strand)
        3'  Z'-(N')y-z"     5' (sense strand)
``` wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present is independently 1-5 consecutive nucleotides or unconventional moieties or a combination thereof covalently attached at the 3' terminus of the strand in which it is present.
wherein z" may be present or absent, but if present is a capping moiety covalently attached at the 5' terminus of (N')y; wherein each of x and y is independently an integer between 17 and 40;
wherein the sequence of (N')y is complementary to the sequence of (N)x; and wherein (N)x comprises an antisense sequence to an mRNA selected from an mRNA encoding TLR2 and an mRNA encoding TLR4.

In various embodiments of structure (A1), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of structure (A1), x=y=19.

In some embodiments of structure (A1), (N)x comprises an antisense oligonucleotide selected from the group consisting of oligonucleotides having SEQ ID NOs: 723-1440, 2247-3052, 7076-8312 and 8459-8604 and (N')y comprises a sense strand oligonucleotide selected from the group consisting of oligonucleotides having SEQ ID NOs: 5-722, 1441-2246, 5839-7075 and 8313-8458.

In some embodiments of the provided method for treating a lung disorder, disease or injury in a patient in need thereof, at least one double-stranded compound comprises a structure (A2):

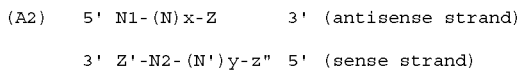

```
(A2)   5'  N1-(N)x-Z      3' (antisense strand)
       3'  Z'-N2-(N')y-z" 5' (sense strand)
``` wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and wherein (N)x is complementary to a consecutive sequence in an mRNA selected from an mRNA encoding TLR2 and an mRNA encoding TLR4;

wherein N1 is covalently bound to (N)x and is mismatched to the mRNA selected from an mRNA encoding TLR2 and an mRNA encoding TLR4;

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In various embodiments of structure (A2), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of structure (A2), x=y=18.

In some embodiments of structure (A2), the sequence of (N)x comprises an antisense oligonucleotide selected from the group consisting of oligonucleotides having SEQ ID NOs: 4153-5252, 5546-5838, 10319-12032, and 12085-12136 and the sequence of (N')y comprises a sense oligonucleotide selected from the group consisting of oligonucleotides having SEQ ID NOs: 3053-4152, 5253-5545, 8605-10318, and 12033-12084.

In another aspect, provided is a composition comprising at least one TLR2 inhibitor or a pharmaceutically acceptable salt or prodrug thereof and at least one TLR4 inhibitor or a pharmaceutically acceptable salt or prodrug thereof; and a pharmaceutically acceptable carrier. In various embodiments, each inhibitor is independently selected from the group consisting of a small organic molecule; a protein, an antibody or fragments thereof, a peptide, a peptidomimetic and a nucleic acid molecule. In some embodiments, each inhibitor is independently selected from the group consisting of a small organic molecule; a protein; an antibody or fragment thereof; and a nucleic acid molecule.

In some embodiments of the provided composition, each inhibitor comprises a nucleic acid molecule. In some embodiments a first nucleic acid molecule is a double-stranded oligonucleotide that binds a nucleotide sequence encoding a TLR2 gene and a second nucleic acid molecule is a double-stranded oligonucleotide that binds a nucleotide sequence encoding a TLR4 gene. In some embodiments of the composition the nucleic acid molecules are linked in tandem or annealed in RNAistar formation.

In some embodiments of the provided composition, a first double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR2; and
(d) a 17 to 40 nucleotide sequence of the sense strand is complementary to the antisense strand;
and a second double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR4; and
(d) a 17 to 40 nucleotide sequence of the sense strand is complementary to the antisense strand.

In various embodiments the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some embodiments, the amount of each double-stranded oligonucleotide in the composition independently ranges from about 0.05 mg to about 10.0 mg.

In some embodiments of the provided composition, at least one double-stranded oligonucleotide independently comprises a structure (A1):

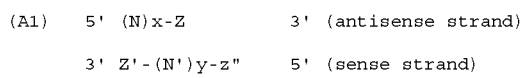

```
(A1)   5' (N)x-Z       3' (antisense strand)
       3' Z'-(N')y-z"  5' (sense strand)
``` wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present is independently 1-5 consecutive nucleotides or unconventional moieties or a combination thereof covalently attached at the 3' terminus of the strand in which it is present.

wherein z" may be present or absent, but if present is a capping moiety covalently attached at the 5' terminus of (N')y;

wherein each of x and y is independently an integer between 17 and 40;

wherein the sequence of (N')y is complementary to the sequence of (N)x; and wherein (N)x comprises an antisense sequence to an mRNA selected from an mRNA encoding TLR2 and an mRNA encoding TLR4.

In various embodiments of the composition, in structure (A1), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of the composition, in structure (A1), x=y=19.

In some embodiments of the composition, at least one double-stranded oligonucleotide compound independently comprises a structure (A2):

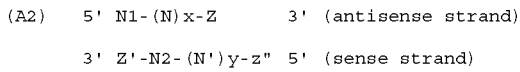

```
(A2)    5'  N1-(N)x-Z        3'  (antisense strand)

3'  Z'-N2-(N')y-z"   5'  (sense strand)
``` wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and (N)x is complementary to a consecutive sequence in an mRNA selected from an mRNA encoding TLR2 and an mRNA encoding TLR4;

wherein N1 is covalently bound to (N)x and is mismatched to an mRNA selected from an mRNA encoding TLR2 and an mRNA encoding TLR4;

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In various embodiments of the provided composition, in structure (A2), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of the provided composition, in structure (A2), x=y=18.

In some embodiments, the provided composition is formulated for administering to the recipient once. In other embodiments, the provided composition is formulated for administering to the recipient at least once-a-day. In yet other embodiments, the provided composition is formulated for multiple administrations to the recipient.

In another aspect, provided is a kit comprising at least two therapeutic agents, wherein at least one agent comprises a TLR2 inhibitor and a second agent comprises a TLR4 inhibitor; optionally with instructions for use.

In some embodiments of the provided kit, each therapeutic agent is independently selected from the group consisting of a small organic molecule, a protein, an antibody or fragment thereof, a peptide, a peptidomimetic and nucleic acid molecule. In some embodiments of the kit, at least one therapeutic agent comprises a nucleic acid molecule. In other embodiments of the provided kit, each therapeutic agent comprises a nucleic acid molecule.

In some embodiments of the provided kit, a first nucleic acid molecule is a double-stranded oligonucleotide that binds a nucleotide sequence encoding a TLR2 gene and a second nucleic acid molecule is a double-stranded oligonucleotide that binds a nucleotide sequence encoding a TLR4 gene. In some embodiments of the, the double stranded oligonucleotides are linked one to the other in tandem or annealed in RNAistar formation.

In some embodiments of the provided kit, the first double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR24; and
(d) a 17 to 40 nucleotide sequence of the sense strand is complementary to the antisense strand;

and the second double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR4; and
(d) a 17 to 40 nucleotide sequence of the sense strand is complementary to the antisense strand.

In various embodiments of the provided kit, the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some embodiments of the kit, the first double-stranded oligonucleotide and the second double-stranded oligonucleotide are formulated for co-administration to a recipient in the same formulation. In other embodiments, the first double-stranded oligonucleotide and the second double-stranded oligonucleotide are co-administered to the patient in different formulations. In some embodiments, the first double-stranded oligonucleotide and the second double-stranded oligonucleotide are co-administered to the patient by the same route. In some embodiments, the first double-stranded oligonucleotide and the second double-stranded oligonucleotide are co-administered to the patient by different routes. In various embodiments, the mode of administration of the first double-stranded oligonucleotide and the second double-stranded oligonucleotide to the recipient of the lung transplant is selected from the group comprising: separate, combined, simultaneous and sequential administration.

In some embodiments of the provided kit, the first double-stranded oligonucleotide and the second double-stranded oligonucleotide are formulated for administering to the patient once. In other embodiments, the first double-stranded oligonucleotide and the second double-stranded oligonucleotide are formulated for administering to the patient at least once-a-day. In other embodiments, the first double-stranded oligonucleotide and the second double-stranded oligonucleotide are formulated for multiple administrations to the patient.

In some embodiments of the provided kit, at least one double-stranded oligonucleotide independently comprises a structure (A1):

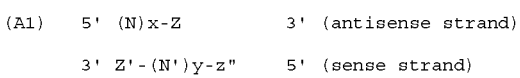

```
(A1)    5'  (N)x-Z          3'  (antisense strand)

3'  Z'-(N')y-z"     5'  (sense strand)
``` wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present is independently 1-5 consecutive nucleotides or unconventional moieties or a combination thereof covalently attached at the 3' terminus of the strand in which it is present.

wherein z" may be present or absent, but if present is a capping moiety covalently attached at the 5' terminus of (N')y;

wherein each of x and y is independently an integer between 17 and 40;

wherein the sequence of (N')y is complementary to the sequence of (N)x; and wherein (N)x comprises an antisense sequence to an mRNA selected from an mRNA encoding TLR2 and an mRNA encoding TLR4.

In various embodiments of the provided kit, in structure (A1), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of the provided kit, in structure (A1), x=y=19.

In some embodiments of the provided kit, at least one double-stranded oligonucleotide independently comprises a structure (A2):

```
(A2)   5' N1-(N)x-Z      3'  (antisense strand)

3' Z'-N2-(N')y-z" 5'  (sense strand)
``` wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and (N)x is complementary to a consecutive sequence in an mRNA selected from an mRNA encoding TLR2 and an mRNA encoding TLR4;

wherein N1 is covalently bound to (N)x and is mismatched to an mRNA selected from an mRNA encoding TLR2 and an mRNA encoding TLR4;

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In various embodiments of the provided kit, in structure (A2), the mRNA polynucleotide sequence of TLR2 is set forth in SEQ ID NO:1 and the mRNA polynucleotide sequence of TLR4 is set forth in any one of SEQ ID NO:2, SEQ ID NO:3 and SEQ ID NO:4.

In some preferred embodiments of the provided kit, in structure (A2), x=y=18.

In another aspect, provided is a package comprising A) at least two separate dosage units selected from (i) at least one dosage unit comprising a TLR2 inhibitor and (ii) at least one dosage unit comprising a TLR4 inhibitor; and optionally B) a package insert comprising instructions for use of the dosage units.

In various embodiments of the provided package, the TLR2 inhibitor is a double-stranded oligonucleotide that binds a nucleotide sequence encoding a TLR2 gene and the TLR4 inhibitor is a double-stranded oligonucleotide that binds a nucleotide sequence encoding a TLR4 gene.

In some embodiments of the provided package, the TLR2 inhibitor is a double-stranded oligonucleotide comprising:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR2; and
(d) a 17 to 40 nucleotide sequence of the sense strand is complementary to the antisense strand;

and the TLR4 inhibitor is a double-stranded oligonucleotide comprising:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR4; and
(d) a 17 to 40 nucleotide sequence of the sense strand is complementary to the antisense strand.

In some embodiments of the provided package, the dosage units are co-administered to a patient by the same route. In other embodiments of the package, the dosage units are co-administration to a patient by different routes. In various embodiments, the mode of administration of the dosage units is selected from the group comprising: separate, combined, simultaneous and sequential administration.

In some embodiments of the provided package, the dosage units are designed for administering to the patient once. In other embodiments, the dosage units are for administering to the patient at least once-a-day. In other embodiments, the dosage units are for multiple administrations to the patient.

In some embodiments of the provided package, at least one double-stranded oligonucleotide independently comprises a structure (A1):

```
(A1)   5' (N)x-Z      3'  (antisense strand)

3' Z'-(N')y-z" 5'  (sense strand)
``` wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present is independently 1-5 consecutive nucleotides or unconventional moieties or a combination thereof covalently attached at the 3' terminus of the strand in which it is present.

wherein z" may be present or absent, but if present is a capping moiety covalently attached at the 5' terminus of (N')y;

wherein each of x and y is independently an integer between 17 and 40;

wherein the sequence of (N')y is complementary to the sequence of (N)x; and wherein (N)x comprises an antisense sequence to an mRNA selected from an mRNA encoding TLR2 and an mRNA encoding TLR4.

In some embodiments of the provided package, at least one double-stranded oligonucleotide independently comprises a structure (A2):

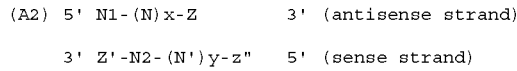

wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and (N)x is complementary to a consecutive sequence in an mRNA selected from an mRNA encoding TLR2 and an mRNA encoding TLR4;

wherein N1 is covalently bound to (N)x and is mismatched to an mRNA selected from an mRNA encoding TLR2 and an mRNA encoding TLR4;

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In various embodiments of the provided kit or the provided package, the instructions or package insert indicates that the therapeutic agents or dosage units are suitable for use in treating a patient suffering from a lung disease, injury or disorder selected from the group consisting of acute respiratory distress syndrome (ARDS), acute lung injury, pulmonary fibrosis (idiopathic), bleomycin induced pulmonary fibrosis, mechanical ventilation induced lung injury, chronic obstructive pulmonary disease (COPD), chronic bronchitis, a disorder associated with lung transplantation and emphysema. In some embodiments of the provided kit or the provided package, the instructions or package insert indicate that the therapeutic agents or dosage units are suitable for use in treating a patient suffering from a disorder associated with lung transplantation.

In some embodiments of the provided kit or the provided package, the lung disorder associated with lung transplantation is selected from the group consisting of inflammation, graft rejection, primary graft failure, ischemia-reperfusion injury, reperfusion injury, reperfusion edema, allograft dysfunction, acute graft dysfunction, pulmonary reimplantation response, bronchiolitis obliterans and primary graft dysfunction (PGD).

In another aspect, provided is a method of preventing or reducing the symptoms of primary graft dysfunction (PGD) in a recipient of a lung transplant, comprising administering to the recipient a therapeutically-effective amount of at least one TLR2 inhibitor or a pharmaceutically acceptable salt or prodrug thereof, thereby preventing or reducing the symptoms of PGD in the recipient.

In some embodiments of the provided method, the recipient of a lung transplant is a human that is being treated for primary graft dysfunction (PGD). In some embodiments, the method is for preventing or reducing the symptoms of cold ischemia-associated PGD. In other embodiments the method is for preventing or reducing the symptoms of warm ischemia-associated PGD. In various embodiments of the provided method, the symptoms are selected from the group consisting of inflammation, acute graft rejection, graft rejection, ischemia-reperfusion injury, reperfusion injury, impaired pulmonary function, bronchiolitis obliterans, impaired blood oxygenation, increased inflammatory cytokine production, intra-graft and intra-airway accumulation of granulocytes, pulmonary edema and hypoxemia.

In some embodiments of the provided method, the administration of a therapeutically-effective amount of at least one TLR2 inhibitor or a pharmaceutically acceptable salt or prodrug thereof, results in one or more of the following: reduced pulmonary edema, increased blood oxygenation, preserved blood oxygenation, improved pulmonary function, preserved pulmonary function in the recipient of a lung transplant and improved pulmonary function of the transplanted lung.

In various embodiments of the provided method, the at least one TLR2 inhibitor is administered to the recipient of a lung transplant prior to, during or following the lung transplantation.

In various embodiments the provided method of preventing or reducing the symptoms of primary graft dysfunction (PGD) in a recipient of a lung transplant, further comprises at least one additional treatment selected from the group consisting of surgery, steroid therapy, non-steroid therapy, antiviral therapy, antifungal therapy, antimicrobial therapy, immunosuppressant therapy, anti-infective therapy, anti-hypertensive therapy, nutritional supplements and any combination thereof. In various embodiments, the additional treatment is administered prior to, subsequent to or concomitantly with administering of at least one TLR2 inhibitor. In some embodiments, the additional treatment comprises immunosuppressant therapy.

In various embodiments of the provided method, the route of administration of at least one TLR2 inhibitor is selected from: systemic administration or local administration.

In various embodiments, the method of administration of at least one TLR2 inhibitor to the recipient of a lung transplant is selected from the group comprising: intravenous, intraarterial, intraperitoneal, intramuscular, intraportal, subcutaneous, direct injection, intratracheal instillation, inhalation, intranasal, pulmonary and administration via pump into the lung. In some embodiments, at least one TLR2 inhibitor is administered to the recipient of a lung transplant by inhalation. In another embodiments, at least one TLR2 inhibitor is administered to the recipient of a lung transplant by intratracheal instillation.

In various embodiments of the provided method of preventing or reducing the symptoms of primary graft dysfunction (PGD) in a recipient of a lung transplant, the at least one TLR2 inhibitor is selected from the group consisting of a small organic molecule, a protein, an antibody or fragment thereof, a peptide, a peptidomimetic and a nucleic acid molecule. In some embodiments, at least one inhibitor comprises a nucleic acid molecule. In some embodiments, the nucleic acid molecule is a double-stranded oligonucleotide that binds a nucleotide sequence encoding a TLR2 gene.

In various embodiments of the provided method of preventing or reducing the symptoms of primary graft dysfunction (PGD) in a recipient of a lung transplant, the double-stranded oligonucleotide comprises:
  (a) a sense strand and an antisense strand;
  (b) each strand is independently 17 to 40 nucleotides in length;
  (c) a 17 to 40 nucleotide sequence of the antisense strand is complementary to a sequence of an mRNA encoding TLR2; and
  (d) a 17 to 40 nucleotide sequence of the sense strand is complementary to the antisense strand.

In various embodiments of the provided method, the double-stranded oligonucleotide is formulated for administering to the recipient once. In some embodiments of the provided method, the double-stranded oligonucleotide is formulated for administering to the recipient at least once-a-day. In yet other embodiments, the double-stranded oligonucleotide is formulated for multiple administrations to the recipient.

In various embodiments of the provided method, the double-stranded oligonucleotide comprises a structure (A1):

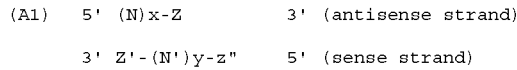

wherein each of N and N' is a ribonucleotide which may be unmodified or modified, or an unconventional moiety;
wherein each of (N)x and (N')y is an oligonucleotide in which each consecutive N or N' is joined to the next N or N' by a covalent bond;
wherein each of Z and Z' is independently present or absent, but if present is independently 1-5 consecutive nucleotides or unconventional moieties or a combination thereof covalently attached at the 3' terminus of the strand in which it is present.
wherein z" may be present or absent, but if present is a capping moiety covalently attached at the 5' terminus of (N')y; wherein each of x and y is independently an integer between 17 and 40;
wherein the sequence of (N')y is complementary to the sequence of (N)x; and wherein (N)x comprises an antisense sequence to an mRNA encoding TLR2.

In various embodiments of the provided method, in structure (A1), the mRNA polynucleotide sequence of TLR2 is set forth in SEQ ID NO:1.

In some preferred embodiments of the provided method, in structure (A1), x=y=19.

In various embodiments of the provided method, in structure (A1), (N)x comprises an antisense oligonucleotide present in SEQ ID NOs: 723-1440 and 2247-3052 and (N')y comprises a sense strand oligonucleotide present in SEQ ID NOs: 5-722 and 1441-2246.

In various embodiments of the provided method, the double-stranded compound comprises a structure (A2):

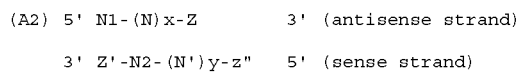

wherein each of N2, N and N' is independently an unmodified or modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein the sequence of (N')y is complementary to the sequence of (N)x and wherein (N)x is complementary to a consecutive sequence in an mRNA encoding TLR2;
wherein N1 is covalently bound to (N)x and is mismatched to the mRNA encoding TLR2;
wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine,
wherein z" may be present or absent, but if present is a capping moiety covalently attached at the 5' terminus of N2-(N')y; and
wherein each of Z and Z' is independently present or absent, but if present is independently 1-5 consecutive nucleotides or unconventional moieties or a combination thereof covalently attached at the 3' terminus of the strand in which it is present.

In various embodiments of the provided method, in structure (A2), the mRNA polynucleotide sequence of TLR2 is set forth in SEQ ID NO:1

In some preferred embodiments of the provided method, in structure (A2), x=y=18.

In various embodiments of the provided method, in structure (A2), the sequence of (N)x is selected from anyone of SEQ ID NOs: 4153-5252 and 5546-5838 and the sequence of (N')y is selected from anyone of SEQ ID NOs: 3053-4152 and 5253-5545.

In various embodiments of the provided method, administration of the at least one double-stranded oligonucleotide that binds a nucleotide sequence encoding a TLR2 gene results in down-regulation of TLR2 expression.

In another aspect provided is a kit or package comprising at least one dosage unit comprising a TLR2 inhibitor; optionally with instructions for use, wherein the instructions indicate that the dosage unit is suitable for use in treating a patient suffering from a lung disease, injury or disorder selected from the group consisting of respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, a disorder associated with lung transplantation and emphysema.

In some embodiments the provided kit or package are for use in treating a patient suffering from a disorder associated with lung transplantation.

In various embodiments of the provided kit or package, the TLR2 inhibitor is selected from the group consisting of a small organic molecule, a protein, an antibody or fragment thereof, a peptide, a peptidomimetic and nucleic acid molecule. In some embodiments of the kit or package, the TLR2 inhibitor is selected from the group consisting of a small organic molecule, a protein; an antibody or fragment thereof; and a nucleic acid molecule. In other embodiments of the kit or package, the TLR2 inhibitor comprises a nucleic acid molecule.

In some embodiments of the provided kit or package, the nucleic acid molecule is a double-stranded oligonucleotide that binds a nucleotide sequence encoding a TLR2 gene. In some embodiments of the kit or package, the double-stranded oligonucleotide comprises:
- (a) a sense strand and an antisense strand;
- (b) each strand is independently 17 to 40 nucleotides in length;
- (c) a 17 to 40 nucleotide sequence of the antisense strand is complementary to a sequence of an mRNA encoding TLR2; and
- (d) a 17 to 40 nucleotide sequence of the sense strand is complementary to the antisense strand.

In some embodiments of the provided kit or package, the double-stranded oligonucleotide is formulated for administering to the patient once. In some embodiments, the double-stranded oligonucleotide is formulated for administering to the patient at least once-a-day. In some embodiments of the provided kit or package, the double-stranded oligonucleotide is formulated for multiple administrations to the patient.

In some embodiments of the provided kit or package, the double-stranded oligonucleotide comprises a structure (A1):

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present is independently 1-5 consecutive nucleotides or unconventional moieties or a combination thereof covalently attached at the 3' terminus of the strand in which it is present.

wherein z" may be present or absent, but if present is a capping moiety covalently attached at the 5' terminus of (N')y;

wherein each of x and y is independently an integer between 17 and 40;

wherein the sequence of (N')y is complementary to the sequence of (N)x; and wherein (N)x comprises an antisense sequence to an mRNA encoding TLR2.

In some embodiments of the provided kit or package, the double-stranded oligonucleotide comprises a structure (A2):

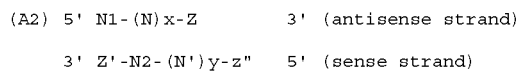

wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and (N)x is complementary to a consecutive sequence in an mRNA encoding TLR2;

wherein N1 is covalently bound to (N)x and is mismatched to an mRNA encoding TLR2;

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In some embodiments, the provided kit or package is for use in treating a patient suffering from a disorder associated with lung transplantation. In various embodiments the disorder associated with lung transplantation is selected from the group consisting of inflammation, graft rejection, primary graft failure, ischemia-reperfusion injury, reperfusion injury, reperfusion edema, allograft dysfunction, acute graft dysfunction, pulmonary reimplantation response, bronchiolitis obliterans and primary graft dysfunction (PGD).

In another aspect provided is a use of a composition comprising at least one TLR2 inhibitor or a pharmaceutically acceptable salt or prodrug thereof and at least one TLR4 inhibitor or a pharmaceutically acceptable salt or prodrug thereof; and a pharmaceutically acceptable carrier, for the preparation of a medicament for treating or preventing or reducing the symptoms of primary graft dysfunction (PGD) in a recipient of a lung transplant.

In another aspect provided is a use of a composition comprising at least one TLR2 inhibitor or a pharmaceutically acceptable salt or prodrug thereof and at least one TLR4 inhibitor or a pharmaceutically acceptable salt or prodrug thereof; and a pharmaceutically acceptable carrier, for treating or preventing or reducing the symptoms of primary graft dysfunction (PGD) in a recipient of a lung transplant.

In various embodiments of the provided use, the recipient of a lung transplant is a human that is being treated for primary graft dysfunction (PGD). In some embodiments, the use is for preventing or reducing the symptoms of cold ischemia-associated PGD. In other embodiments, the use is for preventing or reducing the symptoms of warm ischemia-associated PGD.

In various embodiments of the use, the symptoms are selected from the group consisting of inflammation, acute graft rejection, graft rejection, ischemia-reperfusion injury, reperfusion injury, impaired pulmonary function, bronchiolitis obliterans, impaired blood oxygenation, increased inflammatory cytokine production, intra-graft and intra-airway accumulation of granulocytes, pulmonary edema and hypoxemia.

In another aspect provided is a use of a composition comprising at least one TLR2 inhibitor or a pharmaceutically acceptable salt or prodrug thereof and at least one TLR4 inhibitor or a pharmaceutically acceptable salt or prodrug thereof; and a pharmaceutically acceptable carrier, for the preparation of a medicament for treating or preventing a lung disease, disorder or injury selected from acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, and emphysema.

In another aspect provided is a use of a composition comprising at least one TLR2 inhibitor or a pharmaceutically acceptable salt or prodrug thereof and at least one TLR4 inhibitor or a pharmaceutically acceptable salt or prodrug thereof; and a pharmaceutically acceptable carrier, for treating or preventing a lung disease, disorder or injury selected from acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, and emphysema.

DETAILED DESCRIPTION OF THE INVENTION

Figure 1:
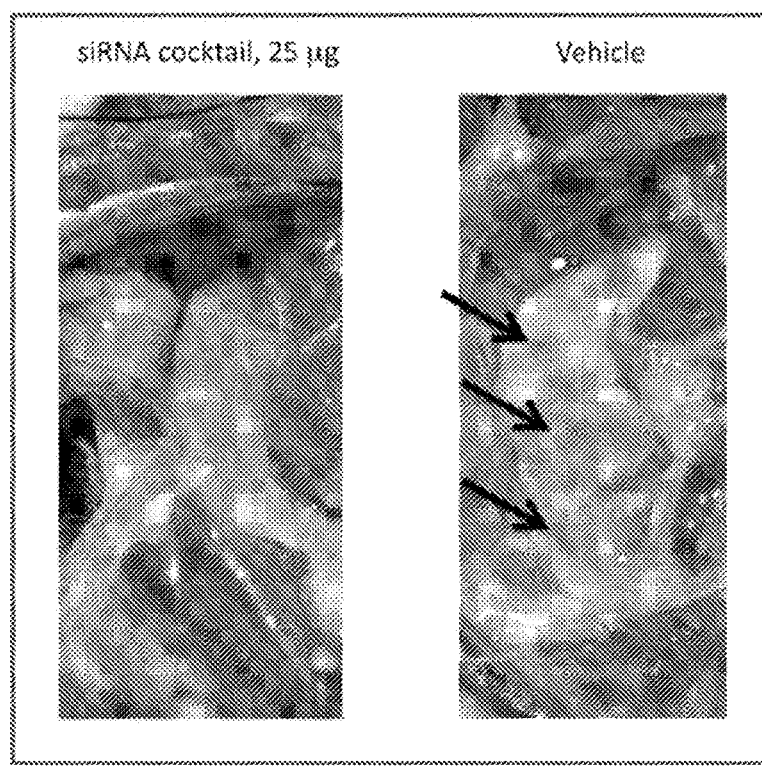
FIG. 1 shows that combined administration of a double-stranded RNA (dsRNA) specific for TLR2, at a dose of 25 μg/mouse and a double-stranded RNA (dsRNA) specific for TLR4, at a dose of 25 μg/mouse efficiently reduced post-transplantation lung edema and hemorrhages in the transplanted mouse lung. Photographs of the recipient's lung were taken at 24 hours after orthotopic lung transplantation. Left: dsRNA combination (combination of dsRNA specific for TLR2 and dsRNA specific for TLR4, each at 25 μg/mouse (identified in the figure as "siRNA cocktail, 25 μg")) was administered at the end of lung transplantation surgery (immediately after anastomosis opening), by intratracheal instillation to the recipient. Right: vehicle. Arrows: prominent hemorrhages.

The present disclosures relate in part to a method for treating a lung disorder, disease or injury in a mammal in need thereof. The method may include administering to the mammal at least one therapeutic agents selected from a TLR2 inhibitor or a pharmaceutically acceptable salt or prodrug thereof; in an amount effective to treat the mammal. The method may include administering to the mammal at least two therapeutic agents wherein at least one therapeutic agent targets the TLR2 gene or gene product and at least one therapeutic agent targets the TLR4 gene or gene product. In some embodiments the therapeutic agents include: (i) a TLR2 inhibitor or a pharmaceutically acceptable salt or prodrug thereof, and (ii) a TLR4 inhibitor or a pharmaceutically acceptable salt or prodrug thereof; in amounts effective to treat the lung disorder, disease or injury in the mammal. The present disclosures also relate to combinations, compositions, kits and packages that include the therapeutic agents.

In some embodiments, methods may include administering to the mammal at least one therapeutic agents in an amount sufficient to reduce expression and/or to inhibit function of TLR2 gene. In some embodiments methods may include administering to the mammal a combination of at least two therapeutic agents or a combined therapeutic agent in an amount sufficient to reduce expression and/or to inhibit function of both a TLR2 gene and a TLR4 gene. In certain embodiments the lung disease or injury is selected from the group consisting of acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema, lung transplantation-induced acute graft dysfunction and bronchiolitis obliterans after lung transplantation. In certain embodiments, provided are compositions and methods for combination therapy for treating or preventing inflammation and/ or graft rejection associated with organ transplantation, in particular lung transplantation, including treatment, prevention or attenuation of progression of primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD) after organ transplantation, in particular in lung transplantation.

In some embodiments the at least one therapeutic agent is a TLR2 inhibitor. In some embodiments the at least two therapeutic agents are a TLR2 inhibitor and a TLR4 inhibitor. In some embodiments the at least two therapeutic agents are co-administered, e.g. concomitantly or in sequence. In other embodiments, the at least two therapeutic agents are administered in a pharmaceutical composition comprising a combination thereof. In some embodiments the therapeutic agent is a combined inhibitor by which it is meant a single agent which is capable of down-regulating the expression and/or activity of both gene TLR2 and gene TLR4 and/or gene products thereof. Non-limiting examples of such single agents are tandem and multi-armed RNAi molecules disclosed in PCT Patent Publication No. WO 2007/091269.

In one embodiment the method comprises administering a therapeutically effective amount of a therapeutic agent, which targets TLR2.

In some embodiments the method comprises administering (a) a therapeutically effective amount of a first therapeutic agent, which targets TLR2 and (b) a therapeutically effective amount of a second therapeutic agent, which targets TLR4.

In one embodiment the method comprises administering a therapeutically effective amount of a combined inhibitor, which targets both TLR2 and TLR4.

In some embodiments the therapeutic agent is a TLR2 inhibitor. In some embodiments the therapeutic agent is selected from the group consisting of a small organic molecule chemical compound; a protein; an antibody or fragment thereof; a peptide; a peptidomimetic and a nucleic acid molecule. In some embodiments at least one therapeutic agent is a nucleic acid molecule. In some embodiments the therapeutic agent comprises a nucleic acid molecule. In some embodiments the nucleic acid molecule is independently selected from the group consisting of an antisense molecule, a short interfering nucleic acid (siNA), short interfering RNA (siRNA), double-stranded RNA (dsRNA), micro-RNA (miRNA) or short hairpin RNA (shRNA) that bind a nucleotide sequence (such as an mRNA sequence) encoding the gene TLR2, for example the mRNA coding sequence for human TLR2 exemplified by SEQ ID NO:1 (gi|68160956|ref|NM_003264.3|).

In some embodiments the at least two therapeutic agents are a TLR2 inhibitor and a TLR4 inhibitor. In some embodiments each therapeutic agent is independently selected from the group consisting of a small organic molecule; a protein; an antibody or fragment thereof; a peptide; a peptidomimetic and a nucleic acid molecule. In some embodiments at least one therapeutic agent is a nucleic acid molecule. In some embodiments each therapeutic agent comprises a nucleic acid molecule.

In some embodiments each nucleic acid molecule is independently selected from the group consisting of an antisense molecule, a short interfering nucleic acid (siNA), short interfering RNA (siRNA), double-stranded RNA (dsRNA), micro-RNA (miRNA) or short hairpin RNA (shRNA) that bind a nucleotide sequence (such as an mRNA sequence) encoding a target gene selected from TLR2 and TLR4, for example: the mRNA coding sequence for human TLR2 exemplified by SEQ ID NO:1 or the mRNA coding sequence for human TLR4 exemplified by SEQ ID NOs:2-4.

In various embodiments each nucleic acid molecule is a dsRNA molecule or a siRNA molecule.

In various embodiments each therapeutic agent comprises a nucleic acid molecule, wherein:
(a) the nucleic acid molecule includes a sense strand and an antisense strand;
(b) each strand of the nucleic acid molecule is independently 17 to 40 nucleotides in length;
(c) a 17 to 40 nucleotide sequence of the antisense strand is complementary to a sequence of an mRNA selected from an mRNA encoding TLR2 (e.g., SEQ ID NO: 1) or an mRNA encoding TLR4 (e.g., SEQ ID NOs: 2-4); and
(d) a 17 to 40 nucleotide sequence of the sense strand is complementary to the antisense strand and includes a 17 to 40 nucleotide sequence of a mRNA selected from a mRNA encoding TLR2 (e.g., SEQ ID NO: 1) and an mRNA encoding TLR4 (e.g., SEQ ID NOs: 2-4).

In various embodiments each therapeutic agent comprises a nucleic acid molecule having a structure (A1):

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present is independently 1-5 consecutive nucleotides or unconventional moieties or a combination thereof covalently attached at the 3' terminus of the strand in which it is present.

wherein z" may be present or absent, but if present is a capping moiety covalently attached at the 5' terminus of (N')y;

wherein each of x and y is independently an integer between 17 and 40;

wherein the sequence of (N')y is complementary to the sequence of (N)x; and wherein (N)x comprises an antisense sequence to an mRNA selected from an mRNA encoding TLR2 and an mRNA encoding TLR4.

In some embodiments the sequence of TLR2 mRNA is set forth in SEQ ID NO:1. In various embodiments the sense and antisense strands of the TLR2 siRNA oligonucleotides are selected from the sense strand sequences set forth in SEQ ID NOs: 5-722; 1441-2246; 3053-4152; and 5253-5545 and antisense strand sequences set forth in SEQ ID NOs: 723-1440; 2247-3052; 4153-5252 and 5546-5838. In some embodiments the sequence of TLR4 mRNA is set forth in SEQ ID NO:2; SEQ ID NO:3 or SEQ ID NO:4. In various embodiments the sense and antisense strands of the TLR4 siRNA oligonucleotides are selected from the sense strand sequences set forth in SEQ ID NOs: 5839-7075, 8313-8458, 8605-10318, 12033-12084 and antisense strand sequences set forth in SEQ ID NOs: 7076-8312, 8459-8604, 10319-12032, 12085-12136.

In some embodiments (N)x of the double-stranded oligonucleotide compound comprises an antisense oligonucleotide present in SEQ ID NOs: 723-1440, 2247-3052, 4153-5252, 5546-5838, 7076-8312, 8459-8604, 10319-12032, 12085-12136. In some embodiments the sequence of (N')y is partially complementary to the sequence of (N)x. In some embodiments the sequence of (N')y is substantially complementary to the sequence of (N)x. In some embodiments the sequence of (N')y is fully complementary to the sequence of (N)x. In some embodiments (N)x of the double-stranded oligonucleotide compound comprises an antisense oligonucleotide present in double-stranded RNA compounds identified as TLR2_4, TLR2_7 or TLR4_4.

In some embodiments of the double-stranded oligonucleotide compound x=y=19. In various embodiments both Z and Z' are present in the double-stranded oligonucleotide compound. In various embodiments both Z and Z' are absent in the double-stranded oligonucleotide compound; i.e. the double-stranded compound is blunt ended on both ends. In some embodiments at least one of Z or Z' is present in said double-stranded oligonucleotide compound.

In some embodiments Z or Z' is independently an unconventional moiety selected from an abasic deoxyribose moiety, an abasic ribose moiety an inverted abasic deoxyribose moiety, an inverted abasic ribose moiety; a C3 moiety, a C4 moiety, a C5 moiety, an amino-6 moiety. In some preferred embodiments Z or Z' is independently selected from a C3 moiety and an amino-C6 moiety.

In some embodiments at least one of N or N' in the double-stranded oligonucleotide compound comprises a 2' sugar modified ribonucleotide. In some embodiments the 2' sugar modification comprises the presence of an amino, a fluoro, an alkoxy or an alkyl moiety. In some preferred embodiments 2' sugar modification comprises the presence of an alkoxy moiety, preferably the alkoxy moiety comprises a 2'-O-Methyl moiety.

In some embodiments of the double-stranded oligonucleotide compound, (N)x comprises alternating 2'-O-Methyl sugar modified ribonucleotides and unmodified ribonucleotides. In certain embodiments, (N)x comprises at least 5 alternating 2'-O-Methyl sugar modified and unmodified ribonucleotides. In some embodiments, (N)x comprises 2'-O-Methyl sugar modified ribonucleotides at positions 2, 4, 6, 8, 11, 13, 15, 17 and 19. In some embodiments, (N)x comprises 2'-O-Methyl sugar modified ribonucleotides at positions 1, 3, 5, 7, 9, 11, 13, 15, 17 and 19. In some embodiments, (N)x comprises 2'-O-Methyl sugar modified pyrimidine ribonucleotides. In some embodiments, all pyrimidine ribonucleotides in (N)x comprise 2'-O-Methyl sugar modified pyrimidine ribonucleotides.

In some embodiments, (N)x comprises at least one unconventional moiety selected from a mirror nucleotide and a nucleotide joined to an adjacent nucleotide by a 2'-5' internucleotide phosphate bond. In some embodiments, the unconventional moiety in (N)x is a mirror nucleotide. In some embodiments, the mirror nucleotide in (N)x is an L-deoxyribonucleotide (L-DNA). In various embodiments, (N)x comprises an L-DNA moiety at position 6 or 7 (5'>3').

In some embodiments, (N')y comprises at least one unconventional moiety selected from a mirror nucleotide and a nucleotide joined to an adjacent nucleotide by a 2'-5' internucleotide phosphate bond. In some embodiments, the unconventional moiety in (N')y is a mirror nucleotide. In some embodiments, the mirror nucleotide in (N')y is an L-deoxyribonucleotide (L-DNA). In some embodiments, (N')y consists of unmodified ribonucleotides at positions 1-17 and 19 and one L-DNA at the 3' penultimate position (position 18). In some embodiments, (N')y consists of unmodified ribonucleotides at position 1-16 and 19 and two consecutive L-DNA at the 3' penultimate positions (positions 17 and 18). In some embodiments the unconventional moiety in (N')y is a nucleotide joined to an adjacent nucleotide by a 2'-5' internucleotide phosphate linkage. In some embodiments, in (N')y the nucleotide joined to an adjacent nucleotide by a 2'-5' internucleotide phosphate linkage further comprises a 3'-O-Methyl (3'O-Me) sugar modification.

In various embodiments the therapeutic agent is a double-stranded oligonucleotide compound having a structure (A2) set forth below:

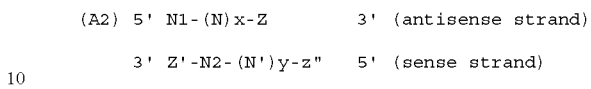

wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and (N)x is complementary to a consecutive sequence in an mRNA selected from an mRNA encoding TLR2 (e.g., SEQ ID NO: 1) and an mRNA encoding TLR4 (e.g., SEQ ID NOs: 2-4);

wherein N1 is covalently bound to (N)x and is mismatched to an mRNA selected from an mRNA encoding TLR2 (e.g., SEQ ID NO: 1) and an mRNA encoding TLR4 (e.g., SEQ ID NOs: 2-4);

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In some embodiments of the double-stranded oligonucleotide compound according to Structure (A)2, x=y=18.

In some embodiments (N)x is complementary to a consecutive sequence in SEQ ID NO:1 (human TLR2 mRNA). In some embodiments (N)x includes an antisense oligonucleotide selected from any one of SEQ ID NOs: 4153-5252 and 5546-5838. In some embodiments x=y=18 and N1-(N)x includes an antisense oligonucleotide selected from any one of SEQ ID NOs: 723-1440 and 2247-3052. In some embodiments x=y=19 or x=y=20. In certain preferred embodiments x=y=18.

In some embodiments (N)x is complementary to a consecutive sequence in SEQ ID NO:2 (human TLR4, transcript variant 4, non-coding RNA) or SEQ ID NO:3 (human TLR4, transcript variant 1, mRNA) or SEQ ID NO:4 (human TLR4, transcript variant 3, non-coding RNA). In some embodiments (N)x includes an antisense oligonucleotide selected from any one of SEQ ID NOs: 10319-12032 and 12085-12136. In some embodiments x=y=18 and N1-(N)x includes an antisense oligonucleotide selected from any one of SEQ ID NOs: 7076-8312 and 8459-8604. In some embodiments x=y=19 or x=y=20. In certain preferred embodiments x=y=18.

In some embodiments N1 and N2 form a Watson-Crick base pair. In other embodiments N1 and N2 form a non-Watson-Crick base pair. In some embodiments N1 is a modified riboadenosine or a modified ribouridine.

In certain embodiments N1 is selected from the group consisting of riboadenosine, modified riboadenosine, deoxyriboadenosine, modified deoxyriboadenosine. In other embodiments N1 is selected from the group consisting of ribouridine, deoxyribouridine, modified ribouridine, and modified deoxyribouridine.

In certain embodiments, N1 is selected from the group consisting of riboadenosine, modified riboadenosine, deoxyriboadenosine, modified deoxyriboadenosine and N2 is selected from the group consisting of ribouridine, deoxyribouridine, modified ribouridine, and modified deoxyribouridine. In certain embodiments N1 is selected from the group consisting of riboadenosine and modified riboadenosine and N2 is selected from the group consisting of ribouridine and modified ribouridine.

In certain embodiments, N2 is selected from the group consisting of riboadenosine, modified riboadenosine, deoxyriboadenosine, modified deoxyriboadenosine and N1 is selected from the group consisting of ribouridine, deoxyribouridine, modified ribouridine, and modified deoxyribouridine. In certain embodiments, N1 is selected from the group consisting of ribouridine and modified ribouridine and N2 is selected from the group consisting of riboadenine and modified riboadenine. In certain embodiments, N1 is ribouridine and N2 is riboadenine.

In some embodiments of (A2), (N)x is selected from any one of SEQ ID NOs: 4153-5252 and 5546-5838 and (N')y is a substantially complementary sequence selected from SEQ ID NOs: 3053-4152 and 5253-5545. In some embodiments of (A2), (N)x is selected from any one of SEQ ID NOs: 10319-12032 and 12085-12136 and (N')y is a substantially complementary sequence selected from SEQ ID NOs: 8605-10318 and 12033-12084. In some embodiments the sequence of (N')y is partially complementary to the sequence of (N)x. In some embodiments the sequence of (N')y is fully complementary to the sequence of (N)x. In some embodiments, (N)x of the double-stranded oligonucleotide compound comprises an antisense oligonucleotide present in double-stranded RNA compounds identified as TLR2_4, TLR2_7 or TLR4_4.

In some embodiments, the administration method is systemic administration. In some embodiments, the administration method is local administration. In various embodiments the administration method is intratracheal, inhalant, intravenous, intraarterial, intraperitoneal, intramuscular, intraportal, subcutaneous, intradermal, topical, direct administration into a target lung tissue by injection or via a pump.

In one aspect provided is a pharmaceutical composition that includes at least one therapeutic agent selected from a TLR2 inhibitor or a pharmaceutically acceptable salt or prodrug thereof; and a pharmaceutically acceptable carrier.

In another aspect provided is a combination that includes at least two therapeutic agents selected from: (i) a TLR2 inhibitor or a pharmaceutically acceptable salt or prodrug thereof and (ii) a TLR4 inhibitor or a pharmaceutically acceptable salt or prodrug thereof; and a pharmaceutically acceptable carrier.

In another aspect provided is a pharmaceutical composition that includes a combination of at least two therapeutic agents selected from: (i) a TLR2 inhibitor or a pharmaceutically acceptable salt or prodrug thereof and (iii) a TLR4 inhibitor or a pharmaceutically acceptable salt or prodrug thereof; and a pharmaceutically acceptable carrier.

In some embodiments the composition comprises a therapeutic agent consisting of a TLR2 inhibitor. In some embodiments the combination or composition comprises at least two therapeutic agents, wherein at least one of the therapeutic agents is a TLR2 inhibitor or a pharmaceutically acceptable salt or prodrug thereof, and at least one of the therapeutic agents is a TLR4 inhibitor or a pharmaceutically acceptable salt or prodrug thereof. In some embodiments the combination or composition comprises a TLR2 inhibitor and a TLR4 inhibitor.

In some embodiments the TLR2 inhibitor is selected from the group consisting of a small molecule chemical compound; a protein; an antibody or fragment thereof; and a nucleic acid molecule. In some embodiments the TLR2 inhibitor comprises a nucleic acid molecule. In some embodiments the nucleic acid molecule is selected from a short interfering nucleic acid (siNA), a short interfering RNA (siRNA), a double-stranded RNA (dsRNA), a micro-RNA (miRNA) or short hairpin RNA (shRNA) that binds a nucleotide sequence (such as an mRNA sequence) encoding the target gene TLR2. In some embodiments the nucleic acid molecule is a double-stranded RNA (dsRNA) or a short interfering RNA (siRNA) targeting TLR2.

In some embodiments each therapeutic agent is independently selected from the group consisting of a small molecule chemical compound; a protein; an antibody or fragment thereof; and a nucleic acid molecule. In some embodiments each therapeutic agent comprises a nucleic acid molecule. In some embodiments each nucleic acid molecule is independently selected from a short interfering nucleic acid (siNA), a short interfering RNA (siRNA), a double-stranded RNA (dsRNA), a micro-RNA (miRNA) or short hairpin RNA (shRNA) that binds a nucleotide sequence (such as an mRNA sequence) encoding the target gene selected from TLR2 and TLR4. In some embodiments each nucleic acid molecule is a double-stranded RNA (dsRNA) or a short interfering RNA (siRNA). In some embodiments the at least two dsRNA or siRNA are a dsRNA or siRNA targeting TLR2 and a dsRNA or siRNA targeting TLR4.

In one embodiment the method comprises a therapeutically effective amount of a therapeutic agent, which down-regulates TLR2.

In one embodiment the method comprises (a) a therapeutically effective amount of a first therapeutic agent, which down-regulates TLR2 and (b) a therapeutically effective amount of a second therapeutic agent, which down-regulates TLR4.

In another aspect provided is a kit comprising at a therapeutic agent consisting of a TLR2 inhibitor; optionally with instructions for use.

In another aspect provided is a kit comprising at least two therapeutic agents wherein the two agents are selected from the group consisting of a TLR2 inhibitor and a TLR4 inhibitor; optionally with instructions for use.

In some embodiments of the kit each therapeutic agent is independently selected from the group consisting of a small molecule chemical compound; a protein; an antibody or fragment thereof; and a nucleic acid molecule. In some embodiments each therapeutic agent comprises a nucleic acid molecule. In some embodiments each nucleic acid molecule is independently selected from a short interfering nucleic acid (siNA), a short interfering RNA (siRNA), a double-stranded RNA (dsRNA), a micro-RNA (miRNA) or short hairpin RNA (shRNA) that binds a nucleotide sequence (such as an mRNA sequence) encoding a target gene selected from TLR2 and TLR4. In some embodiments each nucleic acid molecule is a double-stranded RNA (dsRNA) or a short interfering RNA (siRNA). In some embodiments each nucleic acid molecule is selected from the group consisting of a dsRNA targeting TLR2 or a siRNA targeting TLR2; and a dsRNA targeting TLR4 or a siRNA targeting TLR4. In some embodiments the at least two siRNA consist of: a dsRNA or siRNA targeting TLR2; and a dsRNA or siRNA targeting TLR4.

In some embodiments a kit provided herein comprises a combined inhibitor by which it is meant a single agent which is capable of down-regulating at least two genes and/or gene products selected from the group consisting both TLR2 and TLR4; optionally with instructions for use.

In some embodiments each therapeutic agent of the kit comprises a nucleic acid molecule, wherein:

(a) the nucleic acid molecule includes a sense strand and an antisense strand;

(b) each strand of the nucleic acid molecule is independently 17 to 40 nucleotides in length;

(c) a 17 to 40 nucleotide sequence of the antisense strand is complementary to a sequence of an mRNA selected from an mRNA encoding TLR2 (e.g., SEQ ID NO: 1) and an mRNA encoding TLR4 (e.g., SEQ ID NOs: 2-4); and (d) a 17 to 40 nucleotide sequence of the sense strand is complementary to the antisense strand and includes a 17 to 40 nucleotide sequence of a mRNA selected from a mRNA encoding TLR2 (e.g., SEQ ID NO: 1) and an mRNA encoding TLR4 (e.g., SEQ ID NOs: 2-4).

In some embodiments each therapeutic agent of the kit comprises a nucleic acid molecule having a structure (A1):

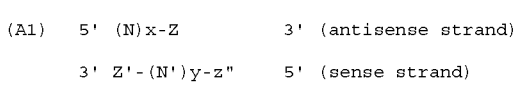

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present is independently 1-5 consecutive nucleotides or unconventional moieties or a combination thereof covalently attached at the 3' terminus of the strand in which it is present.

wherein z" may be present or absent, but if present is a capping moiety covalently attached at the 5' terminus of (N')y;

wherein each of x and y is independently an integer between 17 and 40;

wherein the sequence of (N')y is complementary to the sequence of (N)x; and wherein (N)x comprises an antisense sequence to an mRNA selected from an mRNA encoding TLR2 and an mRNA encoding TLR4.

In various embodiments the double-stranded molecule comprises a mismatch to the target mRNA at the 5' terminal nucleotide of the guide strand (antisense strand). Accordingly, in some embodiments each therapeutic agent of the kit comprises a double-stranded oligonucleotide compound having a structure (A2) set forth below

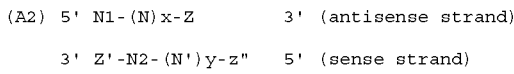

wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and (N)x is complementary to a consecutive sequence in an mRNA selected from an mRNA encoding TLR2 (e.g., SEQ ID NO: 1) and an mRNA encoding TLR4 (e.g., SEQ ID NOs: 2-4);

wherein N1 is covalently bound to (N)x and is mismatched to an mRNA selected from an mRNA encoding TLR2 (e.g., SEQ ID NO: 1) and an mRNA encoding TLR4 (e.g., SEQ ID NOs: 2-4);

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In another aspect provided is a package comprising A) at least two separate dosage units selected from (i) a dosage unit comprising a TLR2 inhibitor, and (ii) a dosage unit comprising a TLR4 inhibitor; and optionally B) a package insert comprising instructions for use of the dosage units.

In another embodiment of the package each inhibitor comprises a nucleic acid molecule, wherein:

(a) the nucleic acid molecule includes a sense strand and an antisense strand;

(b) each strand of the nucleic acid molecule is independently 17 to 40 nucleotides in length;

(c) a 17 to 40 nucleotide sequence of the antisense strand is complementary to a sequence of an mRNA selected from an mRNA encoding TLR2 and an mRNA encoding TLR4; and (d) a 17 to 40 nucleotide sequence of the sense strand is complementary to the antisense strand and includes a 17 to 40 nucleotide sequence of a mRNA selected from an mRNA encoding TLR2 and an mRNA encoding TLR4.

In some embodiments of the package each inhibitor comprises a nucleic acid molecule having a structure (A1):

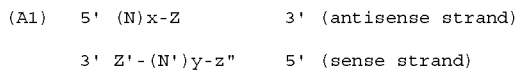

wherein each of N and N' is a ribonucleotide which may be unmodified or modified, or an unconventional moiety;

wherein each of (N)x and (N')y is an oligonucleotide in which each consecutive N or N' is joined to the next N or N' by a covalent bond;

wherein each of Z and Z' is independently present or absent, but if present is independently 1-5 consecutive nucleotides or unconventional moieties or a combination thereof covalently attached at the 3' terminus of the strand in which it is present.

wherein z" may be present or absent, but if present is a capping moiety covalently attached at the 5' terminus of (N')y;

wherein each of x and y is independently an integer between 17 and 40;

wherein the sequence of (N')y is complementary to the sequence of (N)x; and wherein (N)x comprises an antisense sequence to an mRNA selected from an mRNA encoding TLR2 and an mRNA encoding TLR4.

In various embodiments the double-stranded molecule comprises a mismatch to the target mRNA at the 5' terminal nucleotide of the guide strand (antisense strand). Accordingly, in some embodiments of the package each inhibitor comprises a double-stranded oligonucleotide compound having a structure (A2) set forth below:

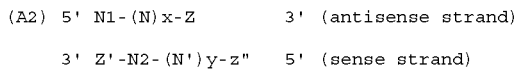

```
(A2)  5' N1-(N)x-Z         3' (antisense strand)

3' Z'-N2-(N')y-z"    5' (sense strand)
``` wherein each of N2, N and N' is independently an unmodified or modified ribonucleotide, or an unconventional moiety;

wherein each of (N)x and (N')y is an oligonucleotide in which each consecutive N or N' is joined to the adjacent N or N' by a covalent bond;

wherein each of x and y is independently an integer between 17 and 39;

wherein the sequence of (N')y is complementary to the sequence of (N)x and (N)x is complementary to a consecutive sequence in an mRNA selected from an mRNA encoding TLR2 and an mRNA encoding TLR4;

wherein N1 is covalently bound to (N)x and is mismatched to an mRNA selected from an mRNA encoding TLR2 and an mRNA encoding TLR4;

wherein N1 is a moiety selected from the group consisting of uridine, modified uridine, ribothymidine, modified ribothymidine, deoxyribothymidine, modified deoxyribothymidine, riboadenine, deoxyriboadenine and modified deoxyriboadenine, wherein z" may be present or absent, but if present is a capping moiety covalently attached at the 5' terminus of N2-(N')y; and wherein each of Z and Z' is independently present or absent, but if present is independently 1-5 consecutive nucleotides or unconventional moieties or a combination thereof covalently attached at the 3' terminus of the strand in which it is present.

In various embodiments of the kit or package the instructions or package insert indicates that the therapeutic agent or dosage unit or the therapeutic agents or dosage units are suitable for use in treating a patient suffering from a disease or condition selected from the group consisting of acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema, lung transplantation-induced acute graft dysfunction and bronchiolitis obliterans after lung transplantation. In various embodiments of the kit or package the instructions or package insert indicates that the therapeutic agents or dosage units are suitable for use in treating a patient suffering from or at risk of suffering from inflammation and/or graft rejection associated with organ transplantation, in particular lung transplantation, including, without being limited to, primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD) after organ transplantation, in particular in lung transplantation.

In various embodiments the composition comprises one or more double-stranded nucleic acid (dsNA) agents which down-regulate or inhibit the expression/activity/function of a TLR2 gene and/or TLR2 gene product including DNA and mRNA.

In various embodiments the combination comprises one or more double-stranded nucleic acid (dsNA) agents which down-regulate or inhibit the expression/activity/function of at least two genes and/or gene products including DNA and mRNA selected from: (i) TLR2 and (ii) TLR4.

The mRNA coding sequence for human TLR2 is exemplified by SEQ ID NO:1 and the mRNA coding sequence for human TLR4 is exemplified by SEQ ID NO:2, SEQ ID NO:3 and SEQ ID NO:4.

In one embodiment the composition comprises at least one dsNA molecule which down-regulates TLR2.

In another embodiment the combination comprises one or more dsNA agents which down-regulate TLR2 and TLR4. In one embodiment the combination comprises at least one dsNA molecule which down-regulates TLR2 and at least one dsNA molecule which down-regulates TLR4.

In some embodiments provided is a tandem dsRNA comprising dsRNA targeting at least both TLR2 and TLR4.

In some embodiments provided is a triple armed structure, also known as RNAistar. Said triple-stranded oligonucleotide comprises an oligoribonucleotide having the general structure:

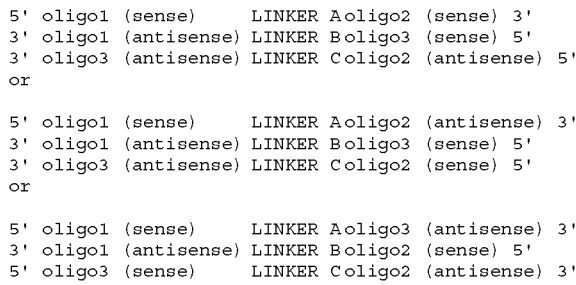

```
5' oligo1 (sense)      LINKER A oligo2 (sense)     3'
3' oligo1 (antisense)  LINKER B oligo3 (sense)     5'
3' oligo3 (antisense)  LINKER C oligo2 (antisense) 5'
or
5' oligo1 (sense)      LINKER A oligo2 (antisense) 3'
3' oligo1 (antisense)  LINKER B oligo3 (sense)     5'
3' oligo3 (antisense)  LINKER C oligo2 (sense)     5'
or
5' oligo1 (sense)      LINKER A oligo3 (antisense) 3'
3' oligo1 (antisense)  LINKER B oligo3 (sense)     5'
5' oligo3 (sense)      LINKER C oligo2 (antisense) 3'
```

Wherein one or more of linker A, linker B or linker C is present; any combination of two or more oligonucleotides and one or more of linkers A-C is possible, so long as the polarity of the strands and the general structure of the molecule remains. Further, if two or more of linkers A-C are present, they may be identical or different. In some embodiments a "gapped" RNAistar compound is preferred wherein the compound comprises three RNA duplexes.

Figure 7:
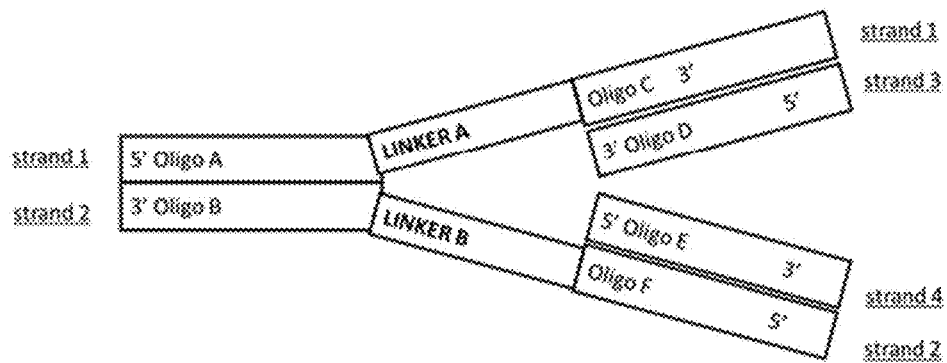
FIG. 7 shows a compound consisting of four ribonucleotide strands forming three RNA duplexes having the general structure as shown.

A compound consisting of four ribonucleotide strands forming three RNA duplexes having the general structure as shown in FIG. 7.

As shown in FIG. 7, each of oligo A, oligo B, oligo C, oligo D, oligo E and oligo F represents at least 19 consecutive ribonucleotides, wherein from 18 to 40 of such consecutive ribonucleotides, in each of oligo A, B, C, D, E and F comprise a strand of a RNA duplex, wherein each ribonucleotide may be modified or unmodified;

wherein strand 1 comprises oligo A which is either a sense portion or an antisense portion of a first RNA duplex of the compound, strand 2 comprises oligo B which is complementary to at least 19 nucleotides in oligo A, and oligo A and oligo B together form a first RNA duplex that targets a first target mRNA;

wherein strand 1 further comprises oligo C which is either a sense portion or an antisense strand portion of a second RNA duplex of the compound, strand 3 comprises oligo D which is complementary to at least 19 nucleotides in oligo C and oligo C and oligo D together form a second RNA duplex that targets a second target mRNA;

wherein strand 4 comprises oligo E which is either a sense portion or an antisense strand portion of a third RNA duplex of the compound, strand 2 further comprises oligo F which is complementary to at least 19 nucleotides in oligo E and oligo E and oligo F together form a third RNA duplex that targets a third target mRNA; and wherein linker A is a moiety that covalently links oligo A and oligo C; linker B is a moiety that covalently links oligo B and oligo F, and linker A and linker B can be the same or different.

In some embodiments the first, second and third RNA duplex target the same gene, i.e. TLR2. In other embodiments two of the first, second or third siRNA duplexes target the same mRNA, e.g. TLR2 and the third RNA duplex targets a different mRNA, for example TLR4. In other embodiments two of the first, second or third siRNA duplexes target the same mRNA, e.g. TLR4 and the third RNA duplex targets a different mRNA, for example TLR2.

"Toll-like receptor 2" or "fir-2" or "TLR-2" or "tlr2" or "TLR2" are used interchangeably and refer to any Toll-like receptor 2 peptide or polypeptide having any TLR2 protein activity. TLR2 has also been designated as CD282 (cluster of differentiation 282). Toll-like receptor 2 (or more particularly human TLR2) may have an amino acid sequence that is the same, or substantially the same, as SEQ ID NO. 1.

"Toll-like receptor 4" or "fir-4" or "TLR-4" or "tlr4" or "TLR4" are used interchangeably and refer to any Toll-like receptor 4 peptide or polypeptide having any TLR4 protein activity. TLR4 has also been designated as CD284 (cluster of differentiation 284). Toll-like receptor 4 (or more particularly human TLR4) may have an amino acid sequence that is the same, or substantially the same, as SEQ ID NO. 2-4.

As used herein the term "nucleotide sequence encoding TLR2 and TLR4" means a nucleotide sequence that codes for a TLR2 and TLR4 protein, respectively, or portion thereof. The term "nucleotide sequence encoding TLR2 and TLR4" is also meant to include TLR2 and TLR4 coding sequences such as TLR2 and TLR4 isoforms, mutant TLR2 and TLR4 genes, splice variants of TLR2 and TLR4 genes, and TLR2 and TLR4 gene polymorphisms. A nucleic acid sequence encoding TLR2 and TLR4 includes mRNA sequences encoding TLR2 and TLR4, which can also be referred to as TLR2 mRNA and TLR4 mRNA. Exemplary sequence of human TLR2 is SEQ ID NO:1. Exemplary sequences of human TLR4 mRNA are SEQ ID NO:2, SEQ ID NO:3 and SEQ ID NO:4.

In some embodiments the inhibitors or therapeutic agents disclosed herein comprise a molecule, a compound which can down-regulate or inhibit expression and/or function of a gene and/or gene product selected from TLR2 and TLR4. Preferably the therapeutic agent is independently selected from the group consisting of a small organic molecule; a protein; an antibody or fragment thereof a peptide, a peptidomimetic and a nucleic acid molecule.

Examples of an antibody includes polyclonal, monoclonal, chimeric, humanized or human antibodies and antigen-binding fragments thereof. Examples of TLR2 binding antibodies are anti-human TLR2 antibody, mouse monoclonal anti-human TLR2, rabbit anti-human TLR2, goat anti-human TLR2 and the like which are raised against TLR2.

Examples of an antibody includes polyclonal, monoclonal, chimeric, humanized or human antibodies and antigen-binding fragments thereof. Examples of TLR4 binding antibodies are anti-human TLR4 antibody, mouse monoclonal anti-human TLR4, rabbit anti-human TLR4, goat anti-human TLR4 and the like which are raised against TLR4.

In some embodiments the inhibitor or therapeutic agent of the present disclosure comprise a peptide. The term "peptide", as used herein, refers to a compound consisting of from about two to about ninety amino acid residues wherein the amino group of one amino acid is linked to the carboxyl group of another amino acid by a peptide bond. Preferred peptide sequences are short (e.g. 3 to 20 amino acids in length) and lipophilic, such that they can cross cell membranes to a sufficient extent. A peptide can be, for example, derived or removed from a native protein by enzymatic or chemical cleavage, or can be prepared using conventional peptide synthesis techniques (e.g., solid phase synthesis) or molecular biology techniques (see Sambrook, J. et al., Molecular Cloning: A Laboratory Manual, Cold Spring Harbor Press, Cold Spring Harbor, N.Y. (1989)). A "peptide" can comprise any suitable L- and/or D-amino acid, for example, common o-amino acids (e.g., alanine, glycine, valine), non-α-amino acids (e.g., β-alanine, 4-aminobutyric acid, 6-aminocaproic acid, sarcosine, statine), and unusual amino acids (e.g., citrulline, homocitrulline, homoserine, norleucine, norvaline, ornithine). The amino, carboxyl and/or other functional groups on a peptide can be free (e.g., unmodified) or protected with a suitable protecting group. Suitable protecting groups for amino and carboxyl groups, and means for adding or removing protecting groups are known in the art and are disclosed in, for example, Green and Wuts, "Protecting Groups in Organic Synthesis", John Wiley and Sons, 1991. The functional groups of a peptide can also be derivatized (e.g., alkylated) using art-known methods.

In some embodiments the inhibitors or therapeutic agents provided herein include a peptidomimetic. The term "peptidomimetic", as used herein, refers to molecules which are not polypeptides, but which mimic aspects of their structures and have the same functional groups as peptides, which can inhibit TLR2 or TLR4. Peptidomimetics are designed, for example, by identifying a peptide inhibitor of TLR2 or TLR4 and modifying it using amino acid substitutes that advantageously modify the properties of the peptide, for example by increasing stability and or activity.

In some embodiments the inhibitors or therapeutic agents disclosed herein include nucleic acid molecules. As used herein, the term "nucleic acid molecule" or "nucleic acid" are used interchangeably and refer to an oligonucleotide, nucleotide or polynucleotide. Variations of "nucleic acid molecule" are described in more detail herein. A nucleic acid molecule encompasses both modified nucleic acid molecules and unmodified nucleic acid molecules as described herein. A nucleic acid molecule may include deoxyribonucleotides, ribonucleotides, modified nucleotides or nucleotide analogs in any combination.

As used herein, the term "nucleotide" refers to a chemical moiety having a sugar (or an analog thereof, or a modified sugar), a nucleotide base (or an analog thereof, or a modified base), and a phosphate group (or analog thereof, or a modified phosphate group). A nucleotide encompasses both modified nucleotides or unmodified nucleotides as described herein. As used herein, nucleotides may include deoxyribonucleotides (e.g., unmodified deoxyribonucleotides), ribonucleotides (e.g., unmodified ribonucleotides), and modified nucleotide analogs including, inter alia, locked nucleic acids and unlocked nucleic acids, peptide nucleic acids, L-nucleotides (also referred to as mirror nucleotides), ethylene-bridged nucleic acid (ENA), arabinoside, PACE, nucleotides with a 6 carbon sugar, as well as nucleotide analogs (including abasic nucleotides) often considered to be non-nucleotides. In some embodiments, nucleotides may be modified in the sugar, nucleotide base and/or in the phosphate group with any modification known in the art and/or any modification such as modifications described herein. A "polynucleotide" or "oligonucleotide" as used herein refer to a chain of linked nucleotides; polynucleotides and oligonucleotides may likewise have modifications in the nucleotide sugar, nucleotide bases and phosphate backbones as are well known in the art and/or are disclosed herein.

As used herein, the term "short interfering nucleic acid", "siNA", or "short interfering nucleic acid molecule" refers to any nucleic acid molecule capable of modulating gene expression or viral replication. Preferably siNA inhibits or down regulates gene expression or viral replication. siNA includes without limitation nucleic acid molecules that are capable of mediating sequence specific RNA interference (RNAi), for example short interfering RNA (siRNA), double-stranded NA (dsNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others. As used herein, "short interfering nucleic acid", "siNA", or "short interfering nucleic acid molecule" has the meaning described in more detail elsewhere herein.

As used herein, the term "complementary" means that a nucleic acid can form hydrogen bond(s) with another nucleic acid sequence by either traditional Watson-Crick or other non-traditional types. In reference to the nucleic molecules disclosed herein, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Fully complementary" means that all the contiguous residues of a nucleic acid sequence will form hydrogen bond with the same number of contiguous residues in a second nucleic acid sequence. In one embodiment, a nucleic acid molecule disclosed herein includes about 15 to about 35 or more (e.g., about 15, 16, 17, 18, 19, 20, 21, 22, 23, 24, 25, 26, 27, 28, 29, 30, 31, 32, 33, 34 or 35 or more) nucleotides that are complementary to one or more target nucleic acid molecules or a portion thereof.

As used herein, the term "sense region" refers to a nucleotide sequence of a dsNA molecule complementary (partially or fully) to an antisense region of the dsNA molecule. The sense strand of a dsNA molecule can include a nucleic acid sequence having homology with a target nucleic acid sequence. As used herein, "sense strand" refers to nucleic acid molecule that includes a sense region and may also include additional nucleotides. The sense strand may be between 17 and 40 nucleotides in length, for instance, 17, 18, 19, 20, 21, 22, 23, 24, 25, 26, 27, 28, 29, 30, 31, 32, 33, 34, 35, 36, 37, 38, 39 or 40 nucleotides.

As used herein, the term "antisense region" refers to a nucleotide sequence of a dsNA molecule complementary (partially or fully) to a target nucleic acid sequence, preferably a target mRNA. The antisense strand of a dsNA molecule can optionally include a nucleic acid sequence complementary to a sense region of the dsNA molecule. As used herein, "antisense strand" refers to nucleic acid molecule that includes an antisense region and may also include additional nucleotides. The antisense strand may be between 17 and 40 nucleotides in length, for instance, 17, 18, 19, 20, 21, 22, 23, 24, 25, 26, 27, 28, 29, 30, 31, 32, 33, 34, 35, 36, 37, 38, 39 or 40 nucleotides.

As used herein, the term "substantially complementary" means the antisense strand includes 1, 2, 3, 4, 5, 6, 7, 8, 9 or 10 nucleotides that are not complementary to a nucleotide sequence of an oligonucleotide, such as a sense strand or a target mRNA. In some embodiments, an antisense strand may include 1, 2, or 3 nucleotides that are unpaired, i.e., do not have a corresponding complementary nucleotide in the sense strand or in a target mRNA.

As used herein, the term "RNA" refers to a molecule that includes at least one ribonucleotide residue.

As used herein, the term "duplex region" refers to the region in two complementary or substantially complementary oligonucleotides that form base pairs with one another, either by Watson-Crick base pairing or any other manner that allows for a duplex between oligonucleotide strands that are complementary or substantially complementary. For example, an oligonucleotide strand having 21 nucleotide units can base pair with another oligonucleotide of 21 nucleotide units, yet only 19 bases on each strand are complementary or substantially complementary, such that the "duplex region" consists of 19 base pairs. The remaining base pairs may, for example, exist as 5' and 3' overhangs. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well know in the art. Alternatively, two strands can be synthesized and added together under biological conditions to determine if they anneal to one another.

As used herein, the terms "non-pairing nucleotide analog" means a nucleotide analog which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analog is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

An "abasic nucleotide" or "abasic nucleotide analog" as used herein may also be often referred to herein and in the art as a pseudo-nucleotide or an unconventional moiety. While a nucleotide is a monomeric unit of nucleic acid, generally consisting of a ribose or deoxyribose sugar, a phosphate, and a base (adenine, guanine, thymine, or cytosine in DNA; adenine, guanine, uracil, or cytosine in RNA). an abasic or pseudo-nucleotide lacks a base, and thus is not strictly a nucleotide as the term is generally used in the art. Abasic deoxyribose moieties include for example, abasic deoxyribose-3'-phosphate; 1,2-dideoxy-D-ribofuranose-3-phosphate; 1,4-anhydro-2-deoxy-D-ribitol-3-phosphate.

Inverted abasic deoxyribose moieties include inverted deoxyriboabasic; 3',5' inverted deoxyabasic 5'-phosphate.

The term "capping moiety" (or "z" ") as used herein includes a moiety which can be covalently linked to the 5' terminus of the sense strand ((N')y) and includes abasic ribose moiety, abasic deoxyribose moiety, modifications to abasic ribose and abasic deoxyribose moieties including 2' O alkyl modifications; inverted abasic ribose and abasic deoxyribose moieties and modifications thereof; C6-imino-Pi; a mirror nucleotide including L-DNA and L-RNA; 5'OMe nucleotide; and nucleotide analogs including 4',5'-methylene nucleotide; 1-(β-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non bridging methylphosphonate and 5'-mercapto moieties.

Certain capping moieties may be abasic ribose or abasic deoxyribose moieties; inverted abasic ribose or inverted abasic deoxyribose moieties; C6-amino-Pi; a mirror nucleotide including L-DNA and L-RNA. The nucleic acid molecules as disclosed herein may be synthesized using one or more inverted nucleotides, for example inverted thymidine or inverted adenine (for example see Takei, et al., 2002. JBC 277(26):23800-06).

In some embodiments of Structure (A1) and Structure (A2) at least one of Z or Z' is present and comprises at least two non-nucleotide moieties covalently attached to the strand in which it is present. In some embodiments each of Z and Z' independently includes a C3 alkyl, C3 alcohol or C3 ester moiety. In some embodiments Z' is absent and Z is present and includes a non-nucleotide C3 moiety. In some embodiments Z is absent and Z' is present and includes a non-nucleotide C3 moiety. Exemplary non-nucleotide moieties include the alkyl and modified alkyl moieties shown below:

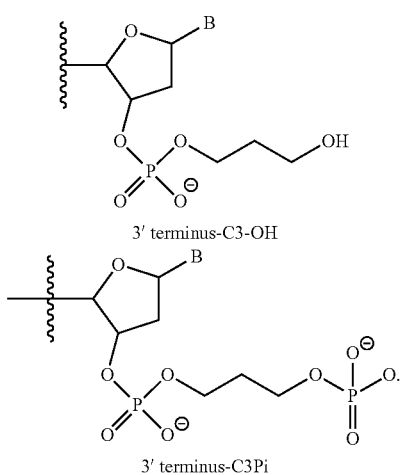

3' terminus-C3-OH

3' terminus-C3Pi

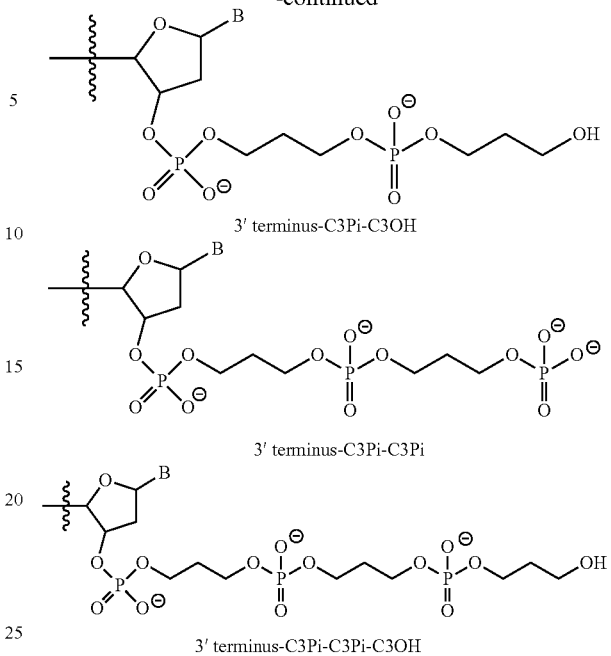

3' terminus-C3Pi-C3OH

3' terminus-C3Pi-C3Pi

3' terminus-C3Pi-C3Pi-C3OH

In some embodiments of Structures (A1) and (A2), each of N and N' is an unmodified nucleotide. In some embodiments at least one of N or N' includes a chemically modified nucleotide or an unconventional moiety. In some embodiments the unconventional moiety is selected from a mirror nucleotide, an abasic ribose moiety and an abasic deoxyribose moiety. In some embodiments the unconventional moiety is a mirror nucleotide, preferably an L-deoxyribonucleotide (L-DNA) moiety. In some embodiments at least one of N or N' includes a 2'-OMe sugar-modified ribonucleotide.

The term "unconventional moiety" as used herein refers to non-nucleotide moieties including an abasic moiety, an inverted abasic moiety, a hydrocarbon (alkyl) moiety and derivatives thereof, and further includes a deoxyribonucleotide, a modified deoxyribonucleotide, a mirror nucleotide (L-DNA or L-RNA), a non-base pairing nucleotide analog and a nucleotide joined to an adjacent nucleotide by a 2'-5' internucleotide phosphate bond; bridged nucleic acids including LNA and ethylene bridged nucleic acids, linkage modified (e.g. PACE) and base modified nucleotides, as well as additional moieties explicitly disclosed herein as unconventional moieties.

As used herein, the term "inhibit", "down-regulate", or "reduce" with respect to gene expression means that the expression of a target gene, or level of RNA molecules or equivalent RNA molecules encoding one or more proteins or protein subunits (e.g., mRNA), or activity of one or more proteins or protein subunits, is reduced below that observed in the absence of an inhibitory factor (such as a nucleic acid molecule, e.g., an dsNA, for example having structural features as described herein); for example the expression may be reduced to 90%, 80%, 70%, 60%, 50%, 40%, 30%, 20%, 10%, 5% or less than that observed in the absence of an inhibitor.

RNA Interference and dsNA Nucleic Acid Molecules

RNA interference refers to the process of sequence-specific post-transcriptional gene silencing in animals mediated by short interfering RNAs (siRNAs) (Zamore et al., 2000, Cell, 101, 25-33; Fire et al., 1998, Nature, 391, 806; Hamilton et al., 1999, Science, 286, 950-951; Lin et al., 1999, Nature, 402, 128-129; Sharp, 1999, Genes & Dev., 13:139-141; and Strauss, 1999, Science, 286, 886). The corresponding process in plants (Heifetz et al., International PCT Publication No. WO 99/61631) is often referred to as post-transcriptional gene silencing (PTGS) or RNA silencing. The process of post-transcriptional gene silencing is thought to be an evolutionarily-conserved cellular defense mechanism used to prevent the expression of foreign genes (Fire et al., 1999, Trends Genet., 15, 358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA or viral genomic RNA. The presence of dsRNA in cells triggers the RNAi response through a mechanism that has yet to be fully characterized. This mechanism appears to be different from other known mechanisms involving double-stranded RNA-specific ribonucleases, such as the interferon response that results from dsRNA-mediated activation of protein kinase PKR and 2',5'-oligoadenylate synthetase resulting in non-specific cleavage of mRNA by ribonuclease L (see for example U.S. Pat. Nos. 6,107,094; 5,898,031; Clemens et al., 1997, J. Interferon & Cytokine Res., 17, 503-524; Adah et al., 2001, Curr. Med. Chem., 8, 1189).

The presence of long dsRNAs in cells stimulates the activity of a ribonuclease III enzyme referred to as dicer (Bass, 2000, Cell, 101, 235; Zamore et al., 2000, Cell, 101, 25-33; Hammond et al., 2000, Nature, 404, 293). Dicer is involved in the processing of the dsRNA into short pieces of dsRNA known as short interfering RNAs (siRNAs) (Zamore et al., 2000, Cell, 101, 25-33; Bass, 2000, Cell, 101, 235; Berstein et al., 2001, Nature, 409, 363). Short interfering RNAs derived from dicer activity are typically about 21 to about 23 nucleotides in length and include about 19 base pair duplexes (Zamore et al., 2000, Cell, 101, 25-33; Elbashir et al., 2001, Genes Dev., 15, 188). Dicer has also been implicated in the excision of 21- and 22-nucleotide small temporal RNAs (stRNAs) from precursor RNA of conserved structure that are implicated in translational control (Hutvagner et al., 2001, Science, 293, 834). The RNAi response also features an endonuclease complex, commonly referred to as an RNA-induced silencing complex (RISC), which mediates cleavage of single-stranded RNA having sequence complementary to the antisense strand of the siRNA duplex. Cleavage of the target RNA takes place in the middle of the region complementary to the antisense strand of the siRNA duplex (Elbashir et al., 2001, Genes Dev., 15, 188).

RNAi has been studied in a variety of systems. Fire et al., 1998, Nature, 391, 806, were the first to observe RNAi in *C. elegans*. Bahramian and Zarbl, 1999, Molecular and Cellular Biology, 19, 274-283 and Wianny and Goetz, 1999, Nature Cell Biol., 2, 70, describe RNAi mediated by dsRNA in mammalian systems. Hammond et al., 2000, Nature, 404, 293, describe RNAi in *Drosophila* cells transfected with dsRNA. Elbashir et al., 2001, Nature, 411, 494 and Tuschl et al., International PCT Publication No. WO 01/75164, describe RNAi induced by introduction of duplexes of synthetic 21-nucleotide RNAs in cultured mammalian cells including human embryonic kidney and HeLa cells. Recent work in *Drosophila* embryonic lysates (Elbashir et al., 2001, EMBO J., 20, 6877 and Tuschl et al., International PCT Publication No. WO 01/75164) has revealed certain requirements for siRNA length, structure, chemical composition, and sequence that are essential to mediate efficient RNAi activity.

Nucleic acid molecules (for example having structural features as disclosed herein) may inhibit or down regulate gene expression or viral replication by mediating RNA interference "RNAi" or gene silencing in a sequence-specific manner; see e.g., Zamore et al., 2000, Cell, 101, 25-33; Bass, 2001, Nature, 411, 428-429; Elbashir et al., 2001, Nature, 411, 494-498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914; Allshire, 2002, Science, 297, 1818-1819; Volpe et al., 2002, Science, 297, 1833-1837; Jenuwein, 2002, Science, 297, 2215-2218; and Hall et al., 2002, Science, 297, 2232-2237; Hutvagner and Zamore, 2002, Science, 297, 2056-60; McManus et al., 2002, RNA, 8, 842-850; Reinhart et al., 2002, Gene & Dev., 16, 1616-1626; and Reinhart & Bartel, 2002, Science, 297, 1831).

A double-stranded nucleic acid molecule can be assembled from two separate polynucleotide strands, where one strand is the sense strand and the other is the antisense strand in which the antisense and sense strands are self-complementary (i.e. each strand includes nucleotide sequence that is complementary to nucleotide sequence in the other strand); such as where the antisense strand and sense strand form a duplex or double-stranded structure having any length and structure as described herein for nucleic acid molecules as provided, for example wherein the double-stranded region (duplex region) is about 15 to about 40 (e.g., about 17, 18, 19, 20, 21, 22, 23, 24, 25, 26, 27, 28, 29, 30, 31, 32, 33, 34, 35, 36, 37, 38, 39, or 40 base pairs); the antisense strand includes nucleotide sequence that is complementary to nucleotide sequence in a target nucleic acid molecule (i.e., TLR2 and TLR4 mRNA) or a portion thereof and the sense strand includes nucleotide sequence corresponding to the target nucleic acid sequence or a portion thereof (e.g., about 17 to about 40 nucleotides of the nucleic acid molecules herein are complementary to the target nucleic acid or a portion thereof).

In certain aspects and embodiments a nucleic acid molecule (e.g., a dsNA molecule) provided herein may be a "RISC length" molecule or may be a Dicer substrate as described in more detail below.

A dsNA nucleic acid molecule may include separate sense and antisense sequences or regions, where the sense and antisense regions are covalently linked by nucleotide or non-nucleotide linkers molecules as is known in the art, or are alternately non-covalently linked by ionic interactions, hydrogen bonding, van der Waals interactions, hydrophobic interactions, and/or stacking interactions. Nucleic acid molecules may include a nucleotide sequence that is complementary to nucleotide sequence of a target gene or of a target mRNA. Nucleic acid molecules may interact with nucleotide sequence of a target gene in a manner that causes inhibition of expression of the target gene.

Alternatively, a dsNA nucleic acid molecule is assembled from a single polynucleotide, where the self-complementary sense and antisense regions of the nucleic acid molecules are linked by means of a nucleic acid based or non-nucleic acid-based linker(s), i.e., the antisense strand and the sense strand are part of one single polynucleotide that having an antisense region and sense region that fold to form a duplex region (for example to form a "hairpin" structure as is well known in the art). Such dsNA nucleic acid molecules can be a polynucleotide with a duplex, asymmetric duplex, hairpin or asymmetric hairpin secondary structure, having self-complementary sense and antisense regions, wherein the antisense region includes nucleotide sequence that is complementary to nucleotide sequence in a separate target nucleic acid molecule (e.g. TLR2 mRNA or TLR4 mRNA) or a portion thereof and the sense region having nucleotide sequence corresponding to the target nucleic acid sequence (i.e., a sequence of TLR2 mRNA or a sequence of TLR4 mRNA). Such dsNA nucleic acid molecules can be a circular single-stranded polynucleotide having two or more loop structures and a stem comprising self-complementary sense and antisense regions, wherein the antisense region includes nucleotide sequence that is complementary to nucleotide sequence in a target nucleic acid molecule (e.g. TLR2 mRNA or TLR4 mRNA) or a portion thereof and the sense region having nucleotide sequence corresponding to the target nucleic acid sequence (e.g. TLR2 mRNA or TLR4 mRNA) or a portion thereof, and wherein the circular polynucleotide can be processed either in vivo or in vitro to generate an active nucleic acid molecule capable of mediating RNAi.

Chemical Modifications of Nucleic Acid Molecules

In certain aspects and embodiments, the methods provided herein utilizes nucleic acid therapeutic agents. The nucleic acid molecules (e.g., dsNA molecules) as provided herein include one or more modifications (or chemical modifications). Without being bound to theory, the chemical modifications confer upon the nucleic acid molecules beneficial properties including nuclease stability, reduced off-target activity and or reduced immune stimulation. In certain embodiments, such modifications include any changes to a nucleic acid molecule or polynucleotide that would make the molecule different than a standard ribonucleotide or RNA molecule (i.e., that includes standard adenine, cytosine, uracil, or guanine moieties); which may be referred to as an "unmodified" ribonucleotide or unmodified ribonucleic acid. Traditional DNA bases and polynucleotides having a 2'-deoxy sugar represented by adenine, cytosine, thymine, or guanine moieties may be referred to as an "unmodified deoxyribonucleotide" or "unmodified deoxyribonucleic acid"; accordingly, the term "unmodified nucleotide" or "unmodified nucleic acid" as used herein refers to an "unmodified ribonucleotide" or "unmodified ribonucleic acid" unless there is a clear indication to the contrary. Such modifications can be in the nucleotide sugar, nucleotide base, nucleotide phosphate group and/or the phosphate backbone of a polynucleotide.

In certain embodiments, modifications as disclosed herein, may be used to increase RNAi activity of a dsNA molecule and/or to increase the in vivo stability of the dsNA molecules, particularly the stability in serum, and/or to increase bioavailability of the dsNA molecules. Non-limiting examples of modifications include without limitation internucleotide or internucleoside linkages; deoxyribonucleotides or dideoxyribonucleotides at any position and strand of the double-stranded nucleic acid molecule; nucleic acid (e.g., ribonucleic acid) with a modification at the 2'-position preferably selected from an amino, fluoro, methoxy, alkoxy and alkyl; 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, biotin group, and terminal glyceryl and/or inverted deoxy abasic residue incorporation, sterically hindered molecules, such as fluorescent molecules and the like. Other nucleotides modifiers could include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). Further details on various modifications are described in more detail below.

Non-limiting examples of chemically modified nucleotides having a northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides, 2'-deoxy-2'-chloro nucleotides, 2'-azido nucleotides, and 2'-O-methyl nucleotides. Locked nucleic acids, or LNA's are described, for example, in Elman et al., 2005; Kurreck et al., 2002; Crinelli et al., 2002; Braasch and Corey, 2001; Bondensgaard et al., 2000; Wahlestedt et al., 2000; and International Patent Publication Nos. WO 00/47599, WO 99/14226, and WO 98/39352 and WO 2004/083430. In one embodiment of the therapeutic agent provided herein, an LNA is incorporated at the 5' terminus of the sense strand of the nucleic acid molecule.

Chemical modifications also include unlocked nucleic acids, or UNAs, which are non-nucleotide, acyclic analogues, in which the C2'-C3' bond is not present (although UNAs are not truly nucleotides, they are expressly included in the scope of "modified" nucleotides or modified nucleic acids as contemplated herein). Exemplary UNAs are disclosed in Nucleic Acids Symposium Series No. 52 p. 133-134 (2008). In certain embodiments a nucleic acid molecule (e.g., a siNA molecule) as described herein include one or more UNAs; or one UNA. In some embodiments, a nucleic acid molecule (e.g., a siNA molecule) as described herein has a 3'-overhang that includes one or two UNAs in the 3' overhang. In some embodiments a nucleic acid molecule (e.g., a siNA molecule) as described herein includes a UNA (for example one UNA) in the antisense strand; for example in position 6 or position 7 of the antisense strand.

Chemical modifications also include non-pairing nucleotide analogs, for example as disclosed herein. Chemical modifications further include unconventional moieties as disclosed herein.

Chemical modifications also include terminal modifications on the 5' and/or 3' part of the oligonucleotides and are also known as capping moieties. Such terminal modifications are selected from a nucleotide, a modified nucleotide, a lipid, a peptide, and a sugar, an abasic ribose moiety and an abasic deoxyribose moiety.

Chemical modifications also include six membered "six membered ring nucleotide analogs." Examples of six-membered ring nucleotide analogs are disclosed in Allart, et al (Nucleosides & Nucleotides, 1998, 17:1523-1526; and Perez-Perez, et al., 1996, Bioorg. and Medicinal Chem Letters 6:1457-1460) Oligonucleotides including 6-membered ring nucleotide analogs including hexitol and altritol nucleotide monomers are disclosed in International patent application publication No. WO 2006/047842.

Chemical modifications also include "mirror" nucleotides which have a reversed chirality as compared to normal naturally occurring nucleotide; that is a mirror nucleotide may be an "L-nucleotide" analogue of naturally occurring D-nucleotide (see U.S. Pat. No. 6,602,858). Mirror nucleotides may further include at least one sugar or base modification and/or a backbone modification, for example, as described herein, such as a phosphorothioate or phosphonate moiety. U.S. Pat. No. 6,602,858 discloses nucleic acid catalysts including at least one L-nucleotide substitution. Mirror nucleotides include for example L-DNA (L-deoxyriboadenosine-3'-phosphate (mirror dA); L-deoxyribocytidine-3'-phosphate (mirror dC); L-deoxyriboguanosine-3'-phosphate (mirror dG); L-deoxyribothymidine-3'-phosphate (mirror image dT)) and L-RNA (L-riboadenosine-3'-phosphate (mirror rA); L-ribocytidine-3'-phosphate (mirror rC); L-riboguanosine-3'-phosphate (mirror rG); L-ribouracil-3'-phosphate (mirror dU).

In some embodiments, modified ribonucleotides include modified deoxyribonucleotides, for example 5'OMe DNA (5-methyl-deoxyriboguanosine-3'-phosphate) which may be useful as a nucleotide in the 5' terminal position (position number 1); PACE (deoxyriboadenine 3' phosphonoacetate, deoxyribocytidine 3' phosphonoacetate, deoxyriboguanosine 3' phosphonoacetate, deoxyribothymidine 3' phosphonoacetate.

Modifications may be present in one or more strands of a nucleic acid molecule disclosed herein, e.g., in the sense strand, the antisense strand, or both strands. In certain embodiments, the antisense strand may include modifications and the sense strand my only include unmodified ribonucleotides.

Nucleobases

Nucleobases of the nucleic acid disclosed herein may include unmodified ribonucleotides (purines and pyrimidines) such as adenine, guanine, cytosine, uridine. The nucleobases in one or both strands can be modified with natural and synthetic nucleobases such as, thymine, xanthine, hypoxanthine, ionosine, 2-aminoadenine, 6-methyl and other alkyl derivatives of adenine and guanine, any "universal base" nucleotides; 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 8-halo, amino, thiol, thioalkyl, hydroxyl and other 8-substituted adenines and guanines, 5-trifluoromethyl and other 5-substituted uracils and cytosines, 7-methylguanine, deazapurines, heterocyclic substituted analogs of purines and pyrimidines, e.g., aminoethyoxy phenoxazine, derivatives of purines and pyrimidines (e.g., 1-alkyl-, 1-alkenyl-, heteroaromatic- and 1-alkynyl derivatives) and tautomers thereof, 8-oxo-$N^6$-methyladenine, 7-diazaxanthine, 5-methylcytosine, 5-methyluracil, 5-(1-propynyl)uracil, 5-(1-propynyl) cytosine and 4,4-ethanocytosine). Other examples of suitable bases include non-purinyl and non-pyrimidinyl bases such as 2-aminopyridine and triazines.

Sugar Moieties

Sugar moieties in nucleic acid disclosed herein may include 2'-hydroxyl-pentofuranosyl sugar moiety without any modification. Alternatively, sugar moieties can be modified such as, 2'-deoxy-pentofuranosyl sugar moiety, D-ribose, hexose, modification at the 2' position of the pentofuranosyl sugar moiety such as 2'-O-alkyl (including 2'-O-methyl and 2'-O-ethyl), i.e., 2'-alkoxy, 2'-amino, 2'-O-allyl, 2'-S-alkyl, 2'-halogen (including 2'-fluoro, chloro, and bromo), 2'-methoxyethoxy, 2'-O-methoxyethyl, 2'-O-2-methoxyethyl, 2'-allyloxy (—OCH$_2$CH=CH$_2$), 2'-propargyl, 2'-propyl, ethynyl, ethenyl, propenyl, CF, cyano, imidazole, carboxylate, thioate, $C_1$ to $C_{10}$ lower alkyl, substituted lower alkyl, alkaryl or aralkyl, OCF$_3$, OCN, O—, S—, or N-alkyl; O—, S, or N-alkenyl; SOCH$_3$; SO$_2$CH$_3$; ONO$_2$; NO$_2$, N$_3$; heterozycloalkyl; heterozycloalkaryl; aminoalkylamino; polyalkylamino or substituted silyl, as, among others, for example as described in European patents EP 0 586 520 B1 or EP 0 618 925 B1.

Alkyl group includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls may have from 3-8 carbon atoms in their ring structure, and more preferably have 5 or 6 carbons in the ring structure. The term $C_1$-$C_6$ includes alkyl groups containing 1 to 6 carbon atoms. The alkyl group can be substituted alkyl group such as alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Alkoxy group includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

In some embodiments, the pentafuronosyl ring may be replaced with acyclic derivatives lacking the C2'-C3'-bond of the pentafuronosyl ring. For example, acyclonucleotides may substitute a 2-hydroxyethoxymethyl group for-the 2'-deoxyribofuranosyl sugar normally present in dNMPs.

Halogens include fluorine, bromine, chlorine, iodine.

Backbone

The nucleoside subunits of the nucleic acid disclosed herein may be linked to each other by phosphodiester bond. The phosphodiester bond may be optionally substituted with other linkages. For example, phosphorothioate, thiophosphate-D-ribose entities, triester, thioate, 2'-5' bridged backbone (may also be referred to as 5'-2'), PACE, 3'-(or -5') deoxy-3'-(or -5')thio-phosphorothioate, phosphorodithioate, phosphoroselenates, 3'-(or -5')deoxy phosphinates, borano phosphates, 3'-(or -5')deoxy-3'-(or -5')amino phosphoramidates, hydrogen phosphonates, phosphonates, borano phosphate esters, phosphoramidates, alkyl or aryl phosphonates and phosphotriester modifications such as alkylphosphotriesters, phosphotriester phosphorus linkages, 5'-ethoxyphosphodiester, P-alkyloxyphosphotriester, methylphosphonate, and nonphosphorus containing linkages for example, carbonate, carbamate, silyl, sulfur, sulfonate, sulfonamide, formacetal, thioformacetyl, oxime, methyleneimino, methylenemethylimino, methylenehydrazo, methylenedimethylhydrazo and methyleneoxymethylimino linkages.

Nucleic acid molecules disclosed herein may include a peptide nucleic acid (PNA) backbone. The PNA backbone includes repeating N-(2-aminoethyl)-glycine units linked by peptide bonds. The various bases such as purine, pyrimidine, natural and synthetic bases are linked to the backbone by methylene carbonyl bonds.

Terminal Phosphates

Figure 8:
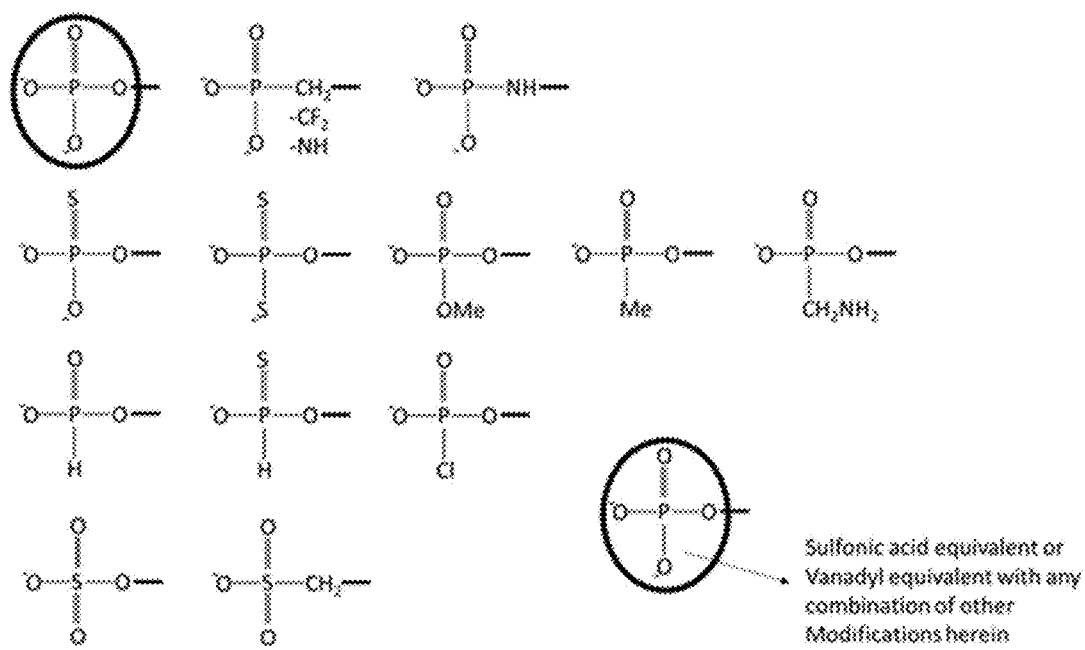
FIG. 8 shows exemplary chemically modified terminal phosphate groups.

Modifications can be made at terminal phosphate groups. Non-limiting examples of different stabilization chemistries can be used, e.g., to stabilize the 3'-end of nucleic acid sequences, including (1) [3-3']-inverted deoxyribose; (2) deoxyribonucleotide; (3) [5'-3']-3'-deoxyribonucleotide; (4) [5'-3']-ribonucleotide; (5) [5'-3']-3'-O-methyl ribonucleotide; (6) 3'-glyceryl; (7) [3'-5']-3'-deoxyribonucleotide; (8) [3'-3']-deoxyribonucleotide; (9) [5'-2']-deoxyribonucleotide; and (10) [5-3']-dideoxyribonucleotide. Exemplary chemically modified terminal phosphate groups include those shown in FIG. 8.

Conjugates

Modified nucleotides and nucleic acid molecules (e.g., dsNA molecules) as provided herein may include conjugates, for example, a conjugate covalently attached to the chemically-modified nucleic acid molecule. Non-limiting examples of conjugates include conjugates and ligands described in Vargeese et al., U.S. Ser. No. 10/427,160. The conjugate may be covalently attached to a nucleic acid molecule (such as an siNA molecule) via a biodegradable linker. The conjugate molecule may be attached at the 3'-end of either the sense strand, the antisense strand, or both strands of the chemically-modified nucleic acid molecule. The conjugate molecule may be attached at the 5'-end of either the sense strand, the antisense strand, or both strands of the chemically-modified nucleic acid molecule. The conjugate molecule may be attached both the 3'-end and 5'-end of either the sense strand, the antisense strand, or both strands of the chemically-modified nucleic acid molecule, or any combination thereof. In one embodiment, a conjugate molecule may include a molecule that facilitates delivery of a chemically-modified nucleic acid molecule into a biological system, such as a cell. In another embodiment, the conjugate molecule attached to the chemically-modified nucleic acid molecule is a polyethylene glycol, human serum albumin, or a ligand for a cellular receptor that can mediate cellular uptake. Examples of specific conjugate molecules contemplated herein that can be attached to chemically-modified nucleic acid molecules are described in Vargeese et al., U.S. Ser. No. 10/201,394.

Linkers

A nucleic acid molecule provided herein (e.g., an dsNA) molecule may include a nucleotide, non-nucleotide, or mixed nucleotide/non-nucleotide linker that joins the sense region of the nucleic acid to the antisense region of the nucleic acid. A nucleotide linker can be a linker of ≥2 nucleotides in length, for example about 2, 3, 4, 5, 6, 7, 8, 9, or 10 nucleotides in length. The nucleotide linker can be a nucleic acid aptamer. The term "aptamer" or "nucleic acid aptamer" as used herein refers to a nucleic acid molecule that binds specifically to a target molecule wherein the nucleic acid molecule has sequence that includes a sequence recognized by the target molecule in its natural setting. Alternately, an aptamer can be a nucleic acid molecule that binds to a target molecule (such as TLR2 mRNA and TLR4 mRNA) where the target molecule does not naturally bind to a nucleic acid. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art. See e.g., Gold et al.; 1995, Annu Rev. Biochem., 64, 763; Brody and Gold, 2000, J. Biotechnol., 74, 5; Sun, 2000, Curr. Opin. Mol. Ther., 2, 100; Kusser, 2000, J. Biotechnol., 74, 27; Hermann and Patel, 2000, Science, 287, 820; and Jayasena, 1999, Clinical Chemistry, 45, 1628.

A non-nucleotide linker may include an abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, Nucleic Acids Res. 1990, 18:6353 and Nucleic Acids Res. 1987, 15:3113; Cload and Schepartz, J. Am. Chem. Soc. 1991, 113:6324; Richardson and Schepartz, J. Am. Chem. Soc. 1991, 113:5109; Ma et al., Nucleic Acids Res. 1993, 21:2585 and Biochemistry 1993, 32:1751; Durand et al., Nucleic Acids Res. 1990, 18:6353; McCurdy et al., Nucleosides & Nucleotides 1991, 10:287; Jschke et al., Tetrahedron Lett. 1993, 34:301; Ono et al., Biochemistry 1991, 30:9914; Arnold et al., International Publication No. WO 89/02439; Usman et al., International Publication No. WO 95/06731; Dudycz et al., International Publication No. WO 95/11910 and Ferentz and Verdine, J. Am. Chem. Soc. 1991, 113:4000.

5' Ends, 3' Ends and Overhangs

Nucleic acid molecules disclosed herein (e.g., dsNA molecules) may be blunt-ended on both sides, have overhangs on both ends or a combination of blunt and overhang ends. Overhangs may occur on either the 5'- or 3'-end of the sense or antisense strand.

5'- and/or 3'-ends of double-stranded nucleic acid molecules (e.g., dsNA) may be blunt ended or have an overhang. The 5'-end may be blunt ended and the 3'-end has an overhang in either the sense strand or the antisense strand. In other embodiments, the 3'-end may be blunt ended and the 5'-end has an overhang in either the sense strand or the antisense strand. In yet other embodiments, both the 5'- and 3'-end are blunt ended or both the 5'- and 3'-ends have overhangs.

The 5'- and/or 3'-end of one or both strands of the nucleic acid may include a free hydroxyl group. The 5'- and/or 3'-end of any nucleic acid molecule strand may be modified to include a chemical modification. Such modification may stabilize nucleic acid molecules, e.g., the 3'-end may have increased stability due to the presence of the nucleic acid molecule modification. Examples of end modifications (e.g., terminal caps) include, but are not limited to, abasic, deoxy abasic, inverted (deoxy) abasic, glyceryl, dinucleotide, acyclic nucleotide, amino, fluoro, chloro, bromo, CN, CF, methoxy, imidazole, carboxylate, thioate, $C_1$ to $C_{10}$ lower alkyl, substituted lower alkyl, alkaryl or aralkyl, $OCF_3$, OCN, O-, S-, or N-alkyl; O-, S-, or N-alkenyl; $SOCH_3$; $SO_2CH_3$; $ONO_2$; $NO_2$, $N_3$; heterocycloalkyl; heterocycloalkaryl; aminoalkylamino; polyalkylamino or substituted silyl, as, among others, described in European patents EP 586,520 and EP 618,925 and other modifications disclosed herein.

Nucleic acid molecules include those with blunt ends, i.e., ends that do not include any overhanging nucleotides. A nucleic acid molecule can include one or more blunt ends. The blunt ended nucleic acid molecule has a number of base pairs equal to the number of nucleotides present in each strand of the nucleic acid molecule. The nucleic acid molecule can include one blunt end, for example where the 5'-end of the antisense strand and the 3'-end of the sense strand do not have any overhanging nucleotides. Nucleic acid molecule may include one blunt end, for example where the 3'-end of the antisense strand and the 5'-end of the sense strand do not have any overhanging nucleotides. A nucleic acid molecule may include two blunt ends, for example where the 3'-end of the antisense strand and the 5'-end of the sense strand as well as the 5'-end of the antisense strand and 3'-end of the sense strand do not have any overhanging nucleotides. Other nucleotides present in a blunt ended nucleic acid molecule can include, for example, mismatches, bulges, loops, or wobble base pairs to modulate the activity of the nucleic acid molecule, e.g. to mediate RNA interference.

In certain embodiments of the nucleic acid molecules (e.g., dsNA molecules) provided herein, at least one end of the molecule has an overhang of at least one nucleotide (for example 1 to 8 overhang nucleotides). For example, one or both strands of a double-stranded nucleic acid molecule disclosed herein may have an overhang at the 5'-end or at the 3'-end or both. An overhang may be present at either or both the sense strand and antisense strand of the nucleic acid molecule. The length of the overhang may be as little as one nucleotide and as long as 1 to 8 or more nucleotides (e.g., 1, 2, 3, 4, 5, 6, 7 or 8 nucleotides; in some preferred embodiments an overhang is 2, 3, 4, 5, 6, 7 or 8 nucleotides; for example an overhang may be 2 nucleotides. The nucleotide(s) forming the overhang may be include deoxyribonucleotide(s), ribonucleotide(s), natural and non-natural nucleobases or any nucleotide modified in the sugar, base or phosphate group, such as disclosed herein. A double-stranded nucleic acid molecule may have both 5'- and 3'-overhangs. The overhangs at the 5'- and 3'-end may be of different lengths. A overhang may include at least one nucleic acid modification which may be deoxyribonucleotide. One or more deoxyribonucleotides may be at the 5'-terminus. The 3'-end of the respective counter-strand of the nucleic acid molecule may not have an overhang, more preferably not a deoxyribonucleotide overhang. The one or more deoxyribonucleotide may be at the 3'-terminus. The 5'-end of the respective counter-strand of the dsRNA may not have an overhang, more preferably not a deoxyribonucleotide overhang. The overhang in either the 5'- or the 3'-end of a strand may be 1 to 8 (e.g., about 1, 2, 3, 4, 5, 6, 7 or 8) unpaired nucleotides, preferably, the overhang is 2-3 unpaired nucleotides; more preferably 2 unpaired nucleotides. Nucleic acid molecules may include duplex nucleic acid molecules with overhanging ends of about 1 to about 20 (e.g., about 1, 2, 3, 4, 5, 6, 7, 8, 9, 10, 11, 12, 13, 1, 15, 16, 17, 18, 19 or 20); preferably 1-8 (e.g., about 1, 2, 3, 4, 5, 6, 7 or 8) nucleotides, for example, about 21-nucleotide duplexes with about 19 base pairs and 3'-terminal mononucleotide, dinucleotide, or trinucleotide overhangs. Nucleic acid molecules provided herein may include duplex nucleic acid molecules with blunt ends, where both ends are blunt, or alternatively, where one of the ends is blunt. Nucleic acid molecules disclosed herein can include one or more blunt ends, i.e. where a blunt end does not have any overhanging nucleotides. In one embodiment, the blunt ended nucleic acid molecule has a number of base pairs equal to the number of nucleotides present in each strand of the nucleic acid molecule. The nucleic acid molecule may include one blunt end, for example where the 5'-end of the antisense strand and the 3'-end of the sense strand do not have any overhanging nucleotides. The nucleic acid molecule may include one blunt end, for example where the 3'-end of the antisense strand and the 5'-end of the sense strand do not have any overhanging nucleotides. A nucleic acid molecule may include two blunt ends, for example where the 3'-end of the antisense strand and the 5'-end of the sense strand as well as the 5'-end of the antisense strand and 3'-end of the sense strand do not have any overhanging nucleotides. In certain preferred embodiments the nucleic acid compounds are blunt ended. Other nucleotides present in a blunt ended dsNA molecule can include, for example, mismatches, bulges, loops, or wobble base pairs to modulate the activity of the nucleic acid molecule to mediate RNA interference.

In many embodiments one or more, or all, of the overhang nucleotides of a nucleic acid molecule (e.g., a dsNA molecule) as described herein includes are modified such as described herein; for example one or more, or all, of the nucleotides may be 2'-deoxynucleotides.

Amount, Location and Patterns of Modifications of Nucleic Acid Compounds

Nucleic acid molecules (e.g., dsNA molecules) disclosed herein may include modified nucleotides as a percentage of the total number of nucleotides present in the nucleic acid molecule. As such, a nucleic acid molecule may include about 5% to about 100% modified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% modified nucleotides). The actual percentage of modified nucleotides present in a given nucleic acid molecule will depend on the total number of nucleotides present in the nucleic acid. If the nucleic acid molecule is single stranded, the percent modification can be based upon the total number of nucleotides present in the single stranded nucleic acid molecule. Likewise, if the nucleic acid molecule is double-stranded, the percent modification can be based upon the total number of nucleotides present in the sense strand, antisense strand, or both the sense and antisense strands.

Nucleic acid molecules disclosed herein may include unmodified RNA as a percentage of the total nucleotides in the nucleic acid molecule. As such, a nucleic acid molecule may include about 5% to about 100% unmodified nucleotides (e.g., about 5%, 10%, 15%, 20%, 25%, 30%, 35%, 40%, 45%, 50%, 55%, 60%, 65%, 70%, 75%, 80%, 85%, 90%, 95% or 100% of total nucleotides present in a nucleic acid molecule).

A nucleic acid molecule (e.g., an dsNA molecule) may include a sense strand that includes about 1 to about 5, specifically about 1, 2, 3, 4, or 5 phosphorothioate internucleotide linkages, and/or one or more (e.g., about 1, 2, 3, 4, 5, or more) 2'-deoxy, 2'-O-methyl, 2'-deoxy-2'-fluoro, and/or one or more (e.g., about 1, 2, 3, 4, 5, or more) universal base modified nucleotides, and optionally a terminal cap molecule at the 3-end, the 5'-end, or both of the 3'- and 5'-ends of the sense strand; and wherein the antisense strand includes about 1 to about 5 or more, specifically about 1, 2, 3, 4, 5, or more phosphorothioate internucleotide linkages, and/or one or more (e.g., about 1, 2, 3, 4, 5, 6, 7, 8, 9, 10 or more) 2'-deoxy, 2'-O-methyl, 2'-deoxy-2'-fluoro, and/or one or more (e.g., about 1, 2, 3, 4, 5, 6, 7, 8, 9, 10 or more) universal base modified nucleotides, and optionally a terminal cap molecule at the 3'-end, the 5'-end, or both of the 3'- and 5'-ends of the antisense strand. A nucleic acid molecule may include about 1, 2, 3, 4, 5, 6, 7, 8, 9, 10, or more, pyrimidine nucleotides of the sense and/or antisense nucleic acid strand are chemically-modified with 2'-deoxy, 2'-O-methyl and/or 2'-deoxy-2'-fluoro nucleotides, with or without about 1 to about 5 or more, for example about 1, 2, 3, 4, 5, or more phosphorothioate internucleotide linkages and/or a terminal cap molecule at the 3'-end, the 5'-end, or both of the 3'- and 5'-ends, being present in the same or different strand.

A nucleic acid molecule may include about 1 to about 5 or more (specifically about 1, 2, 3, 4, 5 or more) phosphorothioate internucleotide linkages in each strand of the nucleic acid molecule.

A nucleic acid molecule may include 2'-5' internucleotide linkages, for example at the 3'-end, the 5'-end, or both of the 3'-end and 5'-end of one or both nucleic acid sequence strands. In addition, the 2'-5' internucleotide linkage(s) can be present at various other positions within one or both nucleic acid sequence strands, for example, about 1, 2, 3, 4, 5, 6, 7, 8, 9, 10, or more including every internucleotide linkage of a pyrimidine nucleotide in one or both strands of the siNA molecule can include a 2'-5' internucleotide linkage, or about 1, 2, 3, 4, 5, 6, 7, 8, 9, 10, or more including every internucleotide linkage of a purine nucleotide in one or both strands of the siNA molecule can include a 2'-5' internucleotide linkage.

A chemically-modified short interfering nucleic acid (dsNA) molecule may include an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-deoxy purine nucleotides (e.g., wherein all purine nucleotides are 2'-deoxy purine nucleotides or alternately a plurality of purine nucleotides are 2'-deoxy purine nucleotides).

A chemically-modified short interfering nucleic acid (dsNA) molecule may include an antisense region, wherein any (e.g., one or more or all) pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and wherein any (e.g., one or more or all) purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides).

A chemically-modified short interfering nucleic acid (dsNA) molecule capable of mediating RNA interference (RNAi) against TLR2 and/or TLR4 inside a cell or reconstituted in vitro system may include a sense region, wherein one or more pyrimidine nucleotides present in the sense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the sense region are 2'-deoxy purine nucleotides (e.g., wherein all purine nucleotides are 2'-deoxy purine nucleotides or alternately a plurality of purine nucleotides are 2'-deoxy purine nucleotides), and an antisense region, wherein one or more pyrimidine nucleotides present in the antisense region are 2'-deoxy-2'-fluoro pyrimidine nucleotides (e.g., wherein all pyrimidine nucleotides are 2'-deoxy-2'-fluoro pyrimidine nucleotides or alternately a plurality of pyrimidine nucleotides are 2'-deoxy-2'-fluoro pyrimidine nucleotides), and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). The sense region and/or the antisense region can have a terminal cap modification, such as any modification, that is optionally present at the 3'-end, the 5'-end, or both of the 3'-end and the 5'-end of the sense and/or antisense sequence. The sense and/or antisense region can optionally further include a 3'-terminal nucleotide overhang having about 1 to about 4 (e.g., about 1, 2, 3, or 4) 2'-deoxyribonucleotides. The overhang nucleotides can further include one or more (e.g., about 1, 2, 3, 4 or more) phosphorothioate, phosphonoacetate, and/or thiophosphonoacetate internucleotide linkages. The purine nucleotides in the sense region may alternatively be 2'-O-methyl purine nucleotides (e.g., wherein all purine nucleotides are 2'-O-methyl purine nucleotides or alternately a plurality of purine nucleotides are 2'-O-methyl purine nucleotides) and one or more purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). One or more purine nucleotides in the sense region may alternatively be purine ribonucleotides (e.g., wherein all purine nucleotides are purine ribonucleotides or alternately a plurality of purine nucleotides are purine ribonucleotides) and any purine nucleotides present in the antisense region are 2'-O-methyl purine nucleotides (e.g., wherein all purine nucleotides are 2'-O-methyl purine nucleotides or alternately a plurality of purine nucleotides are 2'-O-methyl purine nucleotides). One or more purine nucleotides in the sense region and/or present in the antisense region may alternatively be selected from the group consisting of 2'-deoxy nucleotides, locked nucleic acid (LNA) nucleotides, 2'-methoxyethyl nucleotides, 4'-thionucleotides, and 2'-O-methyl nucleotides (e.g., wherein all purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides or alternately a plurality of purine nucleotides are selected from the group consisting of 2'-deoxy nucleotides, locked nucleic acid (LNA) nucleotides, 2'-methoxyethyl nucleotides, 4'-thionucleotides, and 2'-O-methyl nucleotides).

In some embodiments, a nucleic acid molecule (e.g., a dsNA molecule) as described herein includes a modified nucleotide (for example one modified nucleotide) in the antisense strand; for example in position 6 or position 7 of the antisense strand.

Modification Patterns and Alternating Modifications of Nucleic Acid Compounds

Nucleic acid molecules (e.g., dsNA molecules) provided herein may have patterns of modified and unmodified nucleic acids. A pattern of modification of the nucleotides in a contiguous stretch of nucleotides may be a modification contained within a single nucleotide or group of nucleotides that are covalently linked to each other via standard phosphodiester bonds or, at least partially, through phosphorothioate bonds. Accordingly, a "pattern" as contemplated herein, does not necessarily need to involve repeating units, although it may. Examples of modification patterns that may be used in conjunction with the nucleic acid molecules (e.g., dsNA molecules) provided herein include those disclosed in Giese, U.S. Pat. No. 7,452,987. For example, nucleic acid molecules (e.g., dsNA molecules) provided herein include those having modification patterns such as, similar to, or the same as, the patterns shown diagrammatically in FIG. 2 of the Giese U.S. Pat. No. 7,452,987.

A modified nucleotide or group of modified nucleotides may be at the 5'-end or the 3'-end of the sense strand or the antisense strand, a flanking nucleotide or group of nucleotides is arrayed on both sides of the modified nucleotide or group, where the flanking nucleotide or group either is unmodified or does not have the same modification of the preceding nucleotide or group of nucleotides. The flanking nucleotide or group of nucleotides may, however, have a different modification. This sequence of modified nucleotide or group of modified nucleotides, respectively, and unmodified or differently modified nucleotide or group of unmodified or differently modified nucleotides may be repeated one or more times.

In some patterns, the 5'-terminal nucleotide of a strand is a modified nucleotide while in other patterns the 5'-terminal nucleotide of a strand is an unmodified nucleotide. In some patterns, the 5'-end of a strand starts with a group of modified nucleotides while in other patterns, the 5'-terminal end is an unmodified group of nucleotides. This pattern may be either on the first stretch or the second stretch of the nucleic acid molecule or on both.

Modified nucleotides of one strand of the nucleic acid molecule may be complementary in position to the modified or unmodified nucleotides or groups of nucleotides of the other strand.

There may be a phase shift between modifications or patterns of modifications on one strand relative to the pattern of modification of the other strand such that the modification groups do not overlap. In one instance, the shift is such that the modified group of nucleotides of the sense strand corresponds to the unmodified group of nucleotides of the antisense strand and vice versa.

There may be a partial shift of the pattern of modification such that the modified groups overlap. The groups of modified nucleotides in any given strand may optionally be the same length, but may be of different lengths. Similarly, groups of unmodified nucleotides in any given strand may optionally be the same length, or of different lengths.

In some patterns, the second (penultimate) nucleotide at the terminus of the strand, is an unmodified nucleotide or the beginning of group of unmodified nucleotides. Preferably, this unmodified nucleotide or unmodified group of nucleotides is located at the 5'-end of the either or both the sense strand and the antisense strand and even more preferably at the terminus of the sense strand. An unmodified nucleotide or unmodified group of nucleotide may be located at the 5'-end of the sense strand. In one embodiment the pattern consists of alternating single modified and unmodified nucleotides.

In some double-stranded nucleic acid molecules a 2'-O-methyl modified nucleotide and a non-modified nucleotide or a nucleotide which is not 2'-O-methyl modified, are incorporated on both strands in an alternating fashion, resulting in a pattern of alternating 2'-O-methyl modified nucleotides and nucleotides that are either unmodified or at least do not include a 2'-O-methyl modification. In certain embodiments, the same sequence of 2'-O-methyl modification and non-modification exists on the second strand; in other embodiments the alternating 2'-O-methyl modified nucleotides are only present in the sense strand and are not present in the antisense strand; and in yet other embodiments the alternating 2'-O-methyl modified nucleotides are only present in the antisense strand and are not present in the sense strand. In certain embodiments, there is a phase shift between the two strands such that the 2'-O-methyl modified nucleotide on the first strand base pairs with a non-modified nucleotide(s) on the second strand and vice versa. This particular arrangement, i.e. base pairing of 2'-O-methyl modified and non-modified nucleotide(s) on both strands is particularly preferred in certain embodiments. In certain embodiments, the pattern of alternating 2'-O-methyl modified nucleotides exists throughout the entire nucleic acid molecule; or the entire duplex region. In other embodiments the pattern of alternating 2'-O-methyl modified nucleotides exists only in a portion of the nucleic acid; or portion of the duplex region.

In "phase shift" patterns, it may be preferred if the antisense strand starts with a 2'-O-methyl modified nucleotide at the 5' end whereby consequently the second nucleotide is non-modified, the third, fifth, seventh and so on nucleotides are thus again 2'-O-methyl modified whereas the second, fourth, sixth, eighth and the like nucleotides are non-modified nucleotides.

Exemplary Modification Locations and Patterns of Nucleic Acid Compounds

While exemplary patterns are provided in more detail below, all permutations of patterns with all possible characteristics of the nucleic acid molecules disclosed herein and those known in the art are contemplated (e.g., characteristics include, but are not limited to, length of sense strand, length of antisense strand, length of duplex region, length of hangover, whether one or both ends of a double-stranded nucleic acid molecule is blunt or has an overhang, location of modified nucleic acid, number of modified nucleic acids, types of modifications, whether a double overhang nucleic acid molecule has the same or different number of nucleotides on the overhang of each side, whether a one or more than one type of modification is used in a nucleic acid molecule, and number of contiguous modified/unmodified nucleotides). With respect to all detailed examples provided below, while the duplex region is shown to be 19 nucleotides, the nucleic acid molecules provided herein can have a duplex region ranging from 1 to 40 nucleotides in length as each strand of a duplex region can independently be 17-40 nucleotides in length Exemplary patterns are provided herein.

Nucleic acid molecules may have a blunt end on both ends that include a single or contiguous set of modified nucleic acids. The modified nucleic acid may be located at any position along either the sense or antisense strand. Nucleic acid molecules may include a group of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 contiguous modified nucleotides. Modified nucleic acids may make up 1%, 2%, 3%, 5%, 10%, 15%, 20%, 25%, 30%, 35%, 40%, 45%, 50%, 55%, 60%, 65%, 70%, 75%, 80%, 85%, 90%, 95%, 97%, 98% or 100% of a nucleic acid strand. Modified nucleic acids of the examples immediately below may be in the sense strand only, the antisense strand only, or in both the sense strand and the antisense strand.

Nicks and Gaps in Nucleic Acid Strands

Nucleic acid molecules (e.g., siNA molecules) provided herein may have a strand, preferably the sense strand, that is nicked or gapped. As such, nucleic acid molecules may have three or more strand, for example, such as a meroduplex RNA (mdRNA) disclosed in International Patent Application No. PCT/US07/081836. Nucleic acid molecules with a nicked or gapped strand may be RISC length (e.g., about 15 to 25 nucleotides) or Dicer substrate length (e.g., about 25 to 30 nucleotides).

Dicer Substrates

In certain embodiments, the nucleic acid molecules (e.g., siNA molecules) provided herein may be a precursor "Dicer substrate" molecule, e.g., double-stranded nucleic acid, processed in vivo to produce an active nucleic acid molecules, for example as described in Rossi, US Patent App. No. 20050244858. In certain conditions and situations, it has been found that these relatively longer dsRNA siNA species, e.g., of from about 25 to about 30 nucleotides, can give unexpectedly effective results in terms of potency and duration of action. Without wishing to be bound by any particular theory, it is thought that the longer dsRNA species serve as a substrate for the enzyme Dicer in the cytoplasm of a cell. In addition to cleaving double-stranded nucleic acid into shorter segments, Dicer may facilitate the incorporation of a single-stranded cleavage product derived from the cleaved dsRNA into the RNA-induced silencing complex (RISC complex) that is responsible for the destruction of the cytoplasmic RNA derived from the target gene.

Dicer substrates may have certain properties which enhance its processing by Dicer. Dicer substrates are of a length sufficient such that it is processed by Dicer to produce an active nucleic acid molecule and may further include one or more of the following properties: (i) the dsRNA is asymmetric, e.g., has a 3' overhang on the first strand (antisense strand) and (ii) the dsRNA has a modified 3' end on the second strand (sense strand) to direct orientation of Dicer binding and processing of the dsRNA to an active siRNA. In certain embodiments, the longest strand in the Dicer substrate may be 24-30 nucleotides.

Dicer substrates may be symmetric or asymmetric. The Dicer substrate may have a sense strand that includes 22-28 nucleotides and an antisense strand that may include 24-30 nucleotides; thus, in some embodiments the resulting Dicer substrate may have an overhang on the 3' end of the antisense strand. Dicer substrate may have a sense strand 25 nucleotides in length, and an antisense strand having 27 nucleotides in length with a 3'-overhang. The overhang may be 1-3 nucleotides, for example 2 nucleotides. The sense strand may also have a 5' phosphate.

Like other siNA molecules provided herein, the antisense strand of a Dicer substrate may have any sequence that anneals to the antisense strand under biological conditions, such as within the cytoplasm of a eukaryotic cell.

Dicer substrates may have any modifications to the nucleotide base, sugar or phosphate backbone as known in the art and/or as described herein for other nucleic acid molecules (such as siNA molecules). In certain embodiments, Dicer substrates may have a sense strand that is modified for Dicer processing by suitable modifiers located at the 3' end of the sense strand, i.e., the dsRNA is designed to direct orientation of Dicer binding and processing. Suitable modifiers include nucleotides such as deoxyribonucleotides, dideoxyribonucleotides, acyclonucleotides and the like and sterically hindered molecules, such as fluorescent molecules and the like. Acyclonucleotides substitute a 2-hydroxyethoxymethyl group for the 2'-deoxyribofuranosyl sugar normally present in deoxynucleoside monophosphates (dNMPs). Other nucleotide modifiers that could be used in Dicer substrate siNA molecules include 3'-deoxyadenosine (cordycepin), 3'-azido-3'-deoxythymidine (AZT), 2',3'-dideoxyinosine (ddI), 2',3'-dideoxy-3'-thiacytidine (3TC), 2',3'-didehydro-2',3'-dideoxythymidine (d4T) and the monophosphate nucleotides of 3'-azido-3'-deoxythymidine (AZT), 2',3'-dideoxy-3'-thiacytidine (3TC) and 2',3'-didehydro-2',3'-dideoxythymidine (d4T). In one embodiment, deoxynucleotides are used as the modifiers. When nucleotide modifiers are utilized, they may replace ribonucleotides (e.g., 1-3 nucleotide modifiers, or 2 nucleotide modifiers are substituted for the ribonucleotides on the 3' end of the sense strand) such that the length of the Dicer substrate does not change. When sterically hindered molecules are utilized, they may be attached to the ribonucleotide at the 3' end of the antisense strand. Thus, in certain embodiments the length of the strand does not change with the incorporation of the modifiers. In certain embodiments, two DNA bases in the dsRNA are substituted to direct the orientation of Dicer processing of the antisense strand. In a further embodiment, two terminal DNA bases are substituted for two ribonucleotides on the 3'-end of the sense strand forming a blunt end of the duplex on the 3' end of the sense strand and the 5' end of the antisense strand, and a two-nucleotide RNA overhang is located on the 3'-end of the antisense strand. This is an asymmetric composition with DNA on the blunt end and RNA bases on the overhanging end.

In certain embodiments modifications are included in the Dicer substrate such that the modification does not prevent the nucleic acid molecule from serving as a substrate for Dicer. In one embodiment, one or more modifications are made that enhance Dicer processing of the Dicer substrate. One or more modifications may be made that result in more effective RNAi generation. One or more modifications may be made that support a greater RNAi effect. One or more modifications are made that result in greater potency per each Dicer substrate to be delivered to the cell. Modifications may be incorporated in the 3'-terminal region, the 5'-terminal region, in both the 3'-terminal and 5'-terminal region or at various positions within the sequence. Any number and combination of modifications can be incorporated into the Dicer substrate so long as the modification does not prevent the nucleic acid molecule from serving as a substrate for Dicer. Where multiple modifications are present, they may be the same or different. Modifications to bases, sugar moieties, the phosphate backbone, and their combinations are contemplated. Either 5'-terminus can be phosphorylated.

The sense and antisense strands of the Dicer substrate are not required to be completely complementary. They only need to be substantially complementary to anneal under biological conditions and to provide a substrate for Dicer that produces an siRNA sufficiently complementary to the target sequence.

A region of one of the strands, particularly the antisense strand, of the Dicer substrate may have a sequence length of at least 19 nucleotides, wherein these nucleotides are in the 21-nucleotide region adjacent to the 3' end of the antisense strand and are sufficiently complementary to a nucleotide sequence of the RNA produced from the target gene. A Dicer substrate may also have one or more of the following additional properties: (a) the antisense strand has a right shift from a corresponding 21-mer (i.e., the antisense strand includes nucleotides on the right side of the molecule when compared to the corresponding 21-mer), (b) the strands may not be completely complementary, i.e., the strands may contain simple mismatch pairings and (c) base modifications such as locked nucleic acid(s) may be included in the 5' end of the sense strand.

An antisense strand of a Dicer substrate nucleic acid molecule may be modified to include 1-9 ribonucleotides on the 5'-end to give a length of 22-28 nucleotides. When the antisense strand has a length of 21 nucleotides, then 1-7 ribonucleotides, or 2-5 ribonucleotides and or 4 ribonucleotides may be added on the 3'-end. The added ribonucleotides may have any sequence. Although the added ribonucleotides may be complementary to the target gene sequence, full complementarity between the target sequence and the antisense strands is not required. That is, the resultant antisense strand is sufficiently complementary with the target sequence. A sense strand may then have 24-30 nucleotides. The sense strand may be substantially complementary with the antisense strand to anneal to the antisense strand under biological conditions. In one embodiment, the antisense strand may be synthesized to contain a modified 3'-end to direct Dicer processing. The sense strand may have a 3' overhang. The antisense strand may be synthesized to contain a modified 3'-end for Dicer binding and processing and the sense strand may have a 3' overhang.

Methods and Compositions for Inhibiting TLR2 and TLR4

In various aspects provided are compositions and methods for inhibition of TLR2 expression for treatment of lung disease, disorder or injury in a mammal. In various embodiments the method comprises administering to the mammal at least one therapeutic agent selected from a TLR2 inhibitor or a pharmaceutically acceptable salt or prodrug thereof; in an amount effect to treat the mammal. In various embodiments the therapeutic agent is selected from the group consisting of a small molecule chemical compound; a protein; an antibody or fragment thereof; and a nucleic acid molecule.

In various aspects provided are compositions and methods for inhibition of TLR2 and TLR4 expression for the treatment of lung disease, disorder or injury in a mammal. In various embodiments the method comprises administering to the mammal at least two therapeutic agents selected from: (i) a TLR2 inhibitor or a pharmaceutically acceptable salt or prodrug thereof and (ii) a TLR4 inhibitor or a pharmaceutically acceptable salt or prodrug thereof; in an amount effective to treat the mammal. In various embodiments each therapeutic agent is independently selected from the group consisting of a small molecule chemical compound; a protein; an antibody or fragment thereof; and a nucleic acid molecule.

In some embodiments, the therapeutic agent is a combined inhibitor by which it is meant a single agent which is capable of inhibiting the expression and/or activity of at least two genes and/or gene products of both: TLR2 and TLR4. Non-limiting examples of such single agents are tandem and multi-armed RNAi molecules disclosed in PCT Patent Publication No. WO 2007/091269.

In some embodiments a small nucleic acid molecule is selected from a short interfering nucleic acid (siNA), double-stranded nucleic acid (dsNA), interfering RNA (RNAi), short interfering RNA (siRNA), double-stranded RNA (dsRNA), micro-RNA (miRNA), and short hairpin RNA (shRNA) molecules capable of mediating or that mediate RNA interference against TLR2 and TLR4 gene expression. The composition and methods disclosed herein are also useful in treating or preventing inflammation and/or graft rejection associated with organ transplantation, in particular lung transplantation, including treatment, prevention or attenuation of progression of primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD) after organ transplantation, in particular lung transplantation.

Nucleic acid molecule(s) and/or methods provided herein may be used to down regulate the expression of gene(s) that encode RNA referred to, by example, Genbank Accession numbers NM_003264.3 (TLR2), NR_024169.1 (TLR4), NM_138554.3 (TLR4) and NR_024168.1 (TLR4).

Compositions, methods and kits provided herein may include one or more nucleic acid molecules (e.g., dsNA) and methods that independently or in combination modulate (e.g., down-regulate) the expression of TLR2 and TLR4 protein and/or genes encoding TLR2 and TLR4 proteins associated with the maintenance and/or development of diseases, conditions or disorders such as acute respiratory distress syndrome (ARDS), acute lung injury, pulmonary fibrosis (idiopathic), bleomycin induced pulmonary fibrosis, mechanical ventilation induced lung injury, chronic obstructive pulmonary disease (COPD), chronic bronchitis, emphysema, primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD) after organ transplantation, in particular in lung transplant (e.g., genes encoding sequences comprising those sequences referred to by GenBank Accession Nos. NM_003264.3, NR_024169.1, NM_138554.3 and NR_024168.1, or a TLR2 and TLR4 gene family member where the genes or gene family sequences share sequence homology). The description of the various aspects and embodiments is provided with reference to exemplary genes TLR2 and TLR4. However, the various aspects and embodiments are also directed to other related TLR2 and TLR4 genes, such as homolog genes and transcript variants, and polymorphisms (e.g., single nucleotide polymorphism, (SNPs)) associated with certain TLR2 and TLR4 genes. As such, the various aspects and embodiments are also directed to other genes that are involved in TLR2 and TLR4 mediated pathways of signal transduction or gene expression that are involved, for example, in the maintenance or development of diseases, traits, or conditions described herein. These additional genes can be analyzed for target sites using the methods described for the TLR2 and TLR4 genes herein. Thus, the modulation of other genes and the effects of such modulation of the other genes can be performed, determined, and measured as described herein.

In one embodiment, compositions and methods provided herein include a double-stranded short interfering nucleic acid (dsNA) molecule that down-regulates expression of TLR2 gene (e.g., human TLR2 exemplified by SEQ ID NO:1), where the nucleic acid molecule includes about 17 to about 40 base pairs.

In one embodiment, compositions and methods provided herein include a double-stranded short interfering nucleic acid (dsNA) molecules that down-regulates expression of TLR2 gene and TLR4 gene (e.g., human TLR2 exemplified by SEQ ID NO:1 and human TLR4 exemplified by SEQ ID NO:2, SEQ ID NO:3 or SEQ ID NO:4), where the nucleic acid molecules includes about 17 to about 40 base pairs.

In one embodiment, a nucleic acid disclosed herein may be used to inhibit the expression of the TLR2 and/or TLR4 gene or a TLR2 and/or TLR4 gene family where the genes or gene family sequences share sequence homology. Such homologous sequences can be identified as is known in the art, for example using sequence alignments. Nucleic acid molecules can be designed to target such homologous sequences, for example using perfectly complementary sequences or by incorporating non-canonical base pairs, for example mismatches and/or wobble base pairs, that can provide additional target sequences. In instances where mismatches are identified, non-canonical base pairs (for example, mismatches and/or wobble bases) can be used to generate nucleic acid molecules that target more than one gene sequence. In a non-limiting example, non-canonical base pairs such as UU and CC base pairs are used to generate nucleic acid molecules that are capable of targeting sequences for differing TLR2 and/or TLR4 targets that share sequence homology. As such, one advantage of using dsRNAs disclosed herein is that a single nucleic acid can be designed to include nucleic acid sequence that is complementary to the nucleotide sequence that is conserved between the homologous genes. In this approach, a single nucleic acid can be used to inhibit expression of more than one gene instead of using more than one nucleic acid molecule to target the different genes.

Nucleic acid molecules may be used to target conserved sequences corresponding to a gene family or gene families such as TLR2 and/or TLR4 family genes. As such, nucleic acid molecules targeting multiple TLR2 and/or TLR4 targets can provide increased therapeutic effect. In addition, nucleic acid can be used to characterize pathways of gene function in a variety of applications. For example, nucleic acid molecules can be used to inhibit the activity of target gene(s) in a pathway to determine the function of uncharacterized gene(s) in gene function analysis, mRNA function analysis, or translational analysis. The nucleic acid molecules can be used to determine potential target gene pathways involved in various diseases and conditions toward pharmaceutical development. The nucleic acid molecules can be used to understand pathways of gene expression involved in, for example acute respiratory distress syndrome (ARDS), acute lung injury, pulmonary fibrosis (idiopathic), bleomycin induced pulmonary fibrosis, mechanical ventilation induced lung injury, chronic obstructive pulmonary disease (COPD), chronic bronchitis, emphysema, bronchiolitis obliterans after lung transplantation, and/or inflammation and/or graft rejection, associated with organ transplantation-induced acute graft dysfunction, in particular lung transplantation-induced acute graft dysfunction.

In one embodiment, the compositions and methods provided herein include a nucleic acid molecule having RNAi activity against TLR2. In another embodiment, the compositions and methods provided herein include a nucleic acid molecule having RNAi activity against TLR2 RNA and a nucleic acid molecule having RNAi activity against TLR4 RNA, where the nucleic acid molecule includes a sequence complementary to any RNA having TLR2 and/or TLR4 encoding sequence. In another embodiment, a nucleic acid molecule may have RNAi activity against TLR2 and/or TLR4 RNA, where the nucleic acid molecule includes a sequence complementary to an RNA having variant TLR2 and/or TLR4 encoding sequence, for example other mutant TLR2 and/or TLR4 genes known in the art to be associated with the maintenance and/or development of lung disease, disorder or injury as described herein. In another embodiment, a nucleic acid molecule disclosed herein includes a nucleotide sequence that can interact with nucleotide sequence of a TLR2 and/or TLR4 gene and thereby mediate silencing of TLR2 and/or TLR4, respectively, gene expression, for example, wherein the nucleic acid molecule mediates regulation of TLR2 and/or TLR4 gene expression by cellular processes that modulate the chromatin structure or methylation patterns of the TLR2 and/or TLR4 gene and prevent transcription of the TLR2 and/or TLR4 gene.

Antibody Therapy

In some embodiments the inhibitor or therapeutic agent as provided herein comprises and antibody. It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab)$_2$ fragments. Further included within the scope of the provided methods and compositions are chimeric antibodies; human and humanized antibodies; recombinant and engineered antibodies, and fragments thereof. Furthermore, the DNA encoding the variable region of the antibody can be inserted into the DNA encoding other antibodies to produce chimeric antibodies (see, for example, U.S. Pat. No. 4,816, 567). Single chain antibodies fall within the scope of the present inventions. Single chain antibodies can be single chain composite polypeptides having antigen binding capabilities and comprising amino acid sequences homologous or analogous to the variable regions of an immunoglobulin light and heavy chain (linked VH-VL or single chain Fv (ScFv)). Both $V_H$ and $V_L$ may copy natural monoclonal antibody sequences or one or both of the chains may comprise a CDR-FR construct of the type described in U.S. Pat. No. 5,091,513, the entire contents of which are hereby incorporated herein by reference. The separate polypeptides analogous to the variable regions of the light and heavy chains are held together by a polypeptide Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091,513 and 5,096,815, the entire contents of each of which are hereby incorporated herein by reference.

Additionally, CDR grafting may be performed to alter certain properties of the antibody molecule including affinity or specificity. A non-limiting example of CDR grafting is disclosed in U.S. Pat. No. 5,225,539.

Methods of Treatment

Provided herein is a method for treating a lung disorder or injury in a mammal in need thereof comprising administering to the mammal at least one therapeutic agent selected from a TLR2 inhibitor or a pharmaceutically acceptable salt or prodrug; in an amount effect to treat the mammal.

In various embodiments the therapeutic agent is selected from the group consisting of a small molecule chemical compound; a protein; an antibody or fragment thereof; a peptide, a peptidomimetic and a nucleic acid molecule.

Provided herein is a method for treating a lung disorder or injury in a mammal in need thereof comprising administering to the mammal at least two therapeutic agents selected from: (i) at least one TLR2 inhibitor or a pharmaceutically acceptable salt or prodrug thereof and (ii) at least one TLR4 inhibitor or a pharmaceutically acceptable salt or prodrug thereof; in an amount effective to treat the mammal. In some embodiments the therapeutic agent is a combined inhibitor by which it is meant a single agent which is capable of inhibiting the expression and/or activity of both TLR2 gene or gene products thereof and TLR4 gene or gene products thereof.

In various embodiments each therapeutic agent is independently selected from the group consisting of a small molecule chemical compound; a protein; an antibody or fragment thereof; a peptide, a peptidomimetic and a nucleic acid molecule.

In one embodiment, nucleic acid molecules may be used to down-regulate or inhibit the expression of TLR2 and TLR4 proteins arising from TLR2 and TLR4 haplotype polymorphisms that are associated with a disease or condition, (e.g. lung disease, disorder or injury as described herein). Analysis of TLR2 and TLR4 genes, or TLR2 and TLR4 protein or RNA levels can be used to identify subjects with such polymorphisms or those subjects who are at risk of developing traits, conditions, or diseases described herein. These subjects are amenable to treatment, for example, treatment with nucleic acid molecules disclosed herein and any other composition useful in treating diseases related to TLR2 and/or TLR4 gene expression. As such, analysis of TLR2 and/or TLR4 protein or RNA levels can be used to determine treatment type and the course of therapy in treating a subject. Monitoring of TLR2 and/or TLR4 protein or RNA levels can be used to predict treatment outcome and to determine the efficacy of compounds and compositions that modulate the level and/or activity of certain TLR2 and/or TLR4 proteins associated with a trait, condition, or disease described herein.

In preferred embodiments the subject being treated is a warm-blooded animal and, in particular, mammals including human and non-human primates.

Provided are compositions and methods for inhibition of TLR2 and TLR4 expression by using small nucleic acid molecules as provided herein, such as short interfering nucleic acid (siNA), double-stranded nucleic acid (dsNA), interfering RNA (RNAi), short interfering RNA (siRNA), double-stranded RNA (dsRNA), micro-RNA (miRNA), and short hairpin RNA (shRNA) molecules capable of mediating or that mediate RNA interference against TLR2 and/or TLR4 gene expression. The composition and methods disclosed herein are also useful in treating various lung disorders and injury such as acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema, bronchiolitis obliterans after lung transplantation and lung transplantation-induced acute graft dysfunction. The compositions and methods disclosed herein are also useful in treating or preventing inflammation and/or graft rejection associated with organ transplantation, in particular lung transplantation, including treatment, prevention or attenuation of progression of primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD) after organ transplantation, in particular lung transplantation.

The nucleic acid molecules disclosed herein individually, or in combination or in conjunction with other drugs, can be use for preventing or treating diseases, traits, conditions and/or disorders associated with TLR2 and/or TLR4, such as lung disorders or injury and graft rejection associated with organ transplantation, in particular lung transplantation.

The nucleic acid molecules disclosed herein are able to down-regulate the expression of TLR2 and/or TLR4 in a sequence specific manner. The nucleic acid molecules may include a sense strand and an antisense strand, which includes contiguous nucleotides that are at least partially complementary (antisense) to a TLR2 and/or TLR4 mRNA.

In some embodiments, dsRNA specific for TLR2 and/or TLR4 can be used in conjunction with other dsRNA.

Lung disorders and injury can be treated by RNA interference using nucleic acid molecules as disclosed herein. Exemplary lung disorders and injuries are disclosed herein. The nucleic acid molecules disclosed herein may inhibit the expression of TLR2 and/or TLR4 in a sequence specific manner.

Treatment of lung injury can be monitored by determining the level of PaO2 using suitable techniques known in the art. Treatment can also be monitored by determining total and differential bronchoalveolar lavage (BAL) counts of different cell populations (e.g. neutrophils, lymphocytes, monocytes, eosinophils, basophils) using suitable techniques known in the art. Treatment can also be monitored by determining the level of TLR2 and/or TLR4 mRNA or the level of TLR2 and/or TLR4 protein in the cells of the affected tissue. Treatment can also be monitored by non-invasive scanning of the affected organ or tissue such as by computer assisted tomography scan, magnetic resonance elastography scans and other suitable techniques known in the art.

A method for treating or preventing TLR2 associated disease or condition in a subject or organism may include contacting the subject or organism with a nucleic acid molecule as provided herein under conditions suitable to down-regulate the expression of TLR2 gene in the subject or organism. A method for treating or preventing TLR2 and TLR4 associated disease or condition in a subject or organism may include contacting the subject or organism with nucleic acid molecules as provided herein under conditions suitable to down-regulate the expression of TLR2 and TLR4 genes in the subject or organism.

A method for treating or preventing lung disease, disorder or injury in a subject or organism may include contacting the subject or organism with a nucleic acid molecule under conditions suitable to down-regulate the expression of TLR2 gene in the subject or organism.

A method for treating or preventing lung disease, disorder or injury in a subject or organism may include contacting the subject or organism with a nucleic acid molecule under conditions suitable to down-regulate the expression of TLR2 gene and with a nucleic acid molecule under conditions suitable to down-regulate the expression of both, TLR4 gene, in the subject or organism.

A method for treating or preventing one or more lung diseases or disorders selected from the group consisting of acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema, bronchiolitis obliterans after lung transplantation and graft rejection associated with organ transplantation, in particular lung transplantation, in a subject or organism may include contacting the subject or organism with a nucleic acid molecule under conditions suitable to down-regulate the expression of TLR2 gene in the subject or organism.

A method for treating or preventing one or more lung diseases or disorders selected from the group consisting of acute respiratory distress syndrome (ARDS), acute lung injury, pulmonary fibrosis (idiopathic), bleomycin induced pulmonary fibrosis, mechanical ventilation induced lung injury, chronic obstructive pulmonary disease (COPD), chronic bronchitis, emphysema, bronchiolitis obliterans after lung transplantation and graft rejection associated with organ transplantation, in particular lung transplantation, in a subject or organism may include contacting the subject or organism with a nucleic acid molecule under conditions suitable to down-regulate the expression of TLR2 and with a nucleic acid molecule under conditions suitable to down-regulate the expression of TLR4 gene, in the subject or organism.

In various embodiments the provided methods of treating a lung disease, disorder or injury comprise inhibiting the gene Toll-like receptor 2 (TLR2) in combination with one or more additional treatment methods selected from the group consisting of surgery, steroid therapy, non-steroid therapy, antiviral therapy, antifungal therapy, immunosuppressant therapy, anti-infective therapy, anti-hypertensive therapy and nutritional supplements. In various embodiments the provided methods of treating a lung disease, disorder or injury, comprise down-regulating the gene Toll-like receptor 2 (TLR2) in combination with immunosuppressant therapy.

In various embodiments the provided methods of treating a lung disease, disorder or injury comprise down-regulating the genes Toll-like receptor 2 (TLR2) and Toll-like receptor 4 (TLR4) in combination with one or more additional treatment methods selected from the group consisting of surgery, steroid therapy, non-steroid therapy, antiviral therapy, antifungal therapy, immunosuppressant therapy, anti-infective therapy, anti-hypertensive therapy and nutritional supplements. In various embodiments the provided methods of treating a lung disease, disorder or injury comprise down-regulating the Toll-like receptor 2 (TLR2) gene and down-regulating the Toll-like receptor 4 (TLR4) gene, in combination with immunosuppressant therapy.

Lung Disorders and Injury

The methods and compositions disclosed herein are useful in treating a subject experiencing or suffering from or at risk of suffering from acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema and medical complication of lung transplantation, including, without being limited to, primary graft failure, ischemia-reperfusion injury, reperfusion injury, reperfusion edema, allograft dysfunction, pulmonary reimplantation response, bronchiolitis obliterans after lung transplantation and/or primary graft dysfunction (PGD).

Acute Respiratory Distress Syndrome (ARDS)

ARDS is defined as an acute condition characterized by bilateral pulmonary infiltrates and severe hypoxemia in the absence of evidence for cardiogenic pulmonary edema. Acute respiratory distress syndrome (ARDS) is associated with diffuse alveolar damage (DAD) and lung capillary endothelial injury. The early phase is described as being exudative, whereas the later phase is fibroproliferative in character.

Early ARDS is characterized by an increase in the permeability of the alveolar-capillary barrier leading to an influx of fluid into the alveoli. The alveolar-capillary barrier is formed by the microvascular endothelium and the epithelial lining of the alveoli. Hence, a variety of insults resulting in damage either to the vascular endothelium or to the alveolar epithelium could result in ARDS. The main site of injury may be focused on either the vascular endothelium (e.g., sepsis) or the alveolar epithelium (e.g., aspiration of gastric contents).

Injury to the endothelium results in increased capillary permeability and the influx of protein-rich fluid into the alveolar space. Injury to the alveolar lining cells also promotes pulmonary edema formation. Two types of alveolar epithelial cells exist. Type I cells, comprising 90% of the alveolar epithelium, are injured easily. Damage to type I cells allows both increased entry of fluid into the alveoli and decreased clearance of fluid from the alveolar space. Type II cells have several important functions, including the production of surfactant, ion transport, and proliferation and differentiation into type I cells after cellular injury. Damage to type II cells results in decreased production of surfactant with resultant decreased compliance and alveolar collapse. Interference with the normal repair processes in the lung may lead to the development of fibrosis.

ARDS causes marked increase in intrapulmonary shunt, leading to severe hypoxemia. Although high inspired oxygen concentrations are required to maintain adequate tissue oxygenation and life, additional measures, like lung recruitment with positive end-expiratory pressure (PEEP), is often required. ARDS is uniformly associated with pulmonary hypertension. Pulmonary artery vasoconstriction likely contributes to ventilation-perfusion mismatch and is one of the mechanisms of hypoxemia in ARDS. Normalization of pulmonary artery pressures occurs as the syndrome resolves. Morbidity is considerable. Patients with ARDS are likely to have prolonged hospital courses, and they frequently develop nosocomial infections, especially ventilator-associated pneumonia. In addition, patients often have significant weight loss and muscle weakness and functional impairment may persist for months following hospital discharge. Most of the deaths in ARDS are attributable to sepsis or multiorgan failure rather than a primary pulmonary cause, although the recent success of mechanical ventilation using smaller tidal volumes may suggest a role of lung injury as a direct cause of death.

Acute Lung Injury (ALI)

Acute lung injury (ALI) is a diffuse heterogeneous lung injury characterized by hypoxemia, non cardiogenic pulmonary edema, low lung compliance and widespread capillary leakage. ALI is caused by any stimulus of local or systemic inflammation, principally sepsis.

There are two forms of ALI. Primary ALI is caused by a direct injury to the lung (e.g., pneumonia). Secondary ALI is caused by an indirect insult (e.g., pancreatitis). There are two stages—the acute phase characterized by disruption of the alveolar-capillary interface, leakage of protein rich fluid into the interstitium and alveolar space, and extensive release of cytokines and migration of neutrophils. A later reparative phase is characterized by fibroproliferation and remodeling of lung tissue.

The core pathology is disruption of the capillary-endothelial interface: this actually refers to two separate barriers—the endothelium and the basement membrane of the alveolus. In the acute phase of ALI, there is increased permeability of this barrier, and protein rich fluid leaks out of the capillaries. There are two types of alveolar epithelial cells Type 1 pneumocytes represent 90% of the cell surface area, and are easily damaged. Type 2 pneumocytes are more resistant to damage, which is important as these cells produce surfactant, transport ions and proliferate and differentiate into Type 1 cells.

The damage to the endothelium and the alveolar epithelium results in the creation of an open interface between the lung and the blood, facilitating the spread of micro-organisms from the lung systemically, stoking up a systemic inflammatory response. Moreover, the injury to epithelial cells handicaps the lung's ability to pump fluid out of airspaces. Fluid filled airspaces, loss of surfactant, microvascular thrombosis and disorganized repair (which leads to fibrosis) reduces resting lung volumes (decreased compliance), increasing ventilation-perfusion mismatch, right to left shunt and the work of breathing. In addition, lymphatic drainage of lung units appears to be curtailed—stunned by the acute injury: this contributes to the build up of extravascular fluid.

The patient has low lung volumes, atelectasis, loss of compliance, ventilation-perfusion mismatch (increased deadspace), and right to left shunt. Clinical features are—severe dyspnea, tachypnea, and resistant hypoxemia.

Prolonged inflammation and destruction of pneumocytes leads to fibroblastic proliferation, hyaline membrane formation and lung fibrosis. This fibrosing alveolitis may become apparent as early as five days after the initial injury. Subsequent recovery may be characterized by reduced physiologic reserve, and increased susceptibility to further lung injuries. Extensive microvascular thrombosis may lead to pulmonary hypertension, myocardial dysfunction and systemic hypotension.

Pulmonary Fibrosis (Idiopathic)

Idiopathic pulmonary fibrosis (IPF) is an idiopathic interstitial pneumonia that is characterized histopathologically by the presence of usual interstitial pneumonia. The hallmark pathologic feature of usual interstitial pneumonia is a heterogeneous, variegated appearance with alternating areas of healthy lung, interstitial inflammation, fibrosis, and honeycomb change. Fibrosis predominates over inflammation. Idiopathic pulmonary fibrosis portends a poor prognosis, and, to date, no proven effective therapies are available for the treatment of idiopathic pulmonary fibrosis beyond lung transplantation.

The etiology of idiopathic pulmonary fibrosis remains undefined; however, in the current hypothesis regarding the pathogenesis of idiopathic pulmonary fibrosis (IPF), exposure to an inciting agent (eg, smoke, environmental pollutants, environmental dust, viral infections, gastroesophageal reflux disease, chronic aspiration) in a susceptible host may lead to the initial alveolar epithelial damage. This damage may lead to activation of the alveolar epithelial cells, which provokes the migration, proliferation, and activation of mesenchymal cells with the formation of fibroblastic/myofibroblastic foci, leading to the exaggerated accumulation of extracellular matrix with the irreversible destruction of the lung parenchyma.

Other potential causes of idiopathic pulmonary fibrosis have been recognized through the study of familial pulmonary fibrosis. Familial pulmonary fibrosis may represent 20% of all cases of idiopathic pulmonary fibrosis. Genetic mutations in serum surfactant protein C have been discovered in some individuals with familial pulmonary fibrosis. It is believed these mutations in serum surfactant protein C may damage type II alveolar epithelial cells. Additionally, it has been described that mutant telomerase is associated with familial idiopathic pulmonary fibrosis.

Bleomycin Induced Pulmonary Fibrosis

Bleomycin is a glycopeptide antibiotic that was isolated from a strain of bacterium *Streptomyces verticillus*. Bleomycin refers to a family of structurally related compounds. When used as an anticancer agent, the chemotherapeutical forms are primarily bleomycin A2 and B2. It works by causing breaks in DNA. The drug is used in the treatment of variety of malignancies, including squamous cell carcinoma of the head and neck, cervix, and esophagus; germ cell tumors; testicular cancer; and both Hodgkin and non-Hodgkin lymphoma. Other anti-cancer drugs (such as for example cyclophosphamide and methotrexate) may cause lung fibrosis similarly to bleomycin.

A serious complication of bleomycin therapy is pulmonary fibrosis/interstitial pulmonary fibrosis (also called fibrosing alveolitis) and impaired lung function. Other, less common forms of lung injury include organizing pneumonia and hypersensitivity pneumonitis.

Chronic Obstructive Pulmonary Disease (COPD)

Chronic obstructive pulmonary disease (COPD), also known as chronic obstructive lung disease (COLD), chronic obstructive airway disease (COAD), chronic airflow limitation (CAL) and chronic obstructive respiratory disease (CORD), refers to chronic bronchitis and emphysema, a pair of commonly co-existing diseases of the lungs in which the airways become narrowed. This leads to a limitation of the flow of air to and from the lungs causing shortness of breath. In clinical practice, COPD is defined by its characteristically low airflow on lung function tests. In contrast to asthma, this limitation is poorly reversible and usually gets progressively worse over time.

COPD is caused by noxious particles or gas, most commonly from tobacco smoking, which triggers an abnormal inflammatory response in the lung. The inflammatory response in the larger airways is known as chronic bronchitis, which is diagnosed clinically when people regularly cough up sputum. In the alveoli, the inflammatory response causes destruction of the tissues of the lung, a process known as emphysema. The natural course of COPD is characterized by occasional sudden worsenings of symptoms called acute exacerbations, most of which are caused by infections or air pollution.

Both emphysematous destruction and small airway inflammation often are found in combination in individual patients, leading to the spectrum that is known as COPD. When emphysema is moderate or severe, loss of elastic recoil, rather than bronchiolar disease, is the mechanism of airflow limitation. By contrast, when emphysema is mild, bronchiolar abnormalities are most responsible for the deficit in lung function. Although airflow obstruction in emphysema is often irreversible, bronchoconstriction due to inflammation accounts for a limited amount of reversibility.

Pathological changes in chronic obstructive pulmonary disease (COPD) occur in the large (central) airways, the small (peripheral) bronchioles, and the lung parenchyma. The pathogenic mechanisms are not clear but most likely involve diverse mechanisms. The increased number of activated polymorphonuclear leukocytes and macrophages release elastases in a manner that cannot be counteracted effectively by antiproteases, resulting in lung destruction. The primary offender has been human leukocyte elastase, with a possible synergistic role suggested for proteinase 3 and macrophage-derived matrix proteinases, cysteine proteinases, and a plasminogen activator. Additionally, increased oxidative stress caused by free radicals in cigarette smoke, the oxidants released by phagocytes, and polymorphonuclear leukocytes all may lead to apoptosis or necrosis of exposed cells. Accelerated aging and autoimmune mechanisms have also been proposed as having roles in the pathogenesis of COPD.

Chronic Bronchitis

Chronic bronchitis is a chronic inflammation of the bronchi (medium-size airways) in the lungs. It is generally considered one of the two forms of chronic obstructive pulmonary disease (COPD). It is defined clinically as a persistent cough that produces sputum and mucus, for at least three months in two consecutive years. Mucous gland enlargement is the histologic hallmark of chronic bronchitis. The structural changes described in the airways include atrophy, focal squamous metaplasia, ciliary abnormalities, variable amounts of airway smooth muscle hyperplasia, inflammation, and bronchial wall thickening Neutrophilia develops in the airway lumen, and neutrophilic infiltrates accumulate in the submucosa. The respiratory bronchioles display a mononuclear inflammatory process, lumen occlusion by mucous plugging, goblet cell metaplasia, smooth muscle hyperplasia, and distortion due to fibrosis. These changes, combined with loss of supporting alveolar attachments, cause airflow limitation by allowing airway walls to deform and narrow the airway lumen.

Emphysema

Emphysema is a long-term, progressive disease of the lungs that primarily causes shortness of breath. In people with emphysema, the tissues necessary to support the physical shape and function of the lungs are destroyed. It is included in a group of COPD. Emphysema is called an obstructive lung disease because the destruction of lung tissue around smaller sacs, called alveoli, makes these air sacs unable to hold their functional shape upon exhalation. It is often caused by smoking or long-term exposure to air pollution.

Emphysema has 3 morphologic patterns. The first type, centriacinar emphysema, is characterized by focal destruction limited to the respiratory bronchioles and the central portions of acinus. This form of emphysema is associated with cigarette smoking and is most severe in the upper lobes. The second type, panacinar emphysema, involves the entire alveolus distal to the terminal bronchiole. The panacinar type is most severe in the lower lung zones and generally develops in patients with homozygous alpha1-antitrypsin (AAT) deficiency. The third type, distal acinar emphysema or paraseptal emphysema, is the least common form and involves distal airway structures, alveolar ducts, and sacs. This form of emphysema is localized to fibrous septa or to the pleura and leads to formation of bullae. The apical bullae may cause pneumothorax. Paraseptal emphysema is not associated with airflow obstruction.

Lung Transplantation and its Complications

The term "lung transplantation" is meant to encompass a surgical procedure in which a patient's diseased lungs are partially or totally replaced by lungs which come from a donor. Although a xenotransplant can be contemplated in certain situations, an allotransplant is usually preferable.

Lung transplantation has become a treatment of choice for patients with advanced/end-stage lung diseases. Indications for lung transplantation include chronic obstructive pulmonary disease (COPD), pulmonary hypertension, cystic fibrosis, idiopathic pulmonary fibrosis, and Eisenmenger syndrome. Typically, four different surgical techniques are used: single-lung transplantation, bilateral sequential transplantation, combined heart-lung transplantation, and lobar transplantation, with the majority of organs obtained from deceased donors. Within last decades, donor management, organ preservation, immunosuppressive regimens and control of infectious complications have been substantially improved and the operative techniques of transplantation procedures have been developed. Nonetheless, primary graft dysfunction (PGD) affects an estimated 10 to 25% of lung transplants and is the leading cause of early post-transplantation morbidity and mortality for lung recipients (Lee J C and Christie J D. 2009. Proc Am Thorac Soc, vol. 6: 39-46). PGD manifests as an acute lung injury defined by diffuse infiltrates on chest x-ray and abnormal oxygenation. There, there is some evidence to suggest a relationship between reperfusion injury, acute rejection, and the subsequent development of chronic graft dysfunction. Chronic rejection, known as obliterative bronchiolitis/bronchiolitis obliterans syndrome (BOS), is the key reason why the five year survival is only 50%, which is significantly worse than most other solid organ transplants. Investigators have recently demonstrated that PGD increases the risk of the development of BOS independent of other risk factors, and the severity of PGD is directly associated with increased risk for BOS (Daud S A, Yusen R D et al. 2007 Am J Respir Crit Care Med. 2007; 175(5):507-513).

Bronchiolitis Obliterans after Lung Transplantation

Bronchiolitis obliterans, and its clinical correlate bronchiolitis obliterans syndrome, affect up to 50-60% of patients who survive 5 years after transplantation. In most patients, bronchiolitis obliterans is a progressive process that responds poorly to augmented immunosuppression, and it accounts for more than 30% of all deaths occurring after the third postoperative year. Survival at 5 years after the onset of bronchiolitis obliterans is only 30-40%, and survival at 5 years after transplantation is 20-40% lower in patients with than in patients without bronchiolitis obliterans.

The diagnosis of bronchiolitis obliterans is based on histology, but histologic proof is often difficult to obtain using transbronchial lung biopsies. Therefore, in 1993, a committee sponsored by the International Society for Heart and Lung Transplantation (ISHLT) proposed a clinical description of bronchiolitis obliterans, termed BOS, which is based on changes in $FEV_1$. For each patient, a stable post-transplant baseline $FEV_1$ is defined as BOS stage 0; in patients who experience a decrease in $FEV_1$, progressive stages of BOS, from 1 to 3, are defined according to the magnitude of the decrease. Although this classification system has been adopted by transplant centers worldwide as a useful descriptor of chronic allograft dysfunction, concern has been raised regarding its ability to detect small changes in pulmonary function. This concern recently led to formulation of a revised classification system for BOS, which includes a new "potential-BOS" stage (BOS 0-p) defined as a decrease in midexpiratory flow rates ($FE_{25-75}$) and/or $FEV_1$. The rationale for including $FEF_{25-75}$ comes from studies in heart-lung and bilateral lung recipients, which showed that this variable deteriorates before $FEV_1$ at the onset of BOS. The new BOS 0-p stage is meant to alert the physician and to indicate the need for close functional monitoring and for in-depth assessment using surrogate markers for BOS. However, the usefulness of stage BOS 0-p in recipients of single lungs, in particular those with emphysema, still needs to be established.

The histopathological features of bronchiolitis obliterans suggest that injury and inflammation of epithelial cells and subepithelial structures of small airways lead to excessive fibroproliferation due to ineffective epithelial regeneration and aberrant tissue repair. In parallel with the concept of "injury response" that has been proposed to explain chronic dysfunction of other organ allografts, airway injury may occur via alloimmune-dependent and -independent mechanisms acting alone or in combination. The evolving concept is that bronchiolitis obliterans represents a "final common pathway" lesion, in which various insults can lead to a similar histological and clinical result. Yet the rarity of this syndrome in untransplanted individuals suggests that alloimmune-dependent mechanisms usually play a pivotal role.

Delivery of Nucleic Acid Molecules and Pharmaceutical Formulations

Nucleic acid molecules may be adapted for use to prevent or treat lung diseases, injuries, traits, conditions and/or disorders, alone or in combination with other therapies. A nucleic acid molecule may include a delivery vehicle, including liposomes, for administration to a subject, carriers and diluents and their salts, and/or can be present in pharmaceutically acceptable formulations.

Nucleic acid molecules disclosed herein may be delivered or administered as the compound per se (i.e. naked nucleic acid molecule) or as pharmaceutically acceptable salt and may be delivered or administered alone or as an active ingredient in combination with one or more pharmaceutically acceptable carrier, solvent, diluent, excipient, adjuvant and/or vehicle. In some embodiments, nucleic acid molecules disclosed herein are delivered to the target tissue by direct application of the naked molecules prepared with a carrier or a diluent.

The term "naked nucleic acid molecule" refers to nucleic acid molecules that are free from any delivery vehicle that acts to assist, promote or facilitate entry into the cell, including e.g. viral vectors, viral sequences, viral particles, liposome formulations, lipofectin or precipitating agents and the like. For example, siRNA in PBS is "naked siRNA".

Nucleic acid molecules may be delivered or administered to a subject by direct application of the nucleic acid molecules with a carrier or diluent or any other delivery vehicle that acts to assist, promote or facilitate entry into a cell, including e.g. viral vectors, viral sequences, viral particular, liposome formulations, lipofectin or precipitating agents and the like. Polypeptides that facilitate introduction of nucleic acid into a desired subject are described in US Application Publication No. 20070155658 (e.g., a melamine derivative such as 2,4,6-Triguanidino Traizine and 2,4,6-Tramidosarcocyl Melamine, a polyarginine polypeptide, and a polypeptide including alternating glutamine and asparagine residues).

Methods for the delivery of nucleic acid molecules are described in Akhtar et al., Trends Cell Bio., 2: 139 (1992); Delivery Strategies for Antisense Oligonucleotide Therapeutics, ed. Akhtar, (1995), Maurer et al., Mol. Membr. Biol., 16: 129-140 (1999); Hofland and Huang, Handb. Exp. Pharmacol., 137: 165-192 (1999); and Lee et al., ACS Symp. Ser., 752: 184-192 (2000); U.S. Pat. Nos. 6,395,713; 6,235,310; 5,225,182; 5,169,383; 5,167,616; 4,959217; 4,925,678; 4,487,603; and 4,486,194 and Sullivan et al., PCT WO 94/02595; PCT WO 00/03683 and PCT WO 02/08754; and U.S. Patent Application Publication No. 2003077829. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see e.g., Gonzalez et al., Bioconjugatc Chem., 10: 1068-1074 (1999); Wang et al., International PCT publication Nos. WO 03/47518 and WO 03/46185), poly(lactic-co-glycolic)acid (PLGA) and PLCA microspheres (see for example U.S. Pat. No. 6,447,796 and U.S. Application Publication No. 2002130430), biodegradable nanocapsules, and bioadhesive microspheres, or by proteinaceous vectors (O'Hare and Normand, International PCT Publication No. WO 00/53722). Alternatively, the nucleic acid composition/combination is locally delivered by direct injection, oral instillation, inhalation or by use of an infusion pump. Direct injection of the nucleic acid molecules as provided herein, whether e.g. intratracheal, subcutaneous, intramuscular, or intradermal, can take place using standard needle and syringe methodologies, or by needle-free technologies such as those described in Conry et al., Clin. Cancer Res., 5: 2330-2337 (1999) and Barry et al., International PCT Publication No. WO 99/31262. The molecules provided herein can be used as pharmaceutical agents. Pharmaceutical agents prevent, modulate the occurrence, or treat (alleviate a symptom to some extent, preferably all of the symptoms) of a disease state in a subject.

Nucleic acid molecules may be complexed with cationic lipids, packaged within liposomes, or otherwise delivered to target cells or tissues. The nucleic acid or nucleic acid complexes can be locally administered to relevant tissues ex vivo, or in vivo through direct dermal application, transdermal application, or injection, with or without their incorporation in biopolymers.

Delivery systems include surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. Chem. Rev. 1995, 95, 2601-2627; Ishiwata et al., Chem. Pharm. Bull. 1995, 43, 1005-1011).

Nucleic acid molecules may be formulated or complexed with polyethylenimine (e.g., linear or branched PEI) and/or polyethylenimine derivatives, including for example polyethyleneimine-polyethyleneglycol-N-acetylgalactosamine (PEI-PEG-GAL) or polyethyleneiminepolyethylene-glycol-tri-N-acetylgalactosamine (PEI-PEG-triGAL) derivatives, grafted PEIs such as galactose PEI, cholesterol PEI, antibody derivatized PEI, and polyethylene glycol PEI (PEG-PEI) derivatives thereof (see for example Ogris et al., 2001, AAPA PharmSci, 3, 1-11; Furgeson et al., 2003, Bioconjugate Chem., 14, 840-847; Kunath et al., 2002, Pharmaceutical Research, 19, 810-817; Choi et al., 2001, Bull. Korean Chem. Soc., 22, 46-52; Bettinger et al., 1999, Bioconjugate Chem., 10, 558-561; Peterson et al., 2002, Bioconjugate Chem., 13, 845-854; Erbacher et al., 1999, Journal of Gene Medicine Preprint, 1, 1-18; Godbey et al., 1999, PNAS USA, 96, 5177-5181; Godbey et al., 1999, Journal of Controlled Release, 60, 149-160; Diebold et al., 1999, Journal of Biological Chemistry, 274, 19087-19094; Thomas and Klibanov, 2002, PNAS USA, 99, 14640-14645; Sagara, U.S. Pat. No. 6,586,524 and United States Patent Application Publication No. 20030077829).

Nucleic acid molecules may be complexed with membrane disruptive agents such as those described in U.S. Patent Application Publication No. 20010007666. The membrane disruptive agent or agents and the nucleic acid molecule may also be complexed with a cationic lipid or helper lipid molecule, such as those lipids described in U.S. Pat. No. 6,235,310.

The nucleic acid molecules may be delivered or administered via a pulmonary delivery, such as by inhalation of an aerosol or spray dried formulation administered by an inhalation device or nebulizer, providing rapid local uptake of the nucleic acid molecules into relevant pulmonary tissues. Solid particulate compositions containing respirable dry particles of micronized nucleic acid compositions can be prepared by grinding dried or lyophilized nucleic acid compositions, and then passing the micronized composition through, for example, a 400 mesh screen to break up or separate out large agglomerates. A solid particulate composition comprising the nucleic acid compositions provided herein can optionally contain a dispersant which serves to facilitate the formation of an aerosol as well as other therapeutic compounds. A suitable dispersant is lactose, which can be blended with the nucleic acid compound in any suitable ratio, such as a 1 to 1 ratio by weight.

Aerosols of liquid particles may include a nucleic acid molecules disclosed herein and can be produced by any suitable means, such as with a nebulizer (see e.g., U.S. Pat. No. 4,501,729). Nebulizers are commercially available devices which transform solutions or suspensions of an active ingredient into a therapeutic aerosol mist either by means of acceleration of a compressed gas, typically air or oxygen, through a narrow venturi orifice or by means of ultrasonic agitation. Suitable formulations for use in nebulizers include the active ingredient(s) in a liquid carrier in an amount of up to 40% w/w preferably less than 20% w/w of the formulation. The carrier is typically water or a dilute aqueous alcoholic solution, preferably made isotonic with body fluids by the addition of, e.g., sodium chloride or other suitable salts. Optional additives include preservatives if the formulation is not prepared sterile, e.g., methyl hydroxybenzoate, anti-oxidants, flavorings, volatile oils, buffering agents and emulsifiers and other formulation surfactants. The aerosols of solid particles including the active composition and surfactant can likewise be produced with any solid particulate aerosol generator. Aerosol generators for administering solid particulate therapeutics to a subject produce particles, which are respirable, as explained above, and generate a volume of aerosol containing a predetermined metered dose of a therapeutic composition at a rate suitable for human administration. One illustrative type of solid particulate aerosol generator is an insufflator. Suitable formulations for administration by insufflation include finely comminuted powders, which can be delivered by means of an insufflator. In the insufflator, the powder, e.g., a metered dose thereof effective to carry out the treatments described herein, is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient(s), a suitable powder diluent, such as lactose, and an optional surfactant. The active ingredient(s) typically includes from 0.1 to 100 w/w of the formulation. A second type of illustrative aerosol generator includes a metered dose inhaler. Metered dose inhalers are pressurized aerosol dispensers, typically containing a suspension or solution formulation of the active ingredient in a liquefied propellant. During use these devices discharge the formulation through a valve adapted to deliver a metered volume to produce a fine particle spray containing the active ingredient(s). Suitable propellants include certain chlorofluorocarbon compounds, e.g., dichlorodifluoromethane, trichlorofluoromethane, dichlorotetrafluoroethane and mixtures thereof. The formulation can additionally contain one or more co-solvents, for example, ethanol, emulsifiers and other formulation surfactants, such as oleic acid or sorbitan trioleate, anti-oxidants and suitable flavoring agents. Other methods for pulmonary delivery are described in, e.g., US Patent Application Publication No. 20040037780, and U.S. Pat. Nos. 6,592,904; 6,582,728; 6,565,885.

Delivery systems may include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone). In one embodiment, the pharmaceutically acceptable carrier is a liposome or a transdermal enhancer. Examples of liposomes which can be used in accordance with the compositions and methods provided herein include the following: (1) CellFectin, 1:1.5 (M/M) liposome formulation of the cationic lipid N,NI,NII,NIII-tetramethyl-N,NI,NII,NIII-tetrapalmit-y-spermine and dioleoyl phosphatidyl-ethanolamine (DOPE) (GIBCO BRL); (2) Cytofectin GSV, 2:1 (M/M) liposome formulation of a cationic lipid and DOPE (Glen Research); (3) DOTAP (N-[1-(2,3-dioleoyloxy)-N,N,N-tri-methyl-ammoniumm-ethylsulfate) (Boehringer Manheim); and (4) Lipofectamine, 3:1 (M/M) liposome formulation of the polycationic lipid DOSPA, the neutral lipid DOPE (GIBCO BRL) and Di-Alkylated Amino Acid (DiLA2).

Nucleic acid molecules may include a bioconjugate, for example a nucleic acid conjugate as described in Vargeese et al., U.S. Ser. No. 10/427,160; U.S. Pat. No. 6,528,631; U.S. Pat. No. 6,335,434; U.S. Pat. No. 6,235,886; U.S. Pat. No. 6,153,737; U.S. Pat. No. 5,214,136; U.S. Pat. No. 5,138,045.

Expression of Nucleic Acid Molecules

Compositions, methods and kits disclosed herein may include an expression vector that includes a nucleic acid sequence encoding at least one nucleic acid molecule of such as provided herein in a manner that allows expression of the nucleic acid molecule. Methods of introducing nucleic acid molecules or one or more vectors capable of expressing the strands of dsRNA into the environment of the cell will depend on the type of cell and the make up of its environment. The nucleic acid molecule or the vector construct may be directly introduced into the cell (i.e., intracellularly); or introduced extracellularly into a cavity, interstitial space, into the circulation of an organism, introduced orally, or may be introduced by bathing an organism or a cell in a solution containing dsRNA. The cell is preferably a mammalian cell; more preferably a human cell. The nucleic acid molecule of the expression vector can include a sense region and an antisense region. The antisense region can include a sequence complementary to a RNA or DNA sequence encoding a gene selected from a TLR2 gene and a TLR4 gene; and the sense region can include a sequence complementary to the antisense region. The nucleic acid molecule can include two distinct strands having complementary sense and antisense regions. The nucleic acid molecule can include a single strand having complementary sense and antisense regions.

Nucleic acid molecules that interact with target RNA molecules and down-regulate gene encoding target RNA molecules (e.g., target RNA molecules referred to by Genbank Accession numbers herein) may be expressed from transcription units inserted into DNA or RNA vectors. Recombinant vectors can be DNA plasmids or viral vectors. Nucleic acid molecule expressing viral vectors can be constructed based on, but not limited to, adeno-associated virus, retrovirus, adenovirus, or alphavirus. The recombinant vectors capable of expressing the nucleic acid molecules can be delivered as described herein, and persist in target cells. Alternatively, viral vectors can be used that provide for transient expression of nucleic acid molecules. Such vectors can be repeatedly administered as necessary. Once expressed, the nucleic acid molecules bind and down-regulate gene function or expression via RNA interference (RNAi). Delivery of nucleic acid molecule expressing vectors can be systemic, such as by intravenous or intramuscular administration, by direct administration to the lung, e.g. by intratracheal injection, by administration to target cells ex-planted from a subject followed by reintroduction into the subject, or by any other means that would allow for introduction into the desired target cell.

Expression vectors may include a nucleic acid sequence encoding at least one nucleic acid molecule disclosed herein, in a manner which allows expression of the nucleic acid molecule. For example, the expression vector may encode one or both strands of a nucleic acid duplex, or a single self-complementary strand that self hybridizes into a nucleic acid duplex. The nucleic acid sequences encoding nucleic acid molecules can be operably linked in a manner that allows expression of the nucleic acid molecule. Non-limiting examples of such expression vectors are described in Paul et al., 2002, Nature Biotechnology, 19, 505; Miyagishi and Taira, 2002, Nature Biotechnology, 19, 497; Lee et al., 2002, Nature Biotechnology, 19, 500; and Novina et al., 2002, Nature Medicine, advance online publication doi: 10.1038/nm725. Expression vectors may also be included in a mammalian (e.g., human) cell.

An expression vector may include a nucleic acid sequence encoding two or more nucleic acid molecules, which can be the same or different. Expression vectors may include a sequence for a nucleic acid molecule complementary to a nucleic acid molecule referred to by a Genbank Accession number NM_003264.3 (TLR2), NR_024169.1 (TLR4), NM_138554.3 (TLR4) or NR_024168.1 (TLR4).

An expression vector may include one or more of the following: a) a transcription initiation region (e.g., eukaryotic pol I, II or III initiation region); b) a transcription termination region (e.g., eukaryotic pol I, II or III termination region); c) an intron and d) a nucleic acid sequence encoding at least one of the nucleic acid molecules, wherein said sequence is operably linked to the initiation region and the termination region in a manner that allows expression and/or delivery of the nucleic acid molecule. The vector can optionally include an open reading frame (ORF) for a protein operably linked on the 5'-side or the 3'-side of the sequence encoding the nucleic acid molecule; and/or an intron (intervening sequences).

Transcription of the nucleic acid molecule sequences can be driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, PNAS USA, 87, 6743-7; Gao and Huang 1993, Nucleic Acids Res., 21, 2867-72; Lieber et al., 1993, Methods Enzymol., 217, 47-66; Zhou et al., 1990, Mol. Cell. Biol., 10, 4529-37). Several investigators have demonstrated that nucleic acid molecules expressed from such promoters can function in mammalian cells (e.g. Kashani-Sabot et al., 1992, Antisense Res. Dev., 2, 3-15; Ojwang et al., 1992, PNAS USA, 89, 10802-6; Chen et al., 1992, Nucleic Acids Res., 20, 4581-9; Yu et al., 1993, PNAS USA, 90, 6340-4; L'Huillier et al., 1992, EMBO J., 11, 4411-8; Lisziewicz et al., 1993, PNAS USA, 90, 8000-4; Thompson et al., 1995, Nucleic Acids Res., 23, 2259; Sullenger & Cech, 1993, Science, 262, 1566). More specifically, transcription units such as the ones derived from genes encoding U6 small nuclear RNA (snRNA), transfer RNA (tRNA) and adenovirus VA RNA are useful in generating high concentrations of desired RNA molecules such as siNA in cells (Thompson et al., supra; Couture and Stinchcomb, 1996, supra; Noonberg et al., 1994, Nucleic Acid Res., 22, 2830; Noonberg et al., U.S. Pat. No. 5,624,803; Good et al., 1997, Gene Ther., 4, 45; Beigelman et al., International PCT Publication No. WO 96/18736). The above nucleic acid transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (see Couture and Stinchcomb, 1996 supra).

A nucleic acid molecule may be expressed within cells from eukaryotic promoters (e.g., Izant and Weintraub, 1985, Science, 229, 345; McGarry and Lindquist, 1986, PNAS USA 83, 399; Scanlon et al., 1991, PNAS USA, 88, 10591-5; Kashani-Sabet et al., 1992, Antisense Res. Dev., 2, 3-15; Dropulic et al., 1992, J. Virol., 66, 1432-41; Weerasinghe et al., 1991, J. Virol., 65, 5531-4; Ojwang et al., 1992, PNAS USA, 89, 10802-6; Chen et al., 1992, Nucleic Acids Res., 20, 4581-9; Sarver et al., 1990 Science, 247, 1222-1225; Thompson et al., 1995, Nucleic Acids Res., 23, 2259; Good et al., 1997, Gene Therapy, 4, 45). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, Nucleic Acids Symp. Ser., 27, 15-6; Taira et al., 1991, Nucleic Acids Res., 19, 5125-30; Ventura et al., 1993, Nucleic Acids Res., 21, 3249-55; Chowrira et al., 1994, J. Biol. Chem., 269, 25856).

A viral construct packaged into a viral particle would accomplish both efficient introduction of an expression construct into the cell and transcription of dsRNA construct encoded by the expression construct.

Methods for oral introduction include direct mixing of RNA with food of the organism, as well as engineered approaches in which a species that is used as food is engineered to express an RNA, then fed to the organism to be affected. Physical methods may be employed to introduce a nucleic acid molecule solution into the cell. Physical methods of introducing nucleic acids include injection of a solution containing the nucleic acid molecule, bombardment by particles covered by the nucleic acid molecule, soaking the cell or organism in a solution of the RNA, or electroporation of cell membranes in the presence of the nucleic acid molecule.

Other methods known in the art for introducing nucleic acids to cells may be used, such as lipid-mediated carrier transport, chemical mediated transport, such as calcium phosphate, and the like. Thus the nucleic acid molecules may be introduced along with components that perform one or more of the following activities: enhance RNA uptake by the cell, promote annealing of the duplex strands, stabilize the annealed strands, or otherwise increase inhibition of the target gene.

Nucleic Acid Formulations

The nucleic acid molecules or the vector construct can be introduced into the cell using suitable formulations, e.g. a lipid formulation such as in Lipofectamine™ 2000 (Invitrogen, CA, USA), vitamin A coupled liposomes (Sato et al. Nat Biotechnol 2008; 26:431-442, PCT Patent Publication No. WO 2006/068232). Lipid formulations can also be administered to animals such as by intravenous, intramuscular, or intraperitoneal injection, or intratracheal injection, or orally or by inhalation or other methods as are known in the art. When the formulation is suitable for administration into animals such as mammals and more specifically humans, the formulation is also pharmaceutically acceptable. Pharmaceutically acceptable formulations for administering oligonucleotides are known and can be used. In some instances, it may be preferable to formulate nucleic acid molecules, e.g. dsRNA, in a buffer or saline solution and directly inject the formulated dsRNA into the target organ or into target cells, as in studies with oocytes. The direct injection of dsRNA duplexes may also be done. For suitable methods of introducing dsRNA see for example U.S. published patent application No. 2004/0203145, 20070265220, which are incorporated herein by reference.

Pharmaceutically acceptable formulations for treating lung disorders or injury are known and can be used for administration of the therapeutic combinations disclosed herein. In some instances, the therapeutic compositions disclosed herein may be formulated for intravenous administration for systemic delivery, or as aerosols, for example for intranasal administration, or as nasal drops, for example for intranasal instillation, or as suitable for intratracheal instillation.

Polymeric nanocapsules or microcapsules facilitate transport and release of the encapsulated or bound nucleic acid molecule, e.g. dsRNA, into the cell. They include polymeric and monomeric materials, e.g. especially including polybutylcyanoacrylate. A summary of materials and fabrication methods has been published (see Kreuter, 1991). The polymeric materials which are formed from monomeric and/or oligomeric precursors in the polymerization/nanoparticle generation step, are per se known from the prior art, as are the molecular weights and molecular weight distribution of the polymeric material which a person skilled in the field of manufacturing nanoparticles may suitably select in accordance with the usual skill.

Nucleic acid molecules may be formulated as a microemulsion. A microemulsion is a system of water, oil and amphiphile which is a single optically isotropic and thermodynamically stable liquid solution. Typically microemulsions are prepared by first dispersing an oil in an aqueous surfactant solution and then adding a sufficient amount of a 4th component, generally an intermediate chain-length alcohol to form a transparent system.

Surfactants that may be used in the preparation of microemulsions include, but are not limited to, ionic surfactants, non-ionic surfactants, Brij 96, polyoxyethylene olcyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DA0750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules.

Water Soluble Crosslinked Polymers

Delivery formulations can include water soluble degradable crosslinked polymers that include one or more degradable crosslinking lipid moiety, one or more PEI moiety, and/or one or more mPEG (methyl ether derivative of PEG (methoxypoly (ethylene glycol)).

The degradable crosslinking lipid moiety may be reacted with a polyethyleneimine (PEI) as shown in Scheme A below:

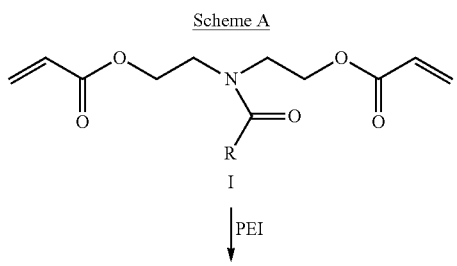

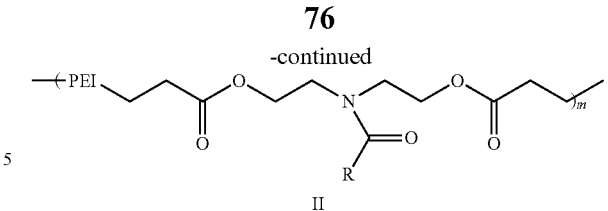

The reaction illustrated in Scheme A may be carried out by intermixing the PEI and the diacrylate (I) in a mutual solvent such as ethanol, methanol or dichloromethane with stirring, preferably at room temperature for several hours, then evaporating the solvent to recover the resulting polymer. While not wishing to be bound to any particular theory, it is believed that the reaction between the PEI and diacrylate (I) involves a Michael reaction between one or more amines of the PET with double bond(s) of the diacrylate (see J. March, Advanced Organic Chemistry 3rd Ed., pp. 711-712 (1985)). The diacrylate shown in Scheme A may be prepared in the manner as described in U.S. application Ser. No. 11/216,986 (US Publication No. 2006/0258751).

The molecular weight of the PEI is preferably in the range of about 200 to 25,000 Daltons more preferably 400 to 5,000 Daltons, yet more preferably 600 to 2,000 Daltons. PEI may be either branched or linear.

The molar ratio of PEI to diacrylate is preferably in the range of about 1:2 to about 1:20. The weight average molecular weight of the cationic lipopolymer may be in the range of about 500 Daltons to about 1,000,000 Daltons preferably in the range of about 2,000 Daltons to about 200,000 Daltons. Molecular weights may be determined by size exclusion chromatography using PEG standards or by agarose gel electrophoresis.

The cationic lipopolymer is preferably degradable, more preferably biodegradable, e.g., degradable by a mechanism selected from the group consisting of hydrolysis, enzyme cleavage, reduction, photo-cleavage, and sonication. While not wishing to be bound to any particular theory, it is believed that degradation of the cationic lipopolymer of formula (II) within the cell proceeds by enzymatic cleavage and/or hydrolysis of the ester linkages.

Synthesis may be carried out by reacting the degradable lipid moiety with the PEI moiety as described above. Then the mPEG (methyl ether derivative of PEG (methoxypoly (ethylene glycol)), is added to form the degradable crosslinked polymer. In preferred embodiments, the reaction is carried out at room temperature. The reaction products may be isolated by any means known in the art including chromatographic techniques. In a preferred embodiment, the reaction product may be removed by precipitation followed by centrifugation.

Dose and Dosage Units

The useful dosage to be administered and the particular mode of administration will vary depending upon such factors as the cell type, or for in vivo use, the age, weight and the particular recipient and region thereof to be treated, the particular nucleic acid and delivery method used, the therapeutic or diagnostic use contemplated, and the form of the formulation, for example, suspension, emulsion, micelle or liposome, as will be readily apparent to those skilled in the art. Typically, dosage is administered at lower levels and increased until the desired effect is achieved.

When lipids are used to deliver the nucleic acid, the amount of lipid compound that is administered can vary and generally depends upon the amount of nucleic acid being administered. For example, the weight ratio of lipid compound to nucleic acid is preferably from about 1:1 to about 30:1, with a weight ratio of about 5:1 to about 10:1 being more preferred.

A suitable dosage unit of nucleic acid molecules may be in the range of about 0.001 to 20-100 milligrams per kilogram body weight of the recipient per day, or in the range of 0.01 to 20 milligrams per kilogram body weight per day, or in the range of 0.01 to 10 milligrams per kilogram body weight per day, or in the range of 0.1 to 5 milligrams per kilogram body weight per day, or in the range of 0.1 to 2.5 milligrams per kilogram body weight per day, in a regimen of a single dose or a series of doses given at short (e.g. 1-5 minute) or long (e.g. several hours) intervals.

In certain embodiment a suitable dosage unit of nucleic acid molecules may be in the range of about 0.01 mg, 0.02 mg, 0.03 mg, 0.04 mg, 0.05 mg, 0.0.6 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, 10.1 mg, 10.2 mg, 10.3 mg, 10.4 mg, 10.5 mg, 10.6 mg, 10.7 mg, 10.8 mg, 10.9 mg, 11.0 mg, 11.1 mg, 11.2 mg, 11.3 mg, 11.4 mg, 11.5 mg, 11.6 mg, 11.7 mg, 11.8 mg, 11.9 mg, 12.0 mg, 12.1 mg, 12.2 mg, 12.3 mg, 12.4 mg, 12.5 mg, 12.6 mg, 12.7 mg, 12.8 mg, 12.9 mg, 13.0 mg, 13.1 mg, 13.2 mg, 13.3 mg, 13.4 mg, 13.5 mg, 13.6 mg, 13.7 mg, 13.8 mg, 13.9 mg, 14.0 mg, 14.1 mg, 14.2 mg, 14.3 mg, 14.4 mg, 14.5 mg, 14.6 mg, 14.7 mg, 14.8 mg, 14.9 mg, 15.0 mg, 15.1 mg, 15.2 mg, 15.3 mg, 15.4 mg, 15.5 mg, 15.6 mg, 15.7 mg, 15.8 mg, 15.9 mg, 16.0 mg, 16.1 mg, 16.2 mg, 16.3 mg, 16.4 mg, 16.5 mg, 16.6 mg, 16.7 mg, 16.8 mg, 16.9 mg, 17.0 mg, 17.1 mg, 17.2 mg, 17.3 mg, 17.4 mg, 17.5 mg, 17.6 mg, 17.7 mg, 17.8 mg, 17.9 mg, 18.0 mg, 18.1 mg, 18.2 mg, 18.3 mg, 18.4 mg, 18.5 mg, 18.6 mg, 18.7 mg, 18.8 mg, 18.9 mg, 19.0 mg, 19.1 mg, 19.2 mg, 19.3 mg, 19.4 mg, 19.5 mg, 19.6 mg, 19.7 mg, 19.8 mg, 19.9 mg, 20.0 mg per kilogram body weight of the recipient per day. in a regimen of a single dose or a series of doses given at short (e.g. 1-5 minute) or long (e.g. several hours) intervals.

Suitable amounts of nucleic acid molecules may be introduced and these amounts can be empirically determined using standard methods. Effective concentrations of individual nucleic acid molecule species in the environment of a cell may be about 1 femtomolar, about 50 femtomolar, 100 femtomolar, 1 picomolar, 1.5 picomolar, 2.5 picomolar, 5 picomolar, 10 picomolar, 25 picomolar, 50 picomolar, 100 picomolar, 500 picomolar, 1 nanomolar, 2.5 nanomolar, 5 nanomolar, 10 nanomolar, 25 nanomolar, 50 nanomolar, 100 nanomolar, 500 nanomolar, 1 micromolar, 2.5 micromolar, 5 micromolar, 10 micromolar, 100 micromolar or more.

Dosage of each therapeutic agent may be independently from about 0.01 μg to about 1 g per kg of body weight (e.g., 0.1 μg, 0.25 μg, 0.5 μg, 0.75 μg, 1 μg, 2.5 μg, 5 μg, 10 μg, 25 μg, 50 μg, 100 μg, 250 μg, 500 μg, 1 mg, 2.5 mg, 5 mg, 10 mg, 25 mg, 50 mg, 100 mg, 250 mg, or 500 mg, or 1 g, per kg of body weight).

In certain embodiments dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

In certain embodiments, the double-stranded RNA compound is present in the composition in a dose level of about 0.05 mg, 0.06 mg, 0.07 mg, 0.08 mg, 0.09 mg, 0.1 mg, 0.2 mg, 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, or 10.0 mg per dose form.

It is understood that the specific dose level for any particular subject depends upon a variety of factors including the activity of the specific compound employed, the age, body weight, general health, sex, diet, time of administration, frequency of treatment, route of administration, and rate of excretion, drug combination and the severity of the particular disease undergoing therapy.

Regimens for continuing therapy, including dose and frequency may be guided by the initial response and clinical judgment.

The pulmonary route of administration is preferred, such as by intratracheal instillation, inhalation of an aerosol formulation, although other routes, may be required in specific administration, as for example to the mucous membranes of the nose, throat, bronchial tissues or lungs. Transdermal route of administration may also be used, including active systems where delivery is driven by microneedles or energy applied via ultrasound or lasers.

The therapeutic compositions disclosed herein are preferably administered into the lung of a subject suffering from lung injury, disorder, disease or who has undergone lung transplantation, by inhalation of an aerosol containing the composition/combination, by intranasal or intratracheal instillation or by inhalation via ventilation machine (e.g. for administration to an unconscious patient). In some embodiments the oligouncleotide compositions disclosed herein are administered by inhalation into the lung of a subject who has undergone lung transplantation. For further information on pulmonary delivery of pharmaceutical compositions see Weiss et al., Human Gene Therapy 1999. 10:2287-2293; Densmore et al., Molecular therapy 1999. 1:180-188; Gautam et al., Molecular Therapy 2001. 3:551-556; and Shahiwala & Misra, AAPS PharmSciTech 2004. 24; 6(3):E482-6. Additionally, respiratory formulations for dsRNA are described in U.S. Patent Application Publication No. 2004/0063654. Respiratory formulations for dsRNA are described in US Patent Application Publication No. 2004/0063654. International Patent Publication No. WO 2008/132723 to one of the assignees of the present invention, and hereby incorporated by reference in its entirety discloses therapeutic delivery of dsRNA to the respiratory system.

The dosage of each therapeutic agent is determined independently.

Pharmaceutical compositions that include the nucleic acid molecules disclosed herein may be administered once daily (q.d.), twice a day (b.i.d.), three times a day (t.i.d.), four times a day (q.i.d.), or at any interval and for any duration that is medically appropriate. However, the therapeutic agent may also be dosed in dosage units containing two, three, four, five, six or more sub-doses administered at appropriate intervals throughout the day. In that case, the nucleic acid molecules contained in each sub-dose may be correspondingly smaller in order to achieve the total daily dosage unit. The dosage unit can also be compounded for a single dose over several days, e.g., using a drug delivery pump; or using a conventional sustained release formulation which provides sustained and consistent release of the dsRNAs over a several day period. Sustained release formulations are well known in the art. The dosage unit may contain a corresponding multiple of the daily dose. The composition can be compounded in such a way that the sum of the multiple units of a nucleic acids together contain a sufficient dose.

Pharmaceutical Compositions, Kits, and Containers

Provided are compositions, kits, containers and formulations that include at least one therapeutic agents (e.g., small organic molecule chemical compound; protein, antibody, peptide, peptidomimetic and nucleic acid molecule) which target, decrease, down-regulate or inhibit the expression/activity/function of the gene TLR2, for administering to a patient.

Also provided are compositions, kits, containers and formulations that include at least two therapeutic agents (e.g., small organic molecule; protein, antibody, peptide, peptidomimetic and nucleic acid molecule), at least one therapeutic agent which target, decrease, down-regulate or inhibit the expression/activity/function of the gene TLR2 and at least one therapeutic agent which target, decrease, down-regulate or inhibit the expression/activity/function of the gene TLR4, for administering to a patient.

A kit may include at least one container and at least one label. Suitable containers include, for example, bottles, vials, syringes, and test tubes. The containers can be formed from a variety of materials such as glass, metal or plastic. The container can hold amino acid(s), small molecule(s), nucleic acid(s), protein(s), peptides(s), peptidomimetic(s), cell population(s) and/or antibody(s). In one embodiment, the container holds a composition that is effective for treating, diagnosis, prognosing or prophylaxing a condition described herein and can have a sterile access port (for example the container can be an intravenous solution bag or a vial having a stopper pierceable by a hypodermic injection needle). The active agent in the composition can be a nucleic acid molecule(s) capable of specifically binding TLR2 and/or modulating the function of TLR2. The active agent in the composition can be a nucleic acid molecule(s) capable of specifically binding TLR4 and/or modulating the function of TLR4. The active agents in the composition can be a nucleic acid molecule(s) capable of specifically binding TLR2 and TLR4 and/or modulating the function of TLR2 and TLR4.

Kits may further include associated indications and/or directions; reagents and other compositions or tools used for such purpose as described herein.

A kit may further include a second container that includes a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

The units dosage ampules or multidose containers, in which the therapeutic agents are packaged prior to use, may include an hermetically sealed container enclosing an amount of therapeutic agent or solution containing a therapeutic agent suitable for a pharmaceutically effective dose thereof, or multiples of an effective dose. The therapeutic agent is packaged as a sterile formulation, and the hermetically sealed container is designed to preserve sterility of the formulation until use.

The container in which the therapeutic agent molecules are packaged may be labeled, and the label may bear a notice in the form prescribed by a governmental agency, for example the Food and Drug Administration, which notice is reflective of approval by the agency under Federal law, of the manufacture, use, or sale of the therapeutic material therein for human administration.

Federal law requires that the use of pharmaceutical compositions in the therapy of humans be approved by an agency of the Federal government. In the United States, enforcement is the responsibility of the Food and Drug Administration, which issues appropriate regulations for securing such approval, detailed in 21 U.S.C. §301-392. Regulation for biologic material, including products made from the tissues of animals is provided under 42 U.S.C. §262. Similar approval is required by most countries. Regulations vary from country to country, but individual procedures are well known to those in the art and the compositions and methods provided herein preferably comply accordingly.

As such, provided herein is a pharmaceutical product which may include a combination of nucleic acid molecules in solution in a pharmaceutically acceptable injectable carrier and suitable for administration to a patient, and a notice associated with the container in a form prescribed by a governmental agency regulating the manufacture, use, or sale of pharmaceuticals, which notice is reflective of approval by the agency of manufacture, use, or sale of the solution comprising the nucleic acids for human administration. Compositions, kits and methods disclosed herein may include packaging a nucleic acid molecule disclosed herein that includes a label or package insert. The label may include indications for use of the nucleic acid molecules such as use for treatment or prevention of lung disorders or injury in a human, including treatment of acute respiratory distress syndrome (ARDS), acute lung injury, pulmonary fibrosis (idiopathic), bleomycin induced pulmonary fibrosis, mechanical ventilator induced lung injury, chronic obstructive pulmonary disease (COPD), chronic bronchitis, emphysema, bronchiolitis obliterans after lung transplantation and lung transplantation-induced acute graft dysfunction, and any other disease or conditions that are related to or will respond to down-regulation of the expression of TLR2 in a cell or tissue, alone or in combination in combination with other therapies; or to down-regulation of the expression of TLR2 and TLR4, alone or in combination with other therapies. A label may include an indication for use in reducing expression of TLR2 gene. A label may include an indication for use in reducing expression of TLR2 gene and TLR4 gene. A "package insert" is used to refer to instructions customarily included in commercial packages of therapeutic products, that contain information about the indications, usage, dosage, administration, contraindications, other therapeutic products to be combined with the packaged product, and/or warnings concerning the use of such therapeutic products, etc.

Those skilled in the art will recognize that other lung disorder/injury treatments, drugs and therapies known in the art can be readily combined with the therapeutic combination disclosed herein and are hence contemplated herein.

The methods and compositions provided herein will now be described in greater detail by reference to the following non-limiting examples.

EXAMPLES

Example 1: Generation of Sequences for Active dsRNA Compounds to the TLR2 and TLR4 Genes and Production of the dsRNA Compounds Using proprietary algorithms and the known sequence of the genes disclosed herein, the antisense and corresponding sense sequences of dsRNA compounds were generated. In addition to the algorithm, 20-, 21-, 22-, and 23-mer oligomer sequences are generated by 5' and/or 3' extension of the 19-mer sequences. The sequences that have been generated using this method are fully complementary to a segment of corresponding mRNA sequence.

SEQ IDs Numbers 5-12,136 provide oligonucleotide sequences useful in the preparation of dsRNA compounds disclosed herein. Each sequence is presented in 5' to 3' orientation.

For each gene there is a separate list of 19-mer sense and corresponding antisense oligonucleotide sequences, which are prioritized based on their score in the proprietary algorithm as the best sequences for targeting the human gene expression.

The siRNA compounds disclosed herein are synthesized by any methods described herein, infra.

Example 2: Evaluation of Inhibitory Activity of dsRNA Compounds Targeting TLR2 and TLR4 Genes Inhibitory activity of dsRNA compounds is assessed in vitro by transfection of dsRNA compounds into human HeLa or human PC3 cells.

Preparation of Cells for dsRNA Transfection

HeLa cells (American Type Culture Collection) are cultured as described in Czaudema, et al. (NAR, 2003. 31:670-82).

In each well of a 6-well plate, 1×105 human HeLa cells (ATCC, Cat#CCL-2) are inoculated in 2 mL growth medium in order to reach 30-50% confluence one day later. Cells are then incubated in 37±1° C., 5% CO2 incubator for 24 hours. One day post inoculation, cell culture media is replaced with 1.5 mL fresh growth medium per well.

dsRNA Transfection

Following incubation, cells are transfected with dsRNA compounds using the Lipofectamine™ 2000 reagent (Invitrogen) at final concentrations ranging between 0.0035 nM to 100 nM (final dsRNA concentration in cell culture wells). Cells are then incubated in a 37±1° C., 5% CO2 incubator for 48 hours.

For the determination of transfection efficiency, cells are similarly transfected with a 20 nM solution of a Cy3-labeled dsRNA which targets the DDIT4 gene transcript.

As negative control, cells are similarly transfected with a scrambled sequence dsRNA (CNL_1) at final concentrations of 40 and 100 nM.

RNA Preparation for Real Time qPCR (qPCR)

At 48 h after transfection cells are harvested and RNA is extracted from cells isolated using EZ-RNA kit [Biological Industries (#20-410-100)].

Transfection efficiency is tested by fluorescent microscopy.

Determining Inhibitory Activity In Vitro

The percent of down-regulation of gene expression using specific dsRNA compounds disclosed herein is determined using qPCR analysis. The relative quantity of target gene mRNA is determined using as template RNA prepared from each of the dsRNA-transfected cell samples. dsRNA activity is determined based on the ratio of the target gene mRNA quantity in dsRNA-treated samples versus non-transfected control samples.

Chemically modified dsRNA compounds disclosed herein are tested in vitro as described and are shown to down-regulate target gene expression.

Example 3: Stability of dsRNA Compounds

Nuclease resistance of the dsRNA compounds disclosed herein is tested in human serum and/or in bronchoalveolar lavage fluid (BALF).

For stability testing, a dsRNA compound is diluted in human serum or in bronchoalveolar lavage fluid (BALF) to a required final concentration (e.g. 7 μM). A 5 μL aliquot is transferred to 15 μL of 1.5×TBE-loading buffer, immediately frozen in liquid nitrogen, and transferred to −20° C. This represents "Time Point 0". The remaining dsRNA solution is divided into 5 μL aliquots, which are incubated at 37° C. for 30 min, 1 h, 6 h, 8 h, 10 h, 16 h or 24 h.

Following incubation, dsRNA compound samples are transferred to 15 μL of 1.5×TBE-loading buffer. 5 μL of each dsRNA compound in loading buffer sample is loaded onto a non denaturing 20% polyacrylamide gel and electrophoresis is performed. The positive control, double-strand migration reference (a non-relevant, 19-base pairs, blunt-ended, double-stranded RNA with similar chemical modifications), and single-strand migration reference (a non-relevant ssRNA with chemical modifications), as well as the Time Point 0 sample are loaded on the same gel and electrophoresed in parallel.

For dsRNA visualization the gel is stained with Ethidium bromide solution (1.0 μg/μL).

Stability of dsRNA compounds disclosed herein is determined by examining the migration pattern of dsRNA samples on PAGE following incubation in human serum and/or in bronchoalveolar lavage fluid (BALF).

Example 4: Efficacy of dsRNA in Mouse Models of Orthotopic Vascularized Aerated Lung Transplantation Therapeutic efficacy of dsRNA compounds described herein in preventing primary graft dysfunction caused by both prolonged cold ischemia and immune rejection was tested in syngeneic and allogeneic mouse orthotopic models of lung transplantation. The method of orthotopic vascularized aerated left lung transplantation in the mouse utilizes cuff techniques for the anastomosis of pulmonary artery, pulmonary veins and bronchus. This method has been reported in several publications (Okazaki et al., Am J Transplant, 2007; 7:1672-9 and Krupnick et al. Nature Protocols, 2009; vol. 4 No. 1:86-93).

dsRNA Test Compounds

One dsRNA compound targeting TLR4 (designated TLR4_4_S500) and two dsRNA compounds targeting TLR2 (designated TLR2_7_S73 and TLR2_4_S73) were tested in syngeneic mouse orthotopic models of lung transplantation. One dsRNA compound targeting TLR4 (designated TLR4_4_S500) and one dsRNA compounds targeting TLR2 (designated TLR2_4_S73) were tested in allogeneic mouse orthotopic models of lung transplantation. A dsRNA compound directed at enhanced green fluorescent protein (EGFP) (designated EGFP_5_S763) and/or vehicle (phosphate buffer solution (PBS)) served as negative control in these experiments.

Table 1 lists dsRNA compounds that were tested in syngeneic and allogeneic mouse orthotopic models of lung transplantation.

TABLE 1

| DsRNA compound | Target gene |
| --- | --- |
| TLR4_4_S500 | TLR4, toll-like receptor 4 |
| TLR2_7_S73 | TLR2, toll-like receptor 2 |
| TLR2_4_S73 | TLR2, toll-like receptor 2 |
| EGFP_5_S763 | EGFP, Enhanced green fluorescent protein |

Table 2 provides the sense strand and the antisense strand sequences of the dsRNA compounds that were tested in syngeneic and allogeneic mouse orthotopic models of lung transplantation. Table 2 further provides the cross species data.

TABLE 2

| DsRNA compound | Sense 5'->3' | Antisense 5'->3' | cross species |
| --- | --- | --- | --- |
| TLR4_4_S500 | GAGUUCAGGUUAACAUAUA | UAUAUGUUAACCUGAACUC | rat, mouse |
| TLR2_7_S73 | GCAAACUGCGCAAGAUAAU | AUUAUCUUGCGCAGUUUGC | rat, mouse |
| TLR2_4_S73 | CCUCUUUGAAAUACUUAAA | UUUAAGUAUUUCAAAGAGG | rat, mouse |
| EGFP_5_S763 | GGCUACGUCCAGGAGCGCACC | GGUGCGCUCCUGGACGUAGCC | 21-mer |

Table 3 provides the sense strand and the antisense strand modification patterns of the dsRNA compounds that were tested in syngeneic and allogeneic mouse orthotopic models of lung transplantation.

TABLE 3

| DsRNA compound | Sense 5'->3' | Antisense 5'->3' |
| --- | --- | --- |
| TLR4_4_S500 | 2'-OMe sugar modified ribonucleotides in positions: 2, 4, 6, 8, 10, 12, 14, 16 and 18 | 2'-OMe sugar modified ribonucleotides in positions: 1, 3, 5, 7, 9, 11, 13, 15, 17 and 19 |
|  | unmodified ribonucleotides in positions: 1, 3, 5, 7, 9, 11, 13, 15, 17 and 19<br>3'-terminal phosphate | unmodified ribonucleotides in positions: 2, 4, 6, 8, 10, 12, 14, 16 and 18<br>3'-terminal phosphate |
| TLR2_7_S73 | 2'-OMe sugar modified ribonucleotides in positions: 2, 4, 6, 8, 10, 12, 14, 16 and 18 | 2'-OMe sugar modified ribonucleotides in positions: 1, 3, 5, 7, 9, 11, 13, 15, 17 and 19 |
|  | unmodified ribonucleotides in positions: 1, 3, 5, 7, 9, 11, 13, 15, 17 and 19<br>No 3'-terminal phosphate | unmodified ribonucleotides in positions: 2, 4, 6, 8, 10, 12, 14, 16 and 18<br>No 3'-terminal phosphate |
| TLR2_4_S73 | 2'-OMe sugar modified ribonucleotides in positions: 2, 4, 6, 8, 10, 12, 14, 16 and 18 | 2'-OMe sugar modified ribonucleotides in positions: 1, 3, 5, 7, 9, 11, 13, 15, 17 and 19 |
|  | unmodified ribonucleotides in positions: 1, 3, 5, 7, 9, 11, 13, 15, 17 and 19<br>No 3'-terminal phosphate | unmodified ribonucleotides in positions: 2, 4, 6, 8, 10, 12, 14, 16 and 18<br>No 3'-terminal phosphate |
| EGFP_5_S763 | 2'-OMe sugar modified ribonucleotides in positions: 2, 4, 6, 8, 10, 12, 14, 16, 18 and 20 | 2'-OMe sugar modified ribonucleotides in positions: 1, 3, 5, 7, 9, 11, 13, 15, 17, 19 and 21 |
|  | unmodified ribonucleotides in positions: 1, 3, 5, 7, 9, 11, 13, 15, 17, 19 and 21<br>No 3'-terminal phosphate | unmodified ribonucleotides in positions: 2, 4, 6, 8, 10, 12, 14, 16, 18 and 20<br>No 3'-terminal phosphate |

Dosage and Administration dsRNA compounds were administered at the end of lung transplantation surgery (immediately after anastomosis opening), by intratracheal instillation to the recipient. The following doses of individual dsRNA compounds were tested in these animal models: 6 μg/mouse, 12.5 μg/mouse, 25 μg/mouse and 50 μg/mouse.

Mouse Syngeneic Lung Transplantation (C57Bl/6->C57Bl/6)

Experimental Design

Both donor and recipient were C57BL/6 mice. Prior to transplantation ischemia reperfusion injury was induced by prolonged cold preservation of the lung transplant by 18 hours of cold storage in a low dextrose solution with components similar to solutions used to preserve human lung transplants (18 hours of cold ischemia time (CIT)). This method induced symptoms consistent with primary graft dysfunction 24 hours post-transplantation. Within 5-10 minutes after reperfusion 25 μg/mouse (or a different dose as described herein) of siRNA specific for control siRNA, TLR2, TLR4 or both TLR2 and TLR4 was administered down the trachea. Lung recipients were assessed 24 hours later for lung injury.

Administration

By intratracheal instillation of dsRNA solution to the lungs; 1 dose of a dsRNA compound or of a combination of dsRNA compounds is administered immediately after anastomosis opening on Day 0.

Evaluation

Lung recipients were evaluated at 24 hours post transplantation through assessing lung function, as measured by:
Gross pathology—appearance of pulmonary edema;
Pulmonary function in the post-transplanted lung—PaO2, oxygenation of arterial blood in the left pulmonary artery;
Intra-airway accumulation of cellular infiltrates; and
Total amount and differential counts of bronchoalveolar lavage (BAL) cells Results In this syngeneic model, mouse isografts exposed to prolonged cold ischemia (18 hours CIT) develop impaired oxygenation, pulmonary edema, increased inflammatory cytokine production and intra-graft and intra-airway accumulation of granulocytes as measured 24 hours post-transplantation. By contrast, mouse lung recipients of 1 hour cold preserved grafts (1 hour CIT) had little evidence of lung injury 24 hours post-transplantation.

Lung recipients that were treated with either dsRNA specific for TLR2 or with a combination of both dsRNA specific for TLR2 and dsRNA specific for TLR4 had significantly better function and significantly less BAL cellular infiltrate, as compared to other treatment groups and to the negative control animals (treated with vehicle or with dsRNA specific for EGFP).

FIG. 1 (representative image of N=5/group) shows that combined administration of dsRNA specific for TLR2 (i.e. TLR2_4_S73), at a dose of 25 µg/mouse and dsRNA specific for TLR4 (i.e. TLR4_4_S500), at a dose of 25 µg/mouse, efficiently reduced pulmonary edema in this mouse model of lung transplantation. No apparent edema was observed in any of the lungs treated with combination of dsRNA for TLR2 and dsRNA for TLR4. Similar results were obtained with a combination of TLR2_7_S73 and TLR4_4_S500 (with a dose of 25 µg/mouse of each). Similar results were obtained with a dose of 12.5 µg/mouse of each of the TLR2 dsRNA compound and TLR4 dsRNA compound (TLR2_7_S73 and TLR4_4_S500), while obvious edema appeared in animals that were treated with vehicle or with dsRNA targeting EGFP).

Figure 2:
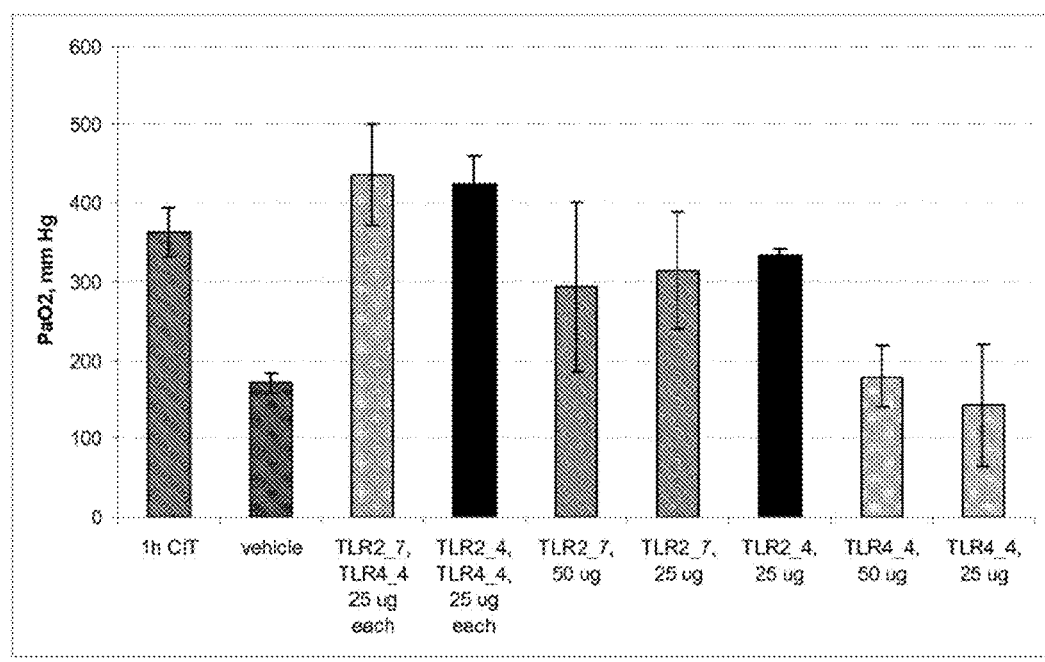
FIG. 2 shows that dual target dsRNA combination, targeting TLR2 and TLR4 genes z93rd and 4th columns), restored pulmonary function in the recipient's lung. Oxygenation of the arterial blood in mice was measured at 24 h after lung transplantation and dsRNA administration. Administration of a single dsRNA targeting TLR2 ($5^{th}$ and $6^{th}$ columns), was also significantly effective in preserving pulmonary function. While administration of a single dsRNA targeting TLR4 ($8^{th}$ and $9^{th}$ columns), was not effective in preserving pulmonary function. Control groups were composed of (i) mice that were administered with vehicle (general negative control, 2nd column), and (ii) mice that underwent lung transplantation (Tx) after only 1 hour of cold preservation (1 hour cold ischemia time (CIT)) (reperfusion control, 1st column).

FIG. 2 shows that impaired recipient pulmonary function, measured at 24 hours after lung transplantation, was restored in mice treated with a combination of dsRNA specific for TLR2 and dsRNA specific for TLR4, as well as in mice treated with a single dsRNA specific for TLR2, but not in mice treated with a single dsRNA directed at TLR4.

Two combinations of dsRNA specific for TLR2 and dsRNA specific for TLR4 were tested in these experiments, at a ratio of 1:1:
(ii) a combination of 25 µg/mouse of each TLR2_7_S73 and TLR4_4_S500, total therapeutic amount: 50 µg/mouse; and
(iii) a combination of 25 µg/mouse of each TLR2_4_S73 and TLR4_4_S500, total therapeutic amount: 50 µg/mouse; and Additional animal groups were tested with either individual dsRNA specific for TLR2 or with an individual dsRNA specific for TLR4.

Two dsRNAs specific for TLR2 were tested in the experiments: TLR2_4_S73 at a dose of 25 µg/mouse and TLR2_7_S73 at doses of 25 µg/mouse and 50 µg/mouse.

One dsRNAs specific for TLR4 was tested in the experiments: TLR4_4_S500 at doses of 25 µg/mouse and 50 µg/mouse.

Negative control animals were treated with vehicle.

The test article (composition comprising a combination of dsRNA TLR2 and TLR4 dsRNA; dsRNA specific for TLR2; dsRNA specific for TLR4; or vehicle) was administered immediately after opening of anastomosis and beginning of reperfusion.

FIG. 2 shows that administration of dual target dsRNA composition (comprising TLR2_7_S73 and TLR4_4_S500 (N=5) or TLR2_4_S73 and TLR4_4_S500 (N=3)), at a dose of 25 µg/mouse of each of the dsRNA compounds, significantly preserved pulmonary function, keeping blood oxygenation at almost normal levels (PaO2=500-530 mm Hg).

Administration of a single dsRNA compound specifically targeting TLR2 (TLR2_7_S73 (N=3) or TLR2_4_S73 (N=5)), at a dose of 25 µg/mouse of the individual dsRNA compound, was also significantly effective in preserving pulmonary function, keeping blood oxygenation at a level similar to the level obtained for 1 hour CIT control group. Similar results were obtained with a higher dose (50 µg/mouse) of a single dsRNA compound specifically targeting TLR2 (TLR2_7_S73; (N=5)).

Significantly, similar results were obtained with two different dsRNA TLR2 compounds (TLR2_7_S73 and TLR2_4_S73) that target different regions of the TLR2 gene.

Administration of a single dsRNA compound specifically targeting TLR4 (TLR4_4_S500), at doses of 25 µg/mouse (N=2) or 50 µg/mouse (N=3), was not effective in preserving pulmonary function, keeping blood oxygenation at a level similar to the level obtained for the vehicle control group.

Figure 3:
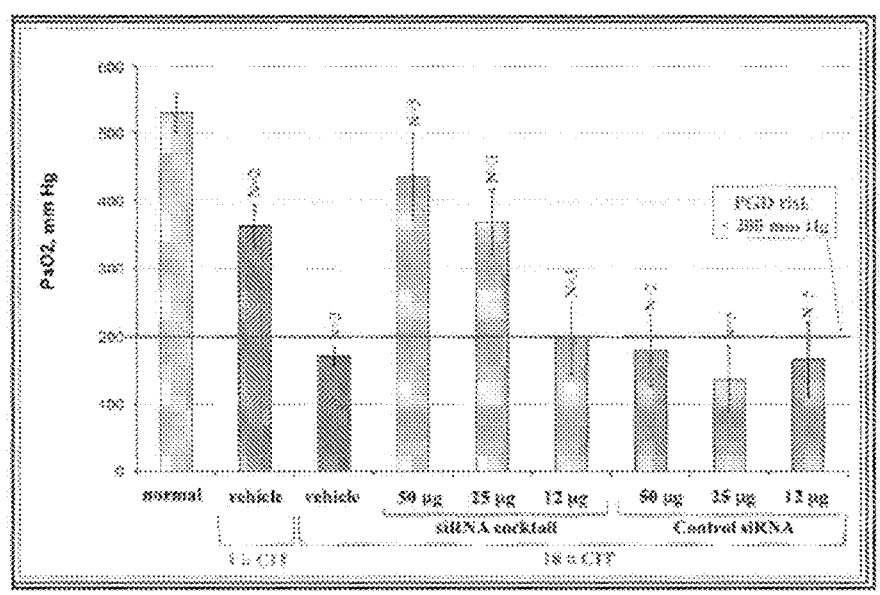
FIG. 3 shows that dual target dsRNA combination, targeting TLR2 and TLR4 genes (columns 4-6), restored pulmonary function in the recipient's lung. Oxygenation of the arterial blood in mice was measured at 24 h after lung transplantation and dsRNA administration. Negative control groups were composed of normal (intact) mice (general negative control, column 1), as well as mice that underwent lung transplantation (Tx) after only 1 hour of cold preservation (1 hour cold ischemia time (CIT)) (reperfusion control, column 2) and mice that were treated with a vehicle (18 hour cold ischemia time (CIT), column 3).

FIG. 3 shows that impaired recipient pulmonary function, measured at 24 hours after lung transplantation, was restored in mice treated with a combination of dsRNA specific for TLR2 and dsRNA specific for TLR4 (identified in FIG. 3 as "siRNA cocktail"). A combination of TLR2_7_S73 and TLR4_4_S500 was used in these experiments, at a ratio of 1:1. Three doses were tested:
(i) a combination of 25 µg/mouse of each TLR2_7_S73 and TLR4_4_S500, total therapeutic amount: 50 µg/mouse;
(ii) a combination of 12.5 µg/mouse of each TLR2_7_S73 and TLR4_4_S500, total therapeutic amount: 25 µg/mouse; and
(iii) a combination of 6 µg/mouse of each TLR2_7_S73 and TLR4_4_S500, total therapeutic amount: 12 µg/mouse Negative control animals were treated with vehicle or with dsRNA specific for EGFP (EGFP_5_S763) at a dose of 50 µg/mouse, 25 µg/mouse or 12.5 µg/mouse.

The test article (composition comprising a combination of TLR2 dsRNA and TLR4 dsRNA; or vehicle; or dsRNA specific for EGFP (identified in FIG. 3 as "control siRNA")) was administered immediately after opening of anastomosis and beginning of reperfusion.

FIG. 3 shows that following lung transplantation after 1 h of cold graft preservation (a reperfusion control), pulmonary function is only slightly worsened (PaO2=363±31 mm Hg), however, prolongation of cold preservation time (18 h CIT)

leads to a dramatic reduction in recipient's pulmonary function (PaO2=170±13 mm Hg for vehicle group), indicating severe PGD (grade 3; ISHLT definition). Administration of dual target siRNA composition (comprising TLR2_7_S73 and TLR4_4_S500), at a dose of 25 µg/mouse of each of the dsRNA compounds, significantly (P<0.005) preserved pulmonary function (PaO2=435±64), keeping blood oxygenation at almost normal levels (PaO2=500-530 mm Hg). Administration of the same doses of non-targeting control dsRNA (EGFP_5_S763 at a dose of 50 µg/mouse) did not improve pulmonary function.

Administration of dual target dsRNA composition (comprising TLR2_7_S73 and TLR4_4_S500), at a dose of 12.5 µg/mouse of each of the dsRNA compounds, was also significantly effective (P<0.05) in preserving pulmonary function, keeping blood oxygenation at a level similar to the level obtained for 1 hour CIT control group. Administration of the same doses of non-targeting control dsRNA (EGFP_5_S763 at a dose of 25 µg/mouse) did not improve pulmonary function.

Administration of dual target dsRNA composition (comprising TLR2_7_S73 and TLR4_4_S500), at a dose of 6 µg/mouse of each of the dsRNA compounds, was not effective in preserving pulmonary function, keeping blood oxygenation at a level similar to the level obtained with vehicle and non-targeting control dsRNA (EGFP_5_S763 at a doses of 50 µg/mouse, 25 µg/mouse and 12.5 µg/mouse), which did not improve pulmonary function.

Figure 4:
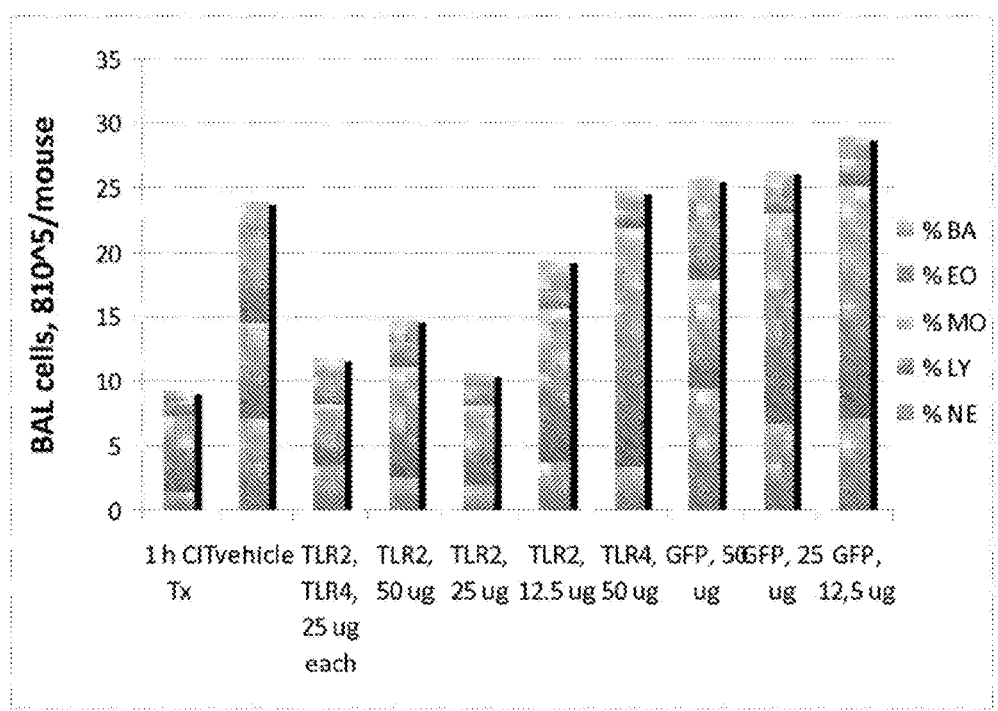
FIG. 4 shows that a combination of dsRNA specific for TLR2 and dsRNA specific for TLR4 (TLR2_4_S73 and TLR4_4_S500) (column 3), as well as an individual treatment comprising dsRNA specific for TLR2 (TLR2_4_S73) (columns 4-6), diminishes intra-airway accumulation of granulocytes in the BAL obtained from transplanted lungs. At 24 h after lung transplantation, BAL was collected from all the mice. Total amount of cells, as well as amounts of different cell populations (neutrophils, lymphocytes, monocytes, eosinophils, basophils) were measured by FACS. Differential cell counts are presented as fractions of total cell counts.

FIG. 4 shows that a combination of dsRNA specific for TLR2 and dsRNA specific for TLR4 (TLR2_4_S73 and TLR4_4_S500), as well as an individual treatment comprising dsRNA specific for TLR2 (TLR2_4_S73), diminished intra-airway accumulation of granulocytes. One of the pathophysiological features of PGD is rapid influx of cellular infiltrates to the interstitial lung space, which is typically detected in patients' chest radiographs. Consistent with this, total bronchoalveolar lavage (BAL) cell counts in mice that underwent lung transplantation after 18 h of CIT (vehicle group), were significantly (P<0.01) higher than those in mice that underwent lung transplantation after 1 h of CIT (24±6 vs 9±4 cells×10^5/lung respectively) (N=2). Treatment with a combination of dsRNA specific for TLR2 and dsRNA specific for TLR4 (TLR2_4_S73 and TLR4_4_S500; (N=5)), at a dose of 25 µg/mouse of each of the dsRNA compounds, as well as an individual treatment comprising dsRNA specific for TLR2 (TLR2_4_S73), at a doses of 50 µg/mouse (N=2) or at a dose of 25 µg/mouse (N=5), diminished cellular BAL infiltration associated with prolonged cold preservation. Moreover, treatment with a combination of dsRNA specific for TLR2 and dsRNA specific for TLR4, as well as an individual treatment comprising dsRNA specific for TLR2, diminished granulocyte (neutrophils, eosinophils, basophils) accumulation in the lung airways.

Administration of a single dsRNA compound specifically targeting TLR4 (TLR4_4_S500), at a dose of 50 µg/mouse (N=2), was not effective in diminishing intra-airway accumulation of granulocytes, keeping intra-airway accumulation of granulocytes at a level similar to the level obtained with vehicle and non-targeting control dsRNA (EGFP_5_S763) at a dose of 50 µg/mouse (N=2), 25 µg/mouse (N=5) or 12.5 µg/mouse (N=5).

Mouse Allogeneic Lung Transplantation (Balb/C->C57Bl/6)

Experimental Design

In this model prolonged cold ischemia prevents lung allograft acceptance mediated by immunosuppression. In this model Balb/c lungs are subjected to 18 hours of cold ischemia time (CIT) and are transplanted into C57Bl/6 recipients that are treated with immunosuppressants: anti-CD40L on post operative day 0 and CTLA4Ig on day 2. In contrast to recipients who received allografts stored for 1 hour, these stored for 18 hours acutely rejected their allografts with marked intragraft accumulation of IFNγ+ CD8 T cells.

Evaluation

Lung recipients were evaluated at 7 days post transplantation through assessing:

Abundance of intragraft IFNγ+CD8+ T cells (by FACS)

Histopathological signs of acute graft rejection, A score

Administration

By intratracheal instillation of dsRNA solution to the lungs; 2 doses of a dsRNA compound or of a combination of dsRNA compounds are administered immediately after anastomosis opening on Day 0 and on Day 1 post lung transplantation.

Results

Figure 5:
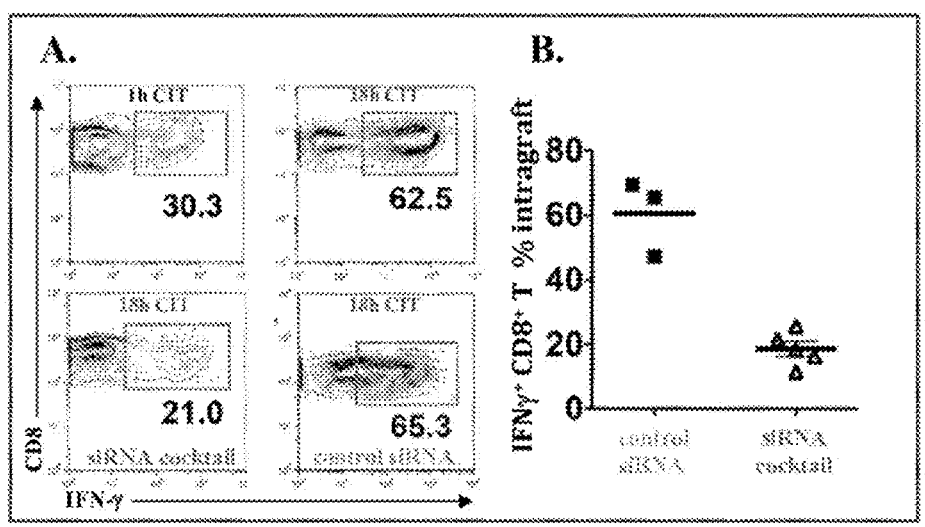
FIG. 5 shows that treatment with a combination of dsRNA specific for TLR2 and dsRNA specific for TLR4 (TLR2_4_S73 and TLR4_4_S500 (identified in the figure as "siRNA cocktail")) diminished abundance of intragraft IFNy+CD8+ T cells on day 7 post allogeneic transplantation. (A). FACS demonstrating representative percent abundance of intragraft IFNy+CD8+ T cells (N>6); (B) Plotted percent abundance of intragraft IFNy+CD8+ T cells.
Figure 6:
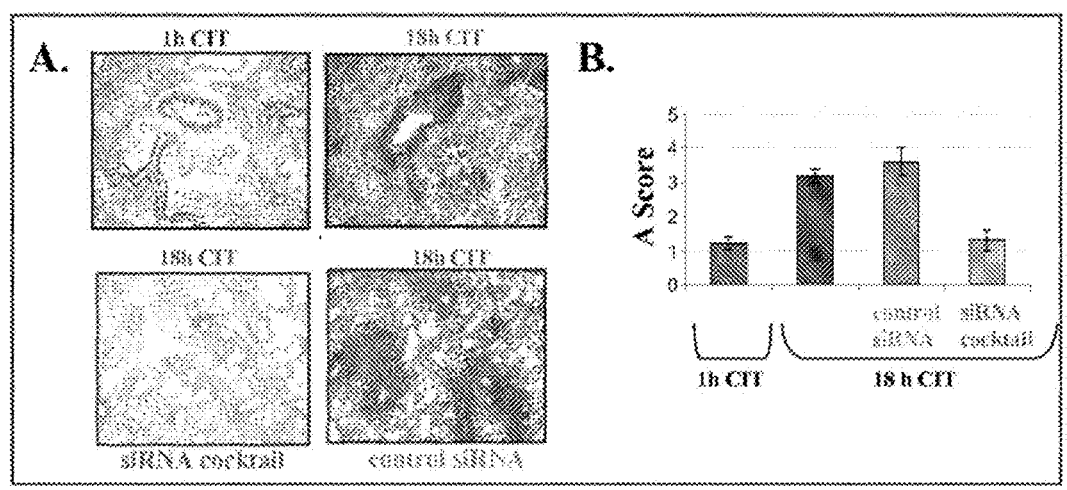
FIG. 6 shows that treatment with a combination of dsRNA specific for TLR2 and dsRNA specific for TLR4 (TLR2_4_S73 and TLR4_4_S500) on days 0 and 1, significantly reduced histopathological signs of acute graft rejection in co-stimulation blockade-treated 1 h CIT or 1 8H CIT Balb/c->B6 transplants, treated intratracheally with either control dsRNA (EGFP 5_5763), or a combination of dsRNA specific for TLR2 and dsRNA specific for TLR4 (TLR2_4_S73 and TLR4_4_S500) (identified as "siRNA cocktail"). (A.) Representative histopathological images (HE) of the recipient lungs on day 7 post allogeneic lung transplantation. (B). Rejection scores evaluated by board-certified lung transplant pathologist in a blinded fashion. The scoring system is typically used in the clinic, as follows: Grade A0 (none), Grade A1 (minimal), Grade A2 (mild), Grade A3 (moderate) and Grade A4 (severe).

Administration of a combination of a dsRNA specific for TLR2 and dsRNA specific for TLR4 (TLR2_4_S73 and TLR4_4_S500, identified as "siRNA cocktail") with a dose of 25 µg/mouse of each of the dsRNA compounds (N=5), or of a single dsRNA specific for TLR2 (TLR2_4_S73), at a dose of 25 µg/mouse (N=4), diminished abundance of intragraft IFNγ+CD8+ T cells in allo-transplantation. In this allogeneic model, in prolonged cold ischemia prevents lung allograft acceptance mediated by immunosuppression. In this model Balb/c lungs are subjected to 18 hours (18 CIT) of cold ischemia and are transplanted into C57BL/6 (B6) recipients that are treated with anti-CD40L on postoperative day (POD) 0 and CTLA4Ig on POD 2. Both of these immunosuppressive reagents are currently in pre-clinic development by major pharmaceutical companies and when used together are generally referred to as double costimulatory blockade treatment (DCB). In contrast to recipients who received allografts stored for 1 hour (1 CIT) (N=6–), 18 CIT Balb/c->DCB+B6 lung recipients (N=6) acutely rejected their allografts with marked intragraft accumulation of IFNγ+CD8+T (FIG. 5 A, upper panel). This rejection was also evident by histopathological evaluation (FIG. 6 A,B).

In this model, control dsRNA (EGFP_5_S763) treated lung recipients (N=3) acutely rejected their allografts with significantly elevated IFNγ+CD8+ T cells accumulation in allograft tissue. By contrast, recipient mice treated with a combination of a dsRNA specific for TLR2 and dsRNA specific for TLR4 (TLR2_4_S73 and TLR4_4_S500, identified as "siRNA cocktail"; (N=5)) on days 0 and 1, had significantly decreased abundance of intragraft IFNγ+ CD8+ T cells (FIG. 5 A, B), as well as significantly less histological evidence of acute rejection (FIG. 6 A, B).

These experiments show that targeting TLR function using dsRNA compounds specific for TLR2 or a combination of dsRNA compounds specific for TLR2 and TLR4 significantly improves/prevents lung graft injury. Lung function in TLR2 or TLR2- and TLR4-dsRNA treated recipients was similar to lung recipients of 1 hour cold preserved graft, indicating that this method may be useful in preventing/treating primary graft dysfunction in lung transplant recipients. These experimental procedures and dsRNA treatments

Example 5: dsRNA Oligonucleotide Sense and Antisense Pairs

The Sequence Listing provides sense and antisense oligonucleotides for generating double-stranded oligonucleotide compounds, useful in carrying out the methods disclosed herein.

The sense and antisense strands of the TLR2 double-stranded oligonucleotides are provided in sense strand sequences set forth in SEQ ID NOs: 5-722; 1441-2246; 3053-4152; and 5253-5545 and antisense strand sequences set forth in SEQ ID NOs: 723-1440; 2247-3052; 4153-5252 and 5546-5838.

The sense and antisense strands of the TLR4 double-stranded oligonucleotides are provided in sense strand sequences set forth in SEQ ID NOs: 5839-7075, 8313-8458, 8605-10318, 12033-12084 and antisense strand sequences set forth in SEQ ID NOs: 7076-8312, 8459-8604, 10319-12032, 12085-12136.

The contents of the articles, patents, and patent applications, and all other documents and electronically available information mentioned or cited herein, are hereby incorporated by reference in their entirety to the same extent as if each individual publication was specifically and individually indicated to be incorporated by reference.

Applicants reserve the right to physically incorporate into this application any and all materials and information from any such articles, patents, patent applications, or other physical and electronic documents.

It will be readily apparent to one skilled in the art that varying substitutions and modifications can be made to the invention disclosed herein without departing from the scope and spirit of the invention. Thus, such additional embodiments are within the scope of the present invention and the following claims. The present disclosures teach one skilled in the art to test various combinations described herein toward generating therapeutic combination with improved activity for treating lung disorders or injury in a mammal. Such improved activity can include e.g., improved stability, improved bioavailability, improved activation of cellular responses mediating RNAi. Therefore, the specific embodiments described herein are not limiting and one skilled in the art can readily appreciate that additional specific combinations can be tested without undue experimentation toward identifying therapeutic combinations with improved activity.

The inventions illustratively described herein may suitably be practiced in the absence of any element or elements, limitation or limitations, not specifically disclosed herein. Thus, for example, the terms "a" and "an" and "the" and similar referents in the context of describing the invention (especially in the context of the following claims) are to be construed to cover both the singular and the plural, unless otherwise indicated herein or clearly contradicted by context. The terms "comprising", "having," "including," "containing", etc. shall be read expansively and without limitation (e.g., meaning "including, but not limited to,"). Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and sub-generic groupings falling within the generic disclosure also form part of the invention. This includes the generic description of the invention with a proviso or negative limitation removing any subject matter from the genus, regardless of whether or not the excised material is specifically recited herein. Other embodiments are within the following claims. In addition, where features or aspects of the invention are described in terms of Markush groups, those skilled in the art will recognize that the invention is also thereby described in terms of any individual member or subgroup of members of the Markush group.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US09822362B2). An electronic copy of the "Sequence Listing" will also be available from the USPTO upon request and payment of the fee set forth in 37 CFR 1.19(b)(3).

That which is claimed is:

1. A method of treating a lung disorder, lung disease, or lung injury associated with lung transplantation in a subject in need thereof, comprising administering to the subject a therapeutically-effective amount of at least one TLR2 inhibitor or a pharmaceutically acceptable salt thereof, wherein the TLR2 inhibitor comprises a nucleic acid molecule targeting a TLR2 gene, thereby treating the lung disorder, lung disease, or lung injury associated with lung transplantation in said subject, wherein the lung disorder associated with lung transplantation is selected from the group consisting of: inflammation, graft rejection, primary graft failure, ischemia-reperfusion injury, reperfusion injury, reperfusion edema, allograft dysfunction, acute graft dysfunction, pulmonary reimplantation response, bronchiolitis obliterans, and primary graft dysfunction (PGD).

2. The method according to claim 1, wherein the lung disorder associated with lung transplantation is PGD.

3. The method according to claim 1, wherein the treatment prevents or reduces the symptoms of cold ischemic-associated PGD or warm ischemia-associated PGD.

4. The method according to claim 1, wherein the administration is local administration.

5. The method according to claim 4, wherein the administration is by inhalation or by intratracheal instillation.

6. The method according to claim 1, wherein the nucleic acid molecule comprises a double-stranded oligonucleotide.

7. The method according to claim 6, wherein the double-stranded oligonucleotide comprises:
(a) a sense strand and an antisense strand;
(b) each strand is independently 17 to 40 nucleotides in length;
(c) a 17 to 40 nucleotide sequence of the antisense strand is complementary to a sequence of an mRNA encoding TLR2; and
(d) a 17 to 40 nucleotide sequence of the sense strand is complementary to the antisense strand.

8. The method according to claim 7, wherein the double-stranded oligonucleotide comprises a structure (A1):

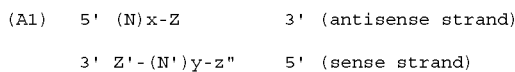

wherein each of N and N' is an unmodified ribonucleotide, a modified ribonucleotide, or an unconventional moiety;
wherein each of (N)x and (N')y is an oligonucleotide in which each consecutive N or N' is joined to the next N or N' by a covalent bond;
wherein each of Z and Z' is independently present or absent, but if present is independently 1-5 consecutive nucleotides or unconventional moieties or a combination thereof covalently attached at the 3' terminus of the strand in which it is present;
wherein z" may be present or absent, but if present is a capping moiety covalently attached at the 5' terminus of (N')y;
wherein each of x and y is independently an integer between 17 and 40;
wherein the sequence of (N')y is complementary to the sequence of (N)x; and
wherein (N)x comprises an antisense sequence to an mRNA encoding TLR2 having a sequence forth in SEQ ID NO:1.

9. The method according to claim 8, wherein x=y=19.

10. The method according to claim 7, wherein the double-stranded oligonucleotide comprises a structure (A2):

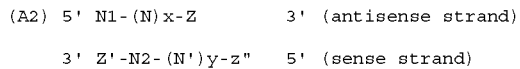

wherein each of N2, N and N' is independently an unmodified ribonucleotide, a modified ribonucleotide, or an unconventional moiety;
wherein each of (N)x and (N')y is an oligonucleotide in which each consecutive N or N' is joined to the adjacent N or N' by a covalent bond;
wherein each of x and y is independently an integer between 17 and 39;
wherein the sequence of (N')y is complementary to the sequence of (N)x and wherein (N)x is complementary to a consecutive sequence in an mRNA encoding TLR2;
wherein N1 is covalently bound to (N)x and is mismatched to the mRNA encoding TLR2;
wherein N1 is a moiety selected from the group consisting of uridine, modified uridine, ribothymidine, modified ribothymidine, deoxyribothymidine, modified deoxyribothymidine, riboadenine, deoxyriboadenine, and modified deoxyriboadenine;
wherein z" may be present or absent, but if present is a capping moiety covalently attached at the 5' terminus of N2-(N')y; and
wherein each of Z and Z' is independently present or absent, but if present is independently 1-5 consecutive nucleotides or unconventional moieties or a combination thereof covalently attached at the 3' terminus of the strand in which it is present.

11. The method according to claim 10, wherein x=y=18.

12. The method according to claim 1, wherein the at least one TLR2 inhibitor is administered to said subject prior to or during lung transplantation.

13. The method according to claim 1, wherein the at least one TLR2 inhibitor is administered to said subject following lung transplantation.

14. The method according to claim 8, wherein one of Z and Z' is present.

15. The method according to claim 8, wherein both of Z and Z' is present.

16. The method according to claim 8, wherein z" is present.

17. The method according to claim 10, wherein one of Z and Z' is present.

18. The method according to claim 10, wherein both of Z and Z' is present.

19. The method according to claim 10, wherein z" is present.

* * * * *